US011744936B2

(12) United States Patent
Lane et al.

(10) Patent No.: US 11,744,936 B2
(45) Date of Patent: Sep. 5, 2023

(54) SYSTEMS, APPARATUS, AND METHODS FOR FLUID INFUSION

(71) Applicant: 410 Medical, Inc., Durham, NC (US)

(72) Inventors: Andrew W. Lane, Rolesville, NC (US); Galen C. Robertson, Apex, NC (US); Savannah K. Carlsen, Durham, NC (US); Robert W. Titkemeyer, Wimberley, TX (US); Luke D. Oltmans, Durham, NC (US)

(73) Assignee: 410 Medical, Inc., Durham, NC (US)

( * ) Notice: Subject to any disclaimer, the term of this patent is extended or adjusted under 35 U.S.C. 154(b) by 0 days.

(21) Appl. No.: 17/845,560

(22) Filed: Jun. 21, 2022

(65) Prior Publication Data

US 2022/0313901 A1    Oct. 6, 2022

Related U.S. Application Data

(63) Continuation of application No. PCT/US2022/019381, filed on Mar. 8, 2022.
(Continued)

(51) Int. Cl.
*A61M 5/14* (2006.01)
*A61M 5/145* (2006.01)
(Continued)

(52) U.S. Cl.
CPC ........ *A61M 5/1413* (2013.01); *A61M 5/1409* (2013.01); *A61M 5/14546* (2013.01);
(Continued)

(58) Field of Classification Search
CPC .... A61M 2005/31588; A61M 2205/75; A61M 2205/8243; A61M 5/1409; A61M 5/1413;
(Continued)

(56) References Cited

U.S. PATENT DOCUMENTS 4,202,333 A    5/1980  Thill et al.
4,569,662 A    2/1986  Dragan
(Continued)

FOREIGN PATENT DOCUMENTS

DE    10326306 A1    12/2004
FR     2690839 A1    11/1993
(Continued)

OTHER PUBLICATIONS

Examination Report, dated Apr. 28, 2022, for Canadian Patent Application No. 2,977,652 (4 total pages).
(Continued)

*Primary Examiner* — Brandy S Lee
(74) *Attorney, Agent, or Firm* — COOLEY LLP

(57) ABSTRACT

In some embodiments, a system can include a fluid delivery assembly and a drive assembly. The fluid delivery assembly is configured to be releasably mechanically and, optionally, electrically coupled to the drive assembly. When the fluid delivery assembly is releasably coupled to the drive assembly, the drive assembly can control delivery of fluid from the fluid delivery assembly (e.g., to a patient). For example, the drive assembly can be releasably coupled to the fluid delivery assembly to control delivery of fluid from the fluid delivery assembly to provide continuous (e.g., non-pulsatile) fluid flow from the fluid delivery assembly.

18 Claims, 61 Drawing Sheets

Related U.S. Application Data

(60) Provisional application No. 63/291,090, filed on Dec. 17, 2021, provisional application No. 63/158,309, filed on Mar. 8, 2021.

(51) Int. Cl.
*A61M 5/168* (2006.01)
*A61M 5/44* (2006.01)

(52) U.S. Cl.
CPC .......... *A61M 5/16813* (2013.01); *A61M 5/44* (2013.01); *A61M 2205/8243* (2013.01)

(58) Field of Classification Search
CPC .......... A61M 5/14216; A61M 5/14546; A61M 5/16813; A61M 5/1782; A61M 5/36; A61M 5/44
See application file for complete search history.

(56) References Cited

U.S. PATENT DOCUMENTS

| | | | |
|---|---|---|---|
| 4,594,073 A | 6/1986 | Stine | |
| 4,687,472 A | 8/1987 | Gross | |
| 4,758,233 A | 7/1988 | Phillips et al. | |
| 4,896,678 A | 1/1990 | Ogawa | |
| 4,919,649 A | 4/1990 | Timothy et al. | |
| 4,968,303 A | 11/1990 | Clarke et al. | |
| 5,139,488 A | 8/1992 | Klein | |
| 5,141,504 A | 8/1992 | Herweck et al. | |
| 5,203,839 A | 4/1993 | Skaggs | |
| 5,304,147 A | 4/1994 | Johnson et al. | |
| 5,389,070 A | 2/1995 | Morell | |
| 5,395,375 A | 3/1995 | Turkel et al. | |
| 5,733,258 A | 3/1998 | Lane | |
| 5,807,340 A | 9/1998 | Pokras | |
| 5,865,805 A | 2/1999 | Ziemba | |
| 5,913,874 A | 6/1999 | Berns et al. | |
| 5,924,206 A | 7/1999 | Cote et al. | |
| 6,068,624 A | 5/2000 | Benecke et al. | |
| 6,117,158 A | 9/2000 | Measamer et al. | |
| 6,142,974 A | 11/2000 | Kistner et al. | |
| 6,213,984 B1 | 4/2001 | Lane et al. | |
| 6,257,265 B1 * | 7/2001 | Brunner .............. | G05D 23/1931 137/340 |
| 6,260,737 B1 | 7/2001 | Gruendeman | |
| 6,439,439 B1 | 8/2002 | Rickard et al. | |
| 6,475,193 B1 | 11/2002 | Park | |
| 6,585,696 B2 | 7/2003 | Petersen et al. | |
| 6,716,195 B2 | 4/2004 | Nolan, Jr. et al. | |
| 6,802,824 B2 | 10/2004 | Mickley et al. | |
| 6,989,000 B2 | 1/2006 | Schreijag et al. | |
| 7,041,084 B2 | 5/2006 | Fojtik | |
| 7,160,087 B2 | 1/2007 | Fathallah et al. | |
| 7,553,294 B2 | 6/2009 | Lazzaro et al. | |
| 7,637,279 B2 | 12/2009 | Amley et al. | |
| 7,691,085 B2 | 4/2010 | Dedig et al. | |
| 7,833,204 B2 | 11/2010 | Picha | |
| 7,846,130 B2 | 12/2010 | Elazari-Volcani et al. | |
| 7,988,677 B2 | 8/2011 | Fojtik | |
| 8,047,407 B2 | 11/2011 | Wheeler et al. | |
| 8,066,629 B2 | 11/2011 | Dlugos | |
| 8,142,365 B2 | 3/2012 | Miller | |
| 8,357,147 B2 | 1/2013 | Burkinshaw et al. | |
| D679,011 S | 3/2013 | Kitayama et al. | |
| 8,415,407 B2 | 4/2013 | Beyar et al. | |
| 8,486,155 B2 | 7/2013 | McAlister et al. | |
| D687,549 S | 8/2013 | Johnson et al. | |
| 8,539,644 B2 | 9/2013 | Fojtik | |
| 8,631,935 B2 | 1/2014 | Tomes et al. | |
| 8,672,900 B2 | 3/2014 | Fojtik | |
| 8,746,452 B2 | 6/2014 | Tomes et al. | |
| 8,747,356 B2 | 6/2014 | Cocker et al. | |
| D744,099 S | 11/2015 | Osada | |
| 9,192,711 B2 * | 11/2015 | Barnes .............. | A61M 5/16854 |
| D750,244 S | 2/2016 | Osada | |
| 9,283,352 B2 | 3/2016 | Tomes et al. | |
| 9,295,778 B2 | 3/2016 | Kamen et al. | |
| 9,522,753 B2 | 12/2016 | Tomes et al. | |
| 10,016,564 B2 | 7/2018 | Piehl et al. | |
| 10,322,227 B2 | 6/2019 | Piehl et al. | |
| 10,391,257 B2 | 8/2019 | Piehl et al. | |
| 10,661,029 B2 | 5/2020 | Robertson et al. | |
| 10,780,258 B2 | 9/2020 | Pettini et al. | |
| 11,458,256 B2 | 10/2022 | Piehl et al. | |
| 2002/0116021 A1 | 8/2002 | Gordon | |
| 2004/0039344 A1 | 2/2004 | Baldwin et al. | |
| 2004/0116873 A1 | 6/2004 | Fojtik | |
| 2004/0133152 A1 | 7/2004 | Reilly et al. | |
| 2004/0138677 A1 | 7/2004 | Little et al. | |
| 2005/0137575 A1 | 6/2005 | Thompson et al. | |
| 2005/0148934 A1 | 7/2005 | Martens et al. | |
| 2005/0215976 A1 | 9/2005 | Wallen | |
| 2005/0261633 A1 | 11/2005 | Khalaj | |
| 2005/0261693 A1 | 11/2005 | Miller et al. | |
| 2006/0206144 A1 | 9/2006 | Miersch | |
| 2006/0247578 A1 | 11/2006 | Arguedas et al. | |
| 2006/0293560 A1 | 12/2006 | Nguyen et al. | |
| 2007/0235083 A1 | 10/2007 | Dlugos | |
| 2008/0083813 A1 | 4/2008 | Zemlok et al. | |
| 2008/0098564 A1 | 5/2008 | Fojtik | |
| 2008/0132850 A1 | 6/2008 | Fumiyama et al. | |
| 2008/0269671 A1 | 10/2008 | Lin et al. | |
| 2008/0287910 A1 | 11/2008 | Picha | |
| 2009/0088702 A1 | 4/2009 | Fojtik | |
| 2009/0112164 A1 | 4/2009 | Reilly et al. | |
| 2010/0204649 A1 | 8/2010 | Miller et al. | |
| 2010/0217122 A1 | 8/2010 | Fumiyama et al. | |
| 2010/0249719 A1 | 9/2010 | Fojtik | |
| 2010/0264194 A1 | 10/2010 | Huang et al. | |
| 2011/0208158 A1 | 8/2011 | Sigmon, Jr. et al. | |
| 2011/0212251 A1 | 9/2011 | Buga | |
| 2011/0282197 A1 | 11/2011 | Martz | |
| 2011/0282324 A1 | 11/2011 | Kurokawa et al. | |
| 2011/0282382 A1 | 11/2011 | McAlister et al. | |
| 2013/0237955 A1 | 9/2013 | Neta et al. | |
| 2013/0345644 A1 | 12/2013 | Fojtik | |
| 2014/0291355 A1 | 10/2014 | Fago | |
| 2014/0316369 A1 | 10/2014 | Centeno et al. | |
| 2014/0323984 A1 | 10/2014 | Bruce et al. | |
| 2015/0025500 A1 | 1/2015 | Piehl et al. | |
| 2015/0209821 A1 | 7/2015 | Pfahnl et al. | |
| 2015/0335530 A1 | 11/2015 | Aguerre et al. | |
| 2016/0166761 A1 | 6/2016 | Piehl et al. | |
| 2017/0281875 A1 | 10/2017 | Piehl et al. | |
| 2017/0319783 A1 | 11/2017 | Piehl et al. | |
| 2019/0365567 A1 | 12/2019 | Balkenbush et al. | |
| 2019/0374724 A1 * | 12/2019 | Piehl .................. | A61M 5/3146 |
| 2020/0282135 A1 | 9/2020 | Breitweiser et al. | |

FOREIGN PATENT DOCUMENTS

| | | | |
|---|---|---|---|
| JP | H06503271 A | 4/1994 | |
| JP | 2001521417 A | 11/2001 | |
| JP | 2004527333 A | 9/2004 | |
| JP | 2013507191 A | 3/2013 | |
| NL | 8006197 A | 6/1982 | |
| WO | WO-9306940 A1 | 4/1993 | |
| WO | WO-9843690 A1 | 10/1998 | |
| WO | WO-9917833 A1 | 4/1999 | |
| WO | WO-02094343 A2 | 11/2002 | |
| WO | WO-2008024814 A2 * | 2/2008 | ............ A61J 1/1406 |
| WO | WO-2010048753 A1 | 5/2010 | |
| WO | WO-2011044343 A2 | 4/2011 | |
| WO | WO-2012058070 A2 | 5/2012 | |
| WO | WO-2014074807 A1 | 5/2014 | |
| WO | WO-2014145354 A1 | 9/2014 | |
| WO | WO-2016138018 A2 | 9/2016 | |
| WO | WO-2022192285 A1 | 9/2022 | |

OTHER PUBLICATIONS

Examination Report, dated Nov. 14, 2019, for European Patent Application No. 16708327.8 (4 total pages).

(56) References Cited

OTHER PUBLICATIONS

Examination Report No. 1 dated Nov. 6, 2019, for Australian Application No. 2016222871, 3 pages.
Final Office Action, dated Jul. 18, 2018, for U.S. Appl. No. 15/612,668 (24 pages).
Final Office Action issued by The United States Patent and Trademark Office for U.S. Appl. No. 14/214,977, dated Aug. 31, 2017, 51 pages.
Final Office Action issued by The United States Patent and Trademark Office for U.S. Appl. No. 14/214,977, dated Dec. 18, 2015, 30 pages.
Final Office Action issued by The United States Patent and Trademark Office for U.S. Appl. No. 15/051,456, dated Sep. 27, 2018, 27 pages.
Final Office Action, dated Oct. 8, 2021, for U.S. Appl. No. 16/548,490 (33 total pages).
International Preliminary Report on Patentability issued by the International Searching Authority for Application No. PCT/US2014/030097, dated Sep. 15, 2015, 9 pages.
International Preliminary Report on Patentability, dated Sep. 8, 2017, corresponding to International Patent Application No. PCT/US2016/019167 (9 pages).
International Search Report and the Written Opinion of the International Searching Authority, dated Aug. 26, 2016, corresponding to International Patent Application No. PCT/US2016/019167 (13 pages).
International Search Report and Written Opinion issued by the International Searching Authority for Application No. PCT/US2014/030097, dated Aug. 6, 2014, 12 pages.
Invitation to Pay Fee for International Application No. PCT/US2022/019381 dated May 26, 2022, 2 pages.
MULTI-AD® Transfer Set (MAT4100), BRAUN, product description, httg://us.bbraunoem.com/cgs/rde/xchg/oem-bbraunoem-en-us . . . , date unknown but believed to be before the priority date of the present application, printed from the internet Sep. 21, 2015, 1 page.
Non-Final Office Action, dated Dec. 16, 2016, for U.S. Appl. No. 14/214,977 (55 total pages).
Non-Final Office Action, dated Jan. 14, 2021, for U.S. Appl. No. 16/548,490 (33 total pages).
Non-Final Office Action issued by The United States Patent and Trademark Office for U.S. Appl. No. 14/214,977, dated Jul. 13, 2015, 27 pages.
Non-Final Office Action issued by The United States Patent and Trademark Office for U.S. Appl. No. 14/214,977, dated Jun. 10, 2016, 42 pages.
Non-Final Office Action issued by The United States Patent and Trademark Office for U.S. Appl. No. 15/051,456, dated Dec. 26, 2017, 50 pages.
Non-Final Office Action issued by The United States Patent and Trademark Office for U.S. Appl. No. 15/612,668, dated Feb. 15, 2018, 75 pages.
Non-Final Office Action issued by The United States Patent and Trademark Office for U.S. Appl. No. 15/612,668, dated Feb. 7, 2019, 24 pages.
Non-Final Office Action issued by The United States Patent and Trademark Office for U.S. Appl. No. 15/612,668, dated Oct. 18, 2017, 26 pages.
Non-Final Office Action issued by The United States Patent and Trademark Office for U.S. Appl. No. 15/612,709, dated Sep. 18, 2017, 39 pages.
Notice of Allowance, dated May 31, 2022, for U.S. Appl. No. 16/548,490 (12 total pages).
Notice of Allowance issued by the United States Patent and Trademark Office for U.S. Appl. No. 15/051,456, dated Feb. 21, 2019, 11 pages.
Notice of Allowance issued by the United States Patent and Trademark office for U.S. Appl. No. 15/612,668, dated May 23, 2019, 10 pages.
Notice of Allowance issued by The United States Patent and Trademark Office for U.S. Appl. No. 15/612,709, dated Jun. 6, 2018, 14 pages.
Office Action issued in Japanese Patent Application No. 2017-562966, dated Aug. 4, 2020, 13 pages.
Office Action issued in Japanese Patent Application No. 2017-562966, dated Jan. 21, 2020, 10 pages.
International Search Report and Written Opinion for Application No. PCT/US2022/019381, dated Jul. 26, 2022 (10 pages).
Invitation to Pay Additional Fees and, Where Applicable, Protest Fee, dated Jun. 22, 2016, for International Application No. PCT/US2016/019167 (6 total pages).
Non-Final Office Action for U.S. Appl. No. 17/959,194, dated Dec. 19, 2022 (8 pages).
Non-Final Office Action, dated Feb. 13, 2013, for U.S. Appl. No. 17/959,194 (10 total pages).

* cited by examiner

SYSTEMS, APPARATUS, AND METHODS FOR FLUID INFUSION

CROSS-REFERENCE TO RELATED APPLICATIONS

This application is a continuation of International Patent Application No. PCT/US2022/019381, entitled "Systems, Apparatus, and Methods for Fluid Infusion," filed Mar. 8, 2022, which claims priority to and the benefit of U.S. Provisional Patent Application Ser. No. 63/291,090 entitled "Infusion Mechanism Systems, Apparatus, and Methods of Using the Same," filed with the United States Patent and Trademark Office on Dec. 17, 2021, and U.S. Provisional Patent Application Ser. No. 63/158,309 entitled "Systems, Apparatus, and Methods for Fluid Infusion," filed with the United States Patent and Trademark Office on Mar. 8, 2021, the disclosure of each of which is incorporated herein by reference in their entireties.

BACKGROUND

Many medical conditions require the delivery of intravenous fluids and/or blood products, and some conditions, such as hemorrhagic shock, require rapid delivery of the fluids and blood products. Rapid infusers are typically bulky and complex to set up and use. Additionally, rapid infusers are typically limited in the amount of pressure they can generate (e.g., to 300 mmHg) due to the types of mechanisms they use to generate pressure (external pressurization of the intravenous (IV) bag, peristaltic pump). While they may be able to deliver fluids and blood quickly through large-bore IV access (upwards of 1000 mL/min), typical rapid infusers have limited flow rates through peripheral IVs. Furthermore, single-syringe pumps used for fluid delivery require a period of zero flow between syringe ejections while the syringe is filled with fluid, resulting in a highly-pulsatile pressure profile which limits flow rate and has higher pressures during peak flow.

Therefore, there is a need for systems, apparatus, and methods for fluid infusion that allow for easy transportation, simple set up and user control, and continuous fluid flow at high flow rates through peripheral IV sites.

SUMMARY

In some embodiments, a system can include a fluid delivery assembly and a drive assembly. The fluid delivery assembly is configured to be releasably mechanically and, optionally, electrically coupled to the drive assembly. When the fluid delivery assembly is releasably coupled to the drive assembly, the drive assembly can control delivery of fluid from the fluid delivery assembly (e.g., to a patient). For example, the drive assembly can be releasably coupled to the fluid delivery assembly to control delivery of fluid from the fluid delivery assembly to provide continuous (e.g., non-pulsatile) fluid flow from the fluid delivery assembly.

DETAILED DESCRIPTION

Figure 1A:
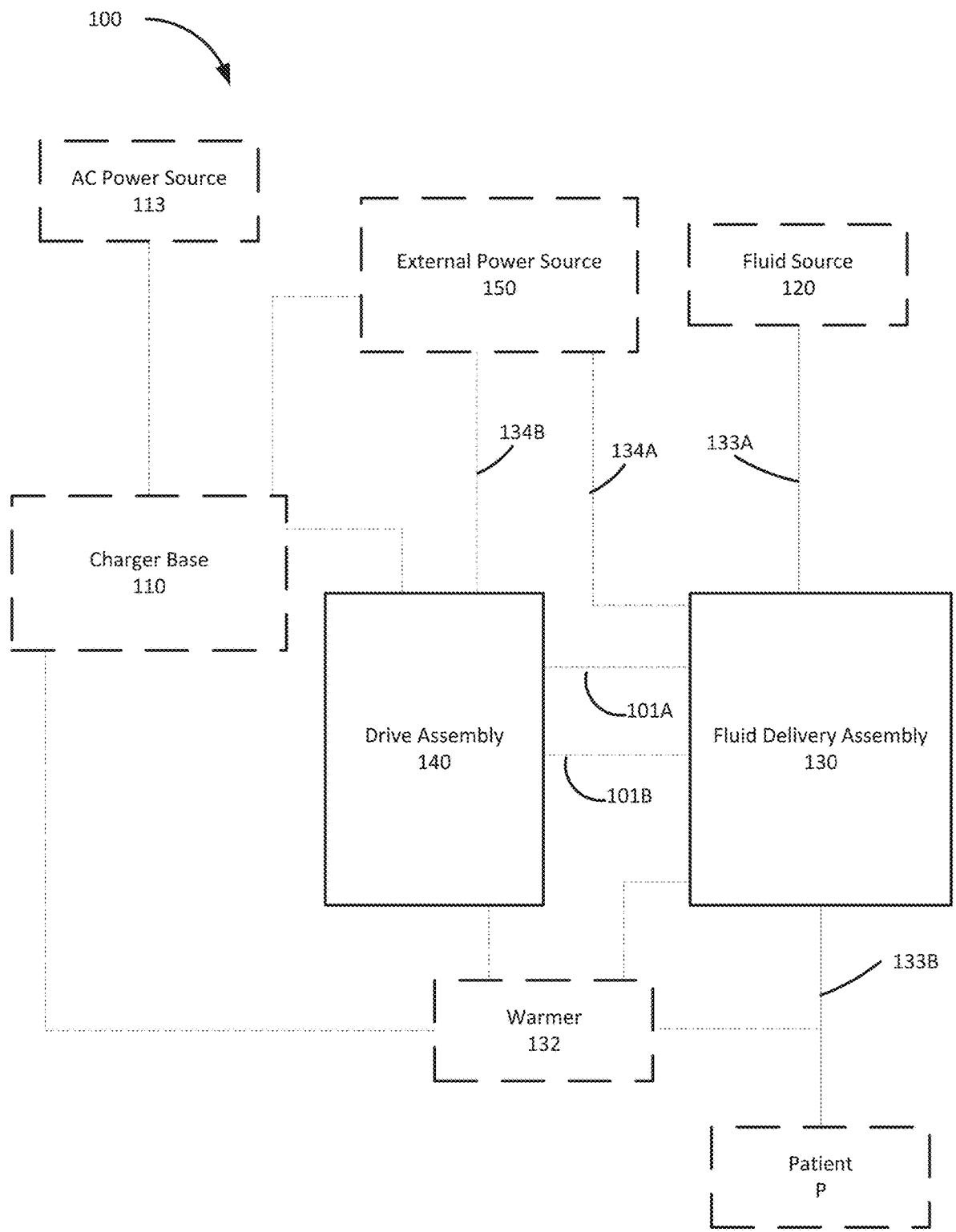
FIG. 1A is a schematic illustration of a system, according to an embodiment.

Systems, apparatus, and methods for fluid infusion are described herein. In some embodiments, the systems include a small, portable rapid infuser for IV fluids and blood administration. Many medical conditions require the delivery of intravenous fluids and/or blood products, and some conditions, such as hemorrhagic shock, require rapid delivery of the fluids and blood products. Unlike many other rapid infusers that are bulky and complex to set up and use, the systems, apparatus, and methods described herein allow for handheld, portable use and simple setup with a single-action connection between the reusable portion of the device and the disposable IV tubing.

In some embodiments, a system includes a fluid delivery assembly and a drive assembly. The fluid delivery assembly includes a fluid pump, a first electrical connection, a second electrical connection, fluid inlet tubing, and fluid outlet tubing. The fluid inlet tubing is coupled to the fluid pump and configured to be coupled to a source of fluid. The fluid outlet tubing is coupled to the fluid pump and configured to be coupled to a patient. The second electrical connection is configured to be reversibly coupled to an external power storage component. The drive assembly includes an electrical connection configured to be reversibly coupled to the first electrical connection of the fluid delivery assembly. The drive assembly is configured to operate, based on power received from the external power storage component via the first electrical connection of the fluid delivery assembly and the electrical connection of the drive assembly, to control the fluid pump such that fluid is drawn into the fluid delivery assembly via the fluid inlet tubing and delivered from the fluid delivery assembly via the fluid outlet tubing.

In some embodiments, a system includes a fluid delivery assembly and a drive assembly. The fluid delivery assembly includes a fluid delivery assembly housing, a drive mechanism, at least one reservoir, at least one piston, fluid inlet tubing, and fluid outlet tubing. The fluid inlet tubing is coupled to the at least one reservoir and configured to be coupled to a source of fluid. The fluid outlet tubing is coupled to the at least one reservoir and configured to be coupled to a patient. The drive mechanism is configured to control movement of the at least one piston such that fluid is drawn into the at least one reservoir via the fluid inlet tubing and fluid is delivered from the at least one reservoir via the fluid outlet tubing. The at least one reservoir, the piston, and at least a portion of the drive mechanism are disposed within the fluid delivery assembly housing. The drive assembly includes a drive assembly housing, a power storage component, a motor, and a drive transfer mechanism operatively coupled to the motor. The motor is configured to operate based on power provided by the power storage component. The power storage component, the motor, and at least a portion of the drive transfer mechanism are disposed within the drive assembly housing. The drive transfer mechanism is reversibly couplable to the drive mechanism of the fluid delivery assembly to control movement of the at least one piston of the fluid delivery assembly via the drive mechanism under the control of the motor.

In some embodiments, a method includes coupling a drive mechanism of a fluid delivery assembly to a drive transfer mechanism of a drive assembly; initiating operation of the drive assembly such that the drive assembly, using power received from an external power source coupled to the drive assembly, controls movement of at least one piston of the fluid delivery assembly relative to at least one reservoir of the fluid delivery assembly to draw fluid into the fluid delivery assembly and deliver fluid from the fluid delivery assembly; and decoupling the drive assembly from the external power source by separating an electrical contact of the external power source from an electrical contact of the drive assembly, the drive assembly continuing to control movement of the at least one piston of the fluid delivery assembly relative to the at least one reservoir to draw fluid into the fluid delivery assembly and deliver fluid from the fluid delivery assembly when the drive assembly is decoupled from the external power source.

In some embodiments, a method includes coupling a drive mechanism of a fluid delivery assembly to a drive transfer mechanism of a drive assembly; initiating operation of the drive assembly such that the drive assembly, using power received from an external power source coupled to the drive assembly, controls movement of at least one piston of the fluid delivery assembly relative to at least one reservoir of the fluid delivery assembly to draw fluid into the fluid delivery assembly and deliver fluid from the fluid delivery assembly; and decoupling the external power source from a charger base by separating an electrical contact of the external power source from an electrical contact of the charger base, the drive assembly continuing to control movement of the at least one piston of the fluid delivery assembly relative to the at least one reservoir to draw fluid into the fluid delivery assembly and deliver fluid from the fluid delivery assembly when the external power source is decoupled from the charger base.

FIG. 1A is a schematic illustration of a system 100 (also referred to as an infusion mechanism, an infuser, a rapid infuser, or a dual reservoir infuser). The system 100 can include a fluid delivery assembly 130 (also referred to as a disposable tubing assembly or a disposable cartridge assembly) and a drive assembly 140 (also referred to as a reusable drive unit). The fluid delivery assembly 130 is configured to be releasably mechanically and, optionally, electrically coupled to the drive assembly 140. For example, the fluid delivery assembly 130 can be coupled to the drive assembly 140 via a mechanical coupling 101A (including drive engagement components, retention components, and/or alignment components) and an electrical coupling 101B (configured for the transfer of power and/or data). When the fluid delivery assembly 130 is releasably coupled to the drive assembly 140, the drive assembly 140 can control delivery of fluid from the fluid delivery assembly 130 (e.g., to a patient P). For example, the drive assembly 140 can be releasably coupled to the fluid delivery assembly 130 to control delivery of fluid from the fluid delivery assembly 130 to provide continuous (e.g., non-pulsatile) fluid flow from the fluid delivery assembly 130. The drive assembly 140 can be the same or similar in structure and/or function to any of the drive assemblies described herein. The fluid delivery assembly 130 can be the same or similar in structure and/or function to any of the fluid delivery assemblies described herein.

The fluid delivery assembly 130 can be configured to be fluidically coupled to a fluid source 120 via a fluid line 133A (also referred to as a fluid inlet line, a tubing, inlet tubing, fluid inlet tubing, and/or a tube) such that fluid can be drawn from the fluid source 120. The fluid source 120 can include one or more fluid containers (e.g., fluid bags) containing, for example, saline or blood. In some embodiments, the fluid source 120 can be included in the fluid delivery assembly 130 and/or the system 100. The fluid delivery assembly 130 can also include a fluid line 133B (also referred to as a fluid outlet line, a tubing, inlet tubing, fluid inlet tubing, and/or a tube) couplable to a patient P such that fluid can be expelled by the fluid delivery assembly 130 to the patient. Each of the fluid line 133A and 133B can include or be coupled to any suitable fluid transfer component or combination of fluid transfer components such as tubing or tubes, catheters, fluid connectors, valves, filters, and the like.

Figure 1B:
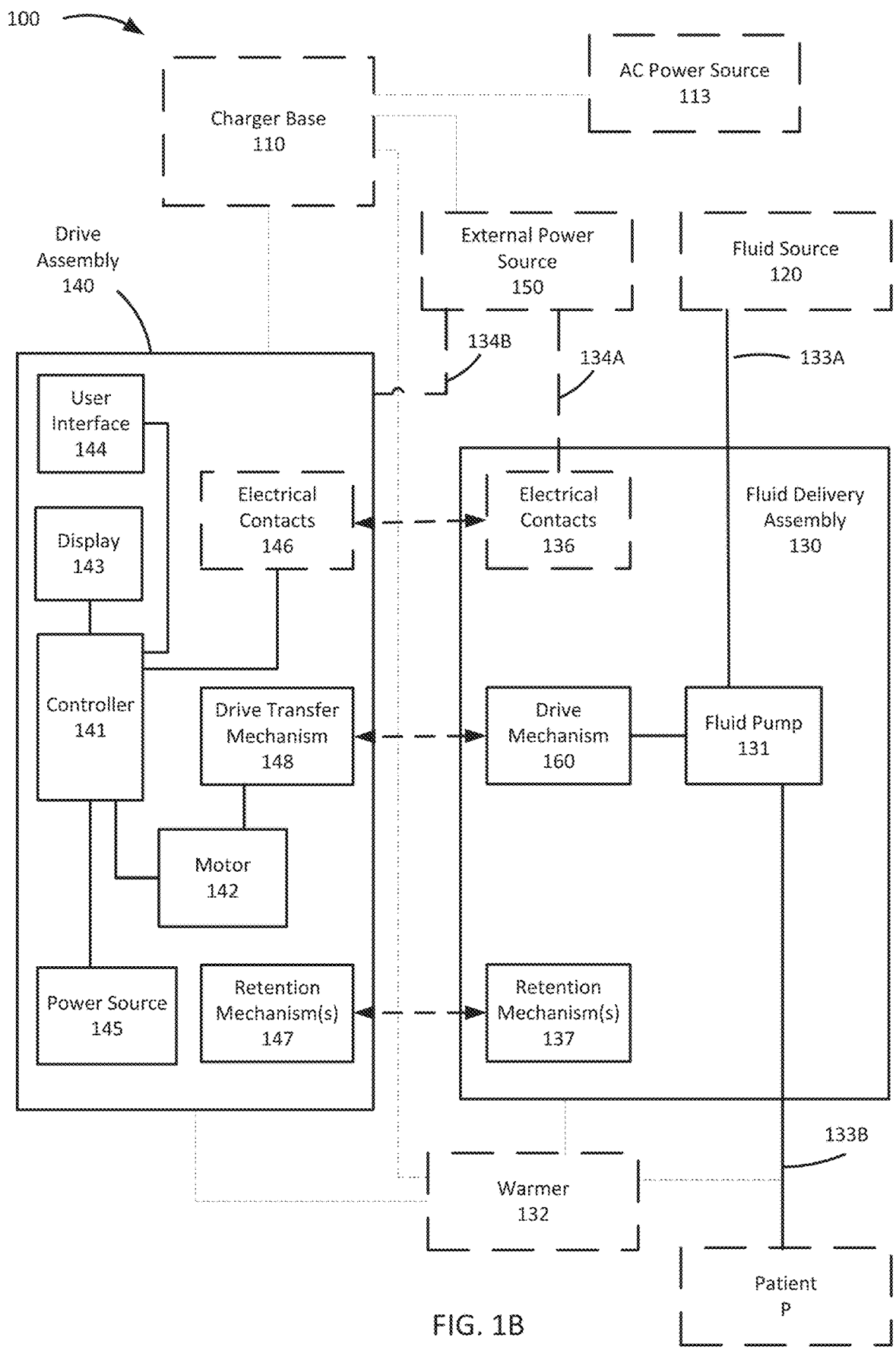
FIG. 1B is a schematic illustration of a system, according to an embodiment.

As shown in FIG. 1B, the fluid delivery assembly 130 can optionally include a drive mechanism 160 and a fluid pump 131. The fluid pump 131 can include one or more reservoirs (not shown). The drive mechanism 160 is configured to control the fluid pump 131 such that fluid can be drawn into the fluid pump 131 and expelled from the fluid pump 131. In some embodiments, the drive mechanism 160 can control the fluid pump 131 to produce substantially continuous flow from the fluid line 133B. The flow may be substantially non-pulsatile.

The fluid delivery assembly 130 can include a set of one-way check valves such that fluid can be drawn from the fluid source 120 into the fluid pump 131 but cannot be expelled from the fluid pump 131 toward the fluid source 120 via the fluid line 133A, and so that fluid can be expelled from the fluid pump 131 to the patient P via the fluid line 133B but not drawn from the fluid line 133B into the fluid pump 131. The check valves can be passive valve that do not require external input or control. Thus, fluid flow can be passively controlled, and fluid can flow only one direction through each check valve.

As shown in FIG. 1B, the drive assembly 140 includes a controller 141, a motor 142, and a drive transfer mechanism 148. The controller 141 is operably coupled to the motor 142 and configured to control the motor 142 to control movement of the drive transfer mechanism 148. The drive assembly 140 can also include a display 143, a user interface 144, and a power source 145 (also referred to as a power storage component or an internal power storage component). The display 143 can display information about the pumping operation, such as amount of fluid delivered and/or pressure of fluid delivered. The user interface 144 can allow the user to control fluid flow (e.g., initiation and ceasing of fluid infusion and for parameter adjustment such as flow rate). The power source 145 can include, for example, a battery (e.g., a rechargeable battery). In some embodiments, the user can set the amount of fluid to be delivered (e.g., via the user interface 144) as a predetermined infusion volume, and does not need to continually engage with the system 100 for the system 100 to continue delivering fluid (e.g., the user can set the drive assembly 140 and fluid delivery assembly 130 down and walk away during infusion). In some embodiments, the user interface 144 can include a button or trigger that is pressure responsive such that depressing the user interface 144 more causes the infusion rate to increase. In some embodiments, the infusion rate can be preset and does not change regardless of the pressure applied to the user interface 144 button or trigger.

The drive transfer mechanism 148 can be configured to engage (e.g., mechanically or magnetically) with the drive mechanism 160 (e.g., when the fluid delivery assembly 130 is coupled to the drive assembly 140) to control the drive mechanism 160 (and, thus, the operation of the fluid pump 131) under the control of the motor 142. The drive transfer mechanism 148 can include, for example, one or more drive shafts, one or more gears, and/or a reciprocating magnet. In some embodiments, the drive transfer mechanism 148 can include or be coupled to strain gauges, a torsion load cell, and/or other force sensing mechanisms (e.g., disposed on one or more shafts such as the one or more drive shafts) such that the controller can identify increases in resistance to rotation. In some embodiments, a drive shaft of the drive transfer mechanism 148 projects from a surface of the drive assembly 140 and is configured to be engaged with a pinion of the drive mechanism 160 of the fluid delivery assembly 130 (e.g., received within a drive shaft receptacle (e.g., an opening) of the pinion such that rotation of the drive shaft by the motor 142 causes rotation of the pinion).

As shown in FIG. 1B, the fluid delivery assembly 130 can include one or more retention mechanisms or features 137 and the drive assembly 140 can include one or more complementary retention mechanisms or features 147. The retention mechanism 137 and the retention mechanism 147 can be configured to mate or engage with each other to ensure that the fluid delivery assembly 130 and the drive assembly 140 are maintained in a coupled orientation relative to each other until the fluid delivery procedure has ended (e.g., to prevent accidental decoupling). The retention mechanism 137 and the retention mechanism 147 can include, for example, a mechanical latch and complementary detent, one or more magnetic connections, or any other suitable coupling mechanism(s). In some embodiments, the retention mechanism 137 and/or the retention mechanism 147 can include or also function as alignment features to ensure proper alignment between the fluid delivery assembly 130 and the drive assembly 140 for a fluid delivery procedure. In some embodiments, the system 100 can include separate alignment features (not shown) configured to encourage, urge, and/or maintain proper alignment between the fluid delivery assembly 130 and the drive assembly 140. In some embodiments, the retention mechanisms 137, 147 and/or the alignment features can include posts and receiving holes for the posts, projections and one or more receiving grooves for the projections, projections which trap a portion of the other assembly between the projections, or any other suitable features which prevent rotation of the fluid delivery assembly 130 relative to the drive assembly 140 when the drive transfer mechanism 148 is providing torque to the drive mechanism 160.

In some embodiments, the fluid delivery assembly 130 can be coupled to a warmer 132 (also referred to as a warmer assembly) via the fluid line 133B such that fluid delivered from the fluid delivery assembly 130 can be warmed (e.g., above a threshold temperature or to a temperature within a threshold temperature range) prior to and/or for delivery to the patient. In some embodiments, the warmer 132 can include a heating element and a heat exchanger. In some embodiments, the warmer 132 can include tubing (e.g., disposable tubing) that can be coupled to an end of the fluid line 133B such that fluid can flow from the fluid line 133B, into the tubing of the warmer 132, and away from a heating element and/or heat exchanger of the warmer toward or to the patient via the tubing of the warmer 132. In some embodiments, the fluid line 133B can be coupled to or engaged with the warmer 132 such that fluid traveling through the fluid line 133B can be heated by the warmer 132 while in the fluid line 133B prior to reaching a patient. In some embodiments, the warmer 132 can include a power source (also referred to as a power storage component), which can be, for example, a rechargeable battery. In some embodiments, in addition to or as an alternative to the power source, the warmer 132 can be configured to receive operational power and/or charging power for the power source via an electrical connection (e.g., between mating electrical contacts) with the drive assembly 140, the fluid delivery assembly 130, and/or an alternating current (AC) power source 113 such as a wall outlet. In some embodiments, the system 100 does not include the warmer 132. In some embodiments, any of the systems described herein can include or be coupled to a warmer such as the warmer 132. In some embodiments, the warmer 132 can be included in the fluid delivery assembly 130.

Optionally, as shown in FIG. 1B, the fluid delivery assembly 130 can include an electrical connection that includes electrical contacts 136 and the drive assembly 140 can include an electrical connection that includes electrical contacts 146 configured to be aligned with the electrical contacts 136 when the drive assembly 140 and the fluid delivery assembly 130 are coupled. The electrical contacts 136, 146 can include, for example, pogo pins and a plate, a pin configured to be received within a receptacle, and/or two metal plates configured to directly contact each other with or without a spring force. In some embodiments, the fluid delivery assembly 130 can be configured to provide operational power and/or charging power to the drive assembly 140 via the electrical contacts 136 and the electrical contacts 146. For example, the fluid delivery assembly 130 can be configured to be coupled to an external power source 150 via an electrical connection 134A such that power can be drawn from the power source 150 via the electrical connection 134A and delivered to the drive assembly 140 via the electrical contacts 136 and the electrical contacts 146. The power source 150 can include, for example, an AC power source (e.g., a wall outlet) and/or an external battery. Additionally, in some embodiments, data can be transferred between the fluid delivery assembly 130 and the drive assembly 140 via the electrical contacts 136 and the electrical contacts 146 such that, for example, identification information can be received by the drive assembly 140 and used to determine, for example, motor speed based on pumping parameters associated with the identification information. In some embodiments, the power source 150 can be configured to be coupled to the drive assembly 140 and configured to provide operational power and/or charging power to the drive assembly 140. For example, the power source 150 can be coupled to the drive assembly 140 (e.g., to the electrical contacts 146 and/or to the power source 145) via an electrical connection 134B. In some embodiments, the power source 150 can be configured to be coupled to the warmer 132 via an electrical connection (not shown) and/or via the drive assembly 140 and/or the fluid delivery assembly 130. The electrical connections described herein can be any suitable electrical coupling, such as an electrical contact, wire, and/or power cord. In some embodiments described herein, although an electrical connection between two components or assemblies may be described as including mating electrical contacts or a power cord configured to be coupled to a receiving plug, the systems and assemblies described herein can include any suitable mating electrical connection components capable of achieving the power transfer and/or data transfer functions described. In some embodiments, the power source 150 can include a charger base 110 (also referred to as a charger base assembly, a charger assembly, a charger, or a base assembly) configured to be electrically and mechanically coupled to the fluid delivery assembly 130, the drive assembly 140, and/or the warmer 132 such that charging power and/or operational power can be provided to the drive assembly 140 (e.g., the power source 145) and/or the warmer 132 (e.g., an internal power storage component of the warmer 132). The charger base 110 can be coupled to the AC power source 113 (e.g., a wall outlet) to increase a stored power level of a power source (also referred to as an internal power storage component) included in the charger base 110 via an electrical connection (e.g., a plug). The charger base 110 can also include electrical contacts and/or an electrical connection such as an elongated wire or plug configured to electrically couple the power source included in the charger base 110 with the drive assembly 140 and/or the warmer 132 to provide power from the power source in the charger base 110 to the drive assembly 140 and/or the warmer 132 (e.g., during and/or prior to use of the system 100). Although described as a "charger base," in some embodiments, such as any of the embodiments described herein, the charger base 110 can be operable to provide (and any of the drive assemblies or warmer assemblies can be configured to receive and operate based on) operational power, rather than or in addition to charging power. For example, the charger base 110 can provide operational power to any of the drive assemblies or warmer assemblies described herein that may bypass an internal power storage device (e.g., a chargeable power storage device configured to provide operational power when the drive assembly 140 and/or warmer 132 is not coupled to the charger base 110) of any of the drive assemblies or warmer assemblies described herein.

In use, the fluid delivery assembly 130 can be coupled to the drive assembly 140 such that the drive transfer mechanism 148 and the drive mechanism 160 are operably coupled. In some embodiments, the fluid delivery assembly 130 can be coupled to the drive assembly 140 such that the electrical contacts 136 are aligned with the electrical contacts 146 and/or such that the retention mechanism 137 is engaged with the retention mechanism 147. The fluid line 133A can be fluidically coupled to a fluid source 120 (e.g., via a fluid connector such as an IV tubing spike) and can be fluidically coupled to one or more blood filters and/or chambers disposed in line with the fluid source 120 and the fluid line 133A. The fluid line 133B can be fluidically coupled to a patient (e.g., a patient's vasculature) via, for example, a luer lock connector attached to a patient's IV access. The drive assembly 140 can then initiate operation of the motor 142 (under control of the user via the user interface 144) such that the fluid pump 131 operates to dispense fluid via the fluid line 133B. In some embodiments, some or all of the components of the system 100 can be included in a kit, such as a kit including a box or bag and including any suitable number of fluid (e.g., blood or saline) bags and the components or a subset of the components of the system 100.

In some embodiments, the fluid delivery assembly 130 can include a fluid delivery assembly housing and the drive assembly 140 can include a drive assembly housing. The fluid delivery assembly housing can define an interior space within which the fluid pump 131 and at least a portion of the drive mechanism 160 can be disposed. In some embodiments, the fluid delivery assembly housing can enclose the fluid pump 131 and at least a portion of the drive mechanism, defining openings through which the inlet fluid line 133A and the outlet fluid line 133B can pass and an opening for engagement between the drive mechanism 160 and the drive transfer mechanism 148. The electrical contacts 136 and retention mechanism(s) 137 can be disposed on or coupled to an outer surface of the fluid delivery assembly housing. The fluid delivery assembly housing can also optionally define an aperture configured to receive an alignment feature (e.g., a peg) coupled to the drive assembly housing, or vice versa. The drive assembly housing can define an interior space within which the controller 141, motor 142, power source 145, and at least a portion of the drive transfer mechanism 148 can be disposed. In some embodiments, the drive assembly housing can enclose the controller 141, the power source 145, the motor 142, and at least a portion of the drive transfer mechanism 148, and can define an opening through which the drive transfer mechanism 148 can engage with the drive mechanism 160. The electrical contacts 146 and retention mechanism(s) 147 can be disposed on or coupled to an outer surface of the drive assembly housing.

In some embodiments, the fluid delivery assembly housing and the drive assembly housing can be shaped and sized such that, when the drive assembly 140 and the fluid delivery assembly 130 are properly coupled for a pumping operation (e.g., the drive mechanism 160 is engaged with the drive transfer mechanism 148 and any electrical contacts and/or retention mechanisms are properly engaged), a surface of the fluid delivery assembly housing abuts a surface of the drive assembly housing (e.g., the surfaces through which the drive mechanism 160 and the drive transfer mechanism 148 engage). In some embodiments, the electrical contacts 136 and 146 are disposed on respective abutting surfaces of the fluid delivery assembly housing and the drive assembly housing. In some embodiments, the respective abutting surfaces can have substantially the same perimeter, shape, size, and/or surface area. For example, each of the abutting surfaces can be disposed within a plane parallel to the plane within which the other abutting surface is disposed, and the abutting surfaces can have the same length and width. In some embodiments, the abutting surfaces are rectangular, circular, ovular, square, or any other suitable shape. In some embodiments, the abutting surface of the drive assembly 140 is an upper surface or uppermost surface of the drive assembly 140 and the abutting surface of the fluid delivery assembly 130 is a lower surface or lower most surface of the drive assembly. In some embodiments, the fluid delivery assembly housing includes parallel upper and lower surfaces. In some embodiments, the drive assembly housing includes parallel upper and lower surfaces. Thus, in some embodiments, each of the drive assembly housing and the fluid delivery assembly housing can have a substantially box-like or disc-like shape that, when coupled together, becomes a layered, combined housing that is taller than when separated, but has the same footprint (e.g., length and width) and coplanar sidewalls. In some embodiments, the external power source 150 can also include an external power source housing and can have a surface configured to abut a surface of the drive assembly housing in a power transfer configuration in which the drive assembly 140 is electrically coupled to the external power source 150 (e.g., via electrical connection 134B), and the abutting surfaces of the drive assembly housing and the external power source housing can have substantially the same perimeter, shape, size, and/or surface area. In some embodiments, the external power source housing includes parallel upper and lower surfaces. Thus, in some embodiments, each of the drive assembly housing and the external power source housing can have a substantially box-like or disc-like shape that, when coupled together, becomes a layered, combined housing that is taller than when separated, but has the same footprint (e.g., length and width) and coplanar sidewalls. In some embodiments, all three of the drive assembly housing, the fluid delivery assembly housing, and the external power source housing can have complementary abutting surfaces having the same perimeter as described above and can have a substantially box-like or disc-like shape that, when coupled together, the three housing form a layered, combined housing that is taller than when separated, but has the same footprint (e.g., length and width) and coplanar sidewalls (see, for example, system 3900 shown in FIGS. 43A-43C). In some embodiments, the warmer 132 can also include a warmer housing having a surface configured to abut with the upper surface of the fluid delivery assembly such that the warmer can be stacked with the fluid delivery assembly 130, the drive assembly, and/or the external power source 150. In some embodiments, the warmer 132 can also have the same or a similar footprint to the other housings. In some embodiments, rather than the upper and lower surfaces of the housings of the system 100 being configured to be coupled together as described, each of the housings includes side surfaces configured to be coupled together in abutting relationships as described. In some embodiments, one or more of the housings of the system 100 can be retained together via any retentions mechanisms 137 described herein such as latches, elastic bands, straps, and/or any other suitable releasable retention mechanisms. In some embodiments, the system 100 can include a carrying case or other container (e.g., a container having a lid, handle, and/or hook for hanging the container near a patient) configured to receive one or more of the housings of the system 100 and retain two or more of the housings in their coupled, abutting configuration during an infusion operation of the system 100. In some embodiments, the charger base 110 can be configured to define an interior space configured to receive one or more of the housings of the system 100 and retain them in their coupled, abutting configuration during an infusion operation of the system 100 (e.g., while in electrical contact with one or more of the assemblies including the housings).

Figure 2:
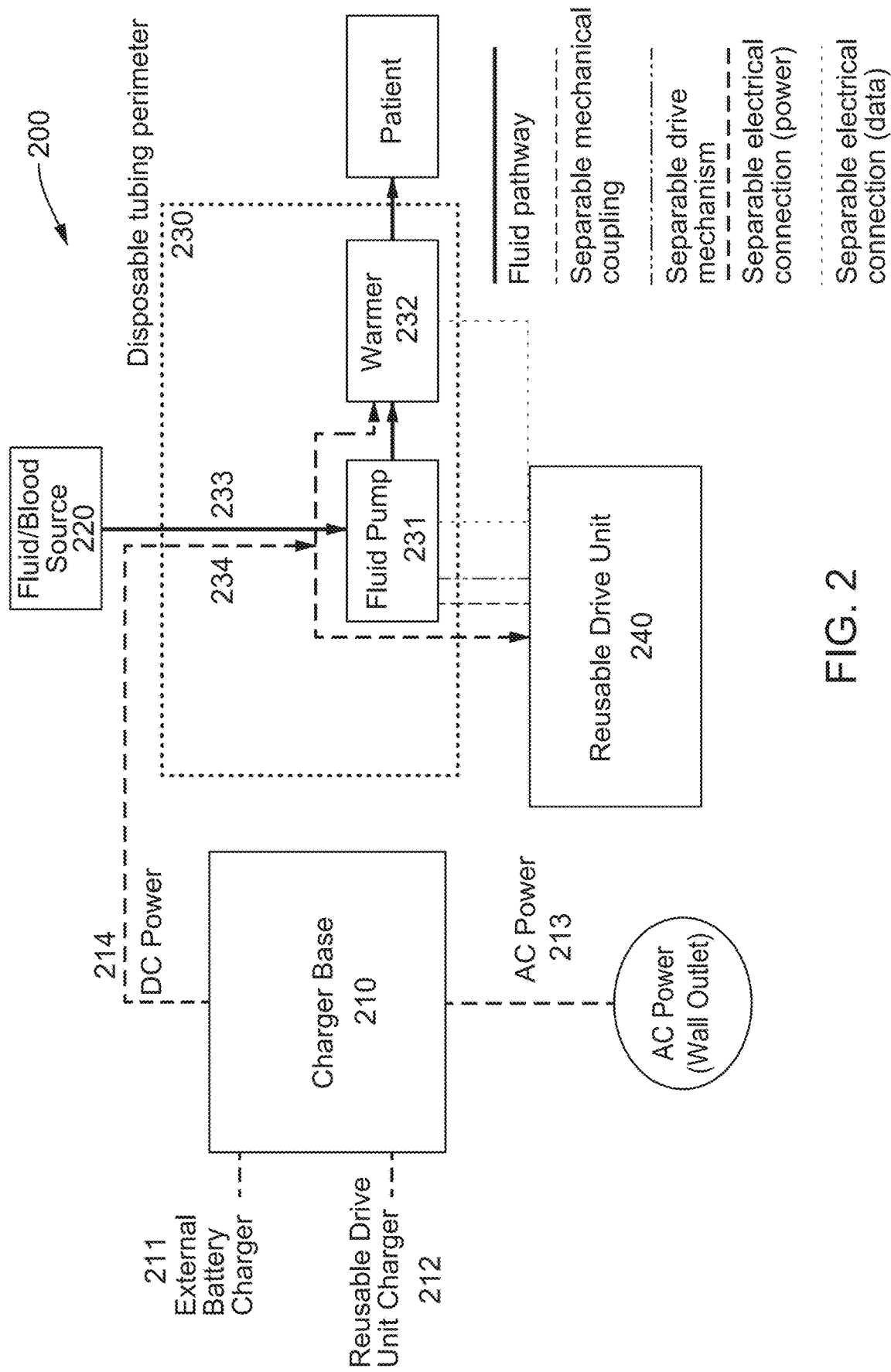
FIG. 2 is a schematic illustration of a system, according to an embodiment.

FIG. 2 is a schematic illustration of a system 200. The system 200 can be the same or similar in structure and/or function to any of the systems described herein, such as the system 100. The system 200 includes a reusable drive unit 240, a disposable tubing assembly 230, and a charger base 210. The disposable tubing assembly 230 includes a fluid pump 231 and a warmer 232 (also referred to as a warmer assembly). The fluid pump 231 is configured to be fluidically coupled to a fluid source 220 (e.g., a blood or saline source) such that, under the control of the reusable drive unit 240, the fluid pump 231 can draw fluid from the fluid source 220 via a fluid line 233 and deliver the fluid to a patient via the warmer 232. The disposable tubing assembly 230 is configured to be releasably mechanically and electrically coupled to the reusable drive unit 240. When the disposable tubing assembly 230 is releasably coupled to the reusable drive unit 240, the reusable drive unit 240 can drive (e.g., mechanically) the fluid pump 231 to draw fluid from the fluid source 220 and deliver fluid to the patient via the warmer 232. In some embodiments, the disposable tubing assembly 230 can provide electrical operational power and/or charging power to the reusable drive unit 240 and/or the warmer 232. The fluid pump 231 and/or the warmer 232 are also configured to be electrically coupled to the reusable drive unit 240 such that data can be transferred between the reusable drive unit 240 and the fluid pump 231 and/or the warmer 232. In some embodiments, the system 200 does not include the warmer 232.

As shown in FIG. 2, the charger base 210 can be configured to be electrically coupled to a source of AC power (e.g., via a wall outlet) via an electrical connection 213. The charger base 210 can be configured to provide DC power 214 to the reusable drive unit 240 via the disposable tubing assembly 230 (e.g., via an electrical connection of the disposable tubing assembly 230). The charger base 210 can include an external battery charger 211 and a reusable drive unit charger 212. Thus, in some configurations, the reusable drive unit 240 can be coupled directly to the reusable drive unit charger 212 (e.g., when not in use during an infusion operation) such that the reusable drive unit 240 can be charged by the charger base 210 (e.g., a power storage supply of the reusable drive unit 240 can be increased) with sufficient operational power for an infusion operation (e.g., to drive the fluid pump 231). In some embodiments, the reusable drive unit 240 can provide operational power to the warmer 232. Additionally, in some configurations, the external battery charger 211 of the charger base 210 can charge an external battery (not shown) included in or coupled to the disposable tubing assembly 230 (e.g., when the external battery is coupled to the external battery charger 211) such that the disposable tubing assembly 230 can provide operational power and/or charging power to the reusable drive unit 240 and/or the warmer 232.

In the configuration of the system 200 shown in FIG. 2, the system 200 can be used, for example, in an environment in which AC power is readily available (e.g., via a wall outlet) to power the system, such as a hospital. As shown, the charger base 210 can include an electrical connection 214 that can be electrically coupled to an electrical connection 234 of the disposable tubing assembly 230 such that AC power can be drawn from the AC power source 213 by the charger base 210, and the charger base 210 can provide DC power to the reusable drive unit 240 via the electrical connection 214, the electrical connection 234, and the fluid pump 231. As shown in FIG. 2, DC power can also be provided from the charger base to the warmer 232 via the electrical connection 214 and the electrical connection 234. The electrical connection 214 can include, for example, an elongated cable (also referred to as a cord or supply cord), wire, contact(s) and/or any other suitable electrical connection components.

Figure 3:
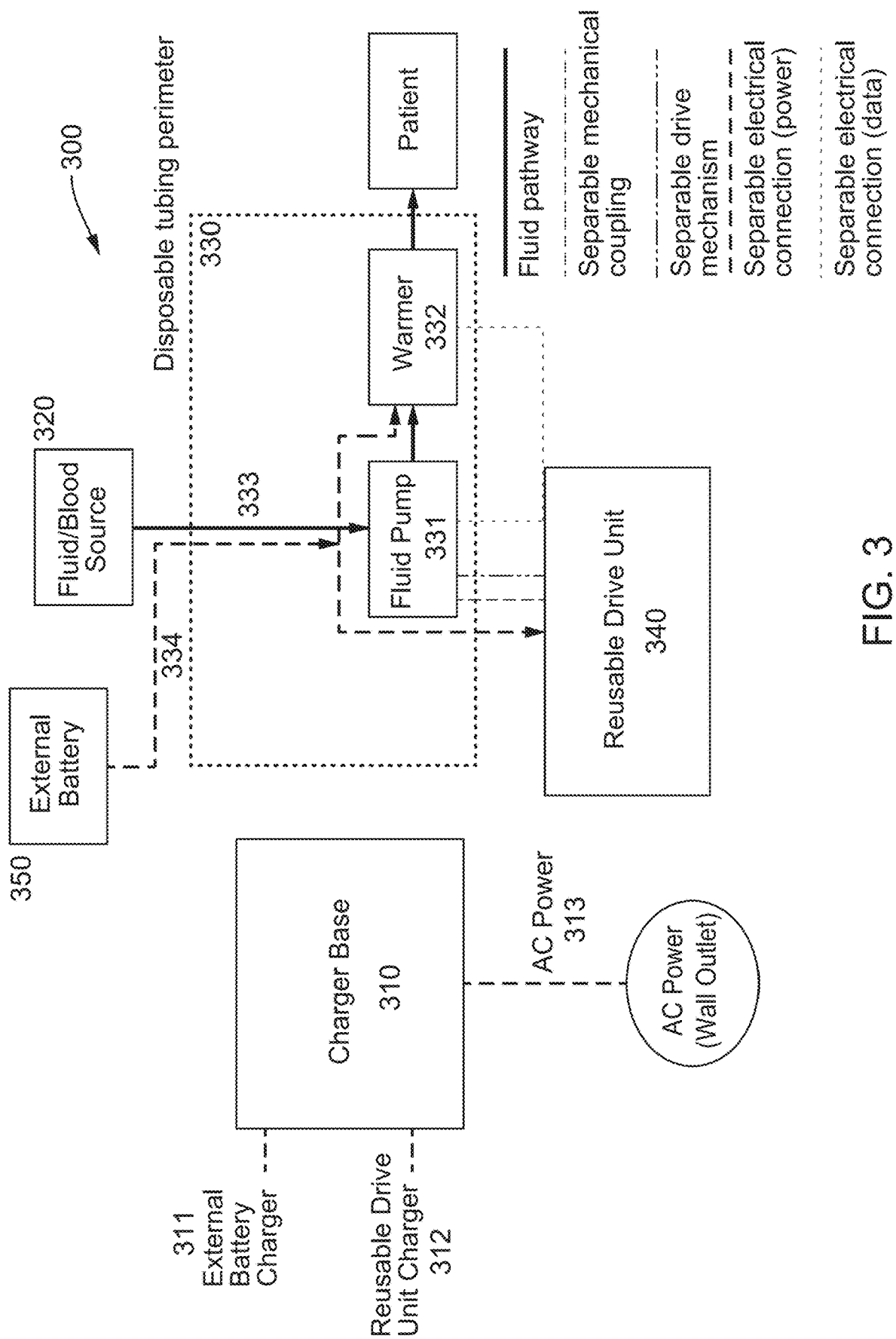
FIG. 3 is a schematic illustration of a system, according to an embodiment.

FIG. 3 is a schematic illustration of a system 300. The system 300 can be the same or similar in structure and/or function to the system 200. For example, the system 300 includes a reusable drive unit 340, a disposable tubing assembly 330, and a charger base 310 that can be the same or similar in structure and/or function to the reusable drive unit 240, the disposable tubing assembly 230, and the charger base 210 described above. In some embodiments, the system 300 can be the same system as the system 200, but arranged in a portable use configuration as shown in FIG. 3. The system 300 can be used, for example, in an environment in which AC power is not readily available, such as during transit to a hospital, or in an environment in which a user (e.g., a physician, EMT, or nurse) prefers to have greater mobility than permitted if the reusable drive unit 240 is attached to a wall outlet. As shown in FIG. 3, the disposable tubing assembly 330 can be coupled to an external battery 350 such that operational power and/or charging power can be provided from the external battery 350 to the reusable drive unit 340 and the warmer 332 via electrical connection 334 (which may be the same or similar in structure and/or function to electrical connection 234 described above with respect to the disposable tubing assembly 230). When needed, the external battery 350 can be charged via electrical engagement with the external battery charger 311 of the charger base 310.

Figure 4:
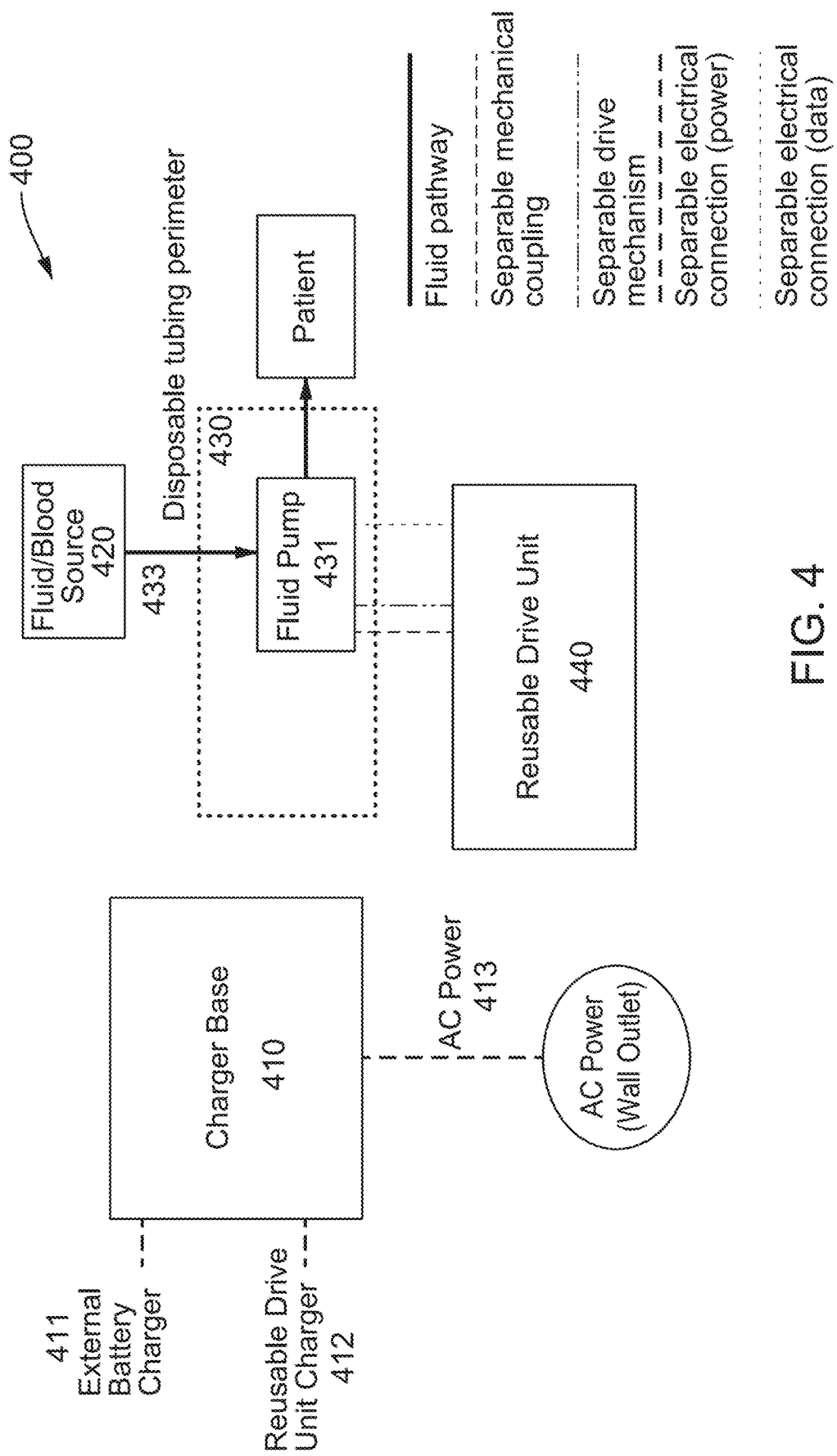
FIG. 4 is a schematic illustration of a system, according to an embodiment.

FIG. 4 is a schematic illustration of a system 400. The system 400 can be the same or similar in structure and/or function to the system 200 and/or the system 300. For example, the system 400 includes a reusable drive unit 440, a disposable tubing assembly 430, and a charger base 410 that can be the same or similar in structure and/or function to the reusable drive unit 240, the disposable tubing assembly 230, and the charger base 210 described above. As shown in FIG. 4, the system 400 does not include a warmer on the fluid line to the patient. Also as shown in FIG. 4, the reusable drive unit 440 can be configured to operate to control operation of the fluid pump 431 based on power stored in an internal power supply (not shown). As shown, the charger base 410 can include an electrical connection 412 (also referred to as a reusable drive unit charger) that can be electrically coupled to an electrical connection (not shown) of the reusable drive unit 440 such that AC power can be drawn from the AC power source 413 by the charger base 410, and the charger base 410 can provide DC power to the reusable drive unit 440 via the electrical connection 412 and the electrical connection of the reusable drive unit 440. Thus, the power level of the internal power supply of the reusable drive unit 440 can be increased by coupling the reusable drive unit 440 to the electrical connection 412 of the charger base 410 (e.g., via mating electrical contacts). The charger base 410 can also include an electrical connection 411 (also referred to as an external battery charger) that can be electrically coupled to an electrical connection of an external battery (not shown) (such as the external battery 350 shown in FIG. 3) such that AC power can be drawn from the AC power source 413 by the charger base 410, and the charger base 410 can provide DC power to the external battery via the electrical connection 411.

Figure 5:
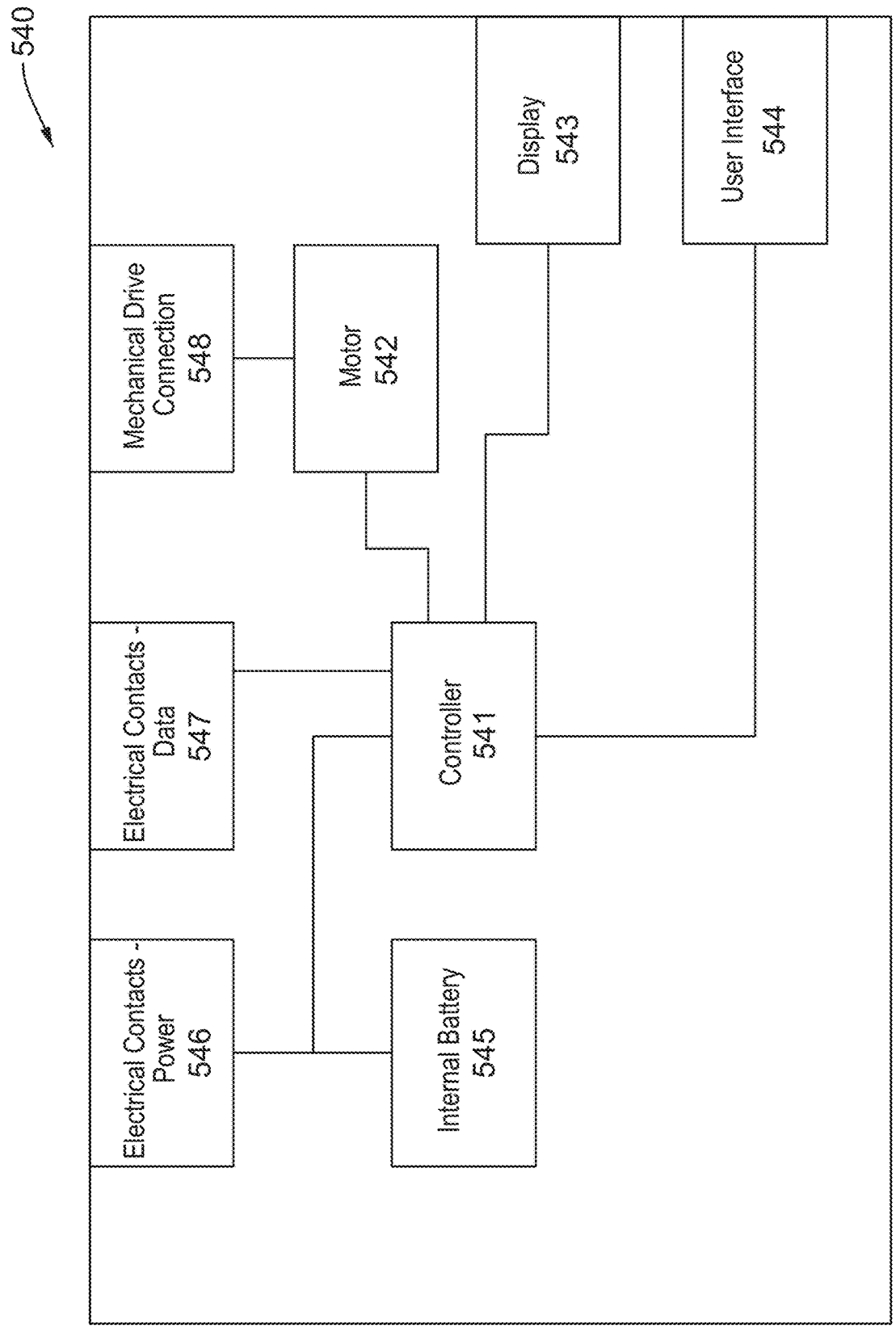
FIG. 5 is a schematic illustration of drive assembly, according to an embodiment.

FIG. 5 is a schematic illustration of a reusable drive unit 540 (also referred to as a drive assembly), which can be the same or similar in structure and/or function to any of the reusable drive units described herein (e.g., the reusable drive unit 140, the reusable drive unit 240, the reusable drive unit 340, and/or the reusable drive unit 440). The reusable drive unit 540 can be formed as a small, portable (e.g., handheld) device. The reusable drive unit 540 can include a controller 541, a motor 542, a display 543, a user interface 544, an internal power storage component 545 (also referred to as an internal battery), a mechanical drive connection 548 (also referred to as a drive transfer mechanism), one or more electrical contacts 546 for transferring power, and one or more electrical contacts 547 for transferring data.

The motor 542 can be configured to drive a fluid pump of a disposable tubing assembly, such as any of the fluid pumps described herein (e.g., the fluid pump 131, the fluid pump 231, the fluid pump 331, and/or the fluid pump 431). In some embodiments, for example, the motor 542 can drive a fluid pump at pressures greater than 300 mmHg. The controller 541 can be configured to electronically control the fluid pump coupled to the reusable drive unit 540 and warming functions of a warmer (such as any of the warmers described herein) coupled to the reusable drive unit 540. The mechanical drive connection 548 can be configured to reversibly connect the motor 542 to the fluid pump of the disposable tubing assembly.

The internal battery 545 can be configured to receive power from an external power source reversibly electrically coupled to the one or more electrical contacts 546 such that a power storage level of the internal battery 545 increases. In some embodiments, the internal battery 545 and the one or more electrical contacts 546 can be configured to provide power to a warmer reversibly electrically coupled to the one or more electrical contacts 546. The controller 541 can be configured to communicate with a disposable tubing assembly (e.g., sensors included in a disposable tubing assembly such as any of the disposable tubing assemblies described herein) via the electrical contacts 547 (e.g., by receiving data via the electrical contacts 547). In some embodiments, the sensors can include, for example, thermocouples, other temperature sensing devices, and/or pressure sensors configured to detect fluid pressure in inlet and/or outlet tubing of the disposable tubing assembly. In some embodiments, the user interface 544 can be configured to allow a user to control fluid flow and/or warming parameters (e.g., allow for initiation and ceasing of fluid infusion and for parameter adjustment such as flow rate and temperature via controlling speed of the motor 542 and operation of a warmer, respectively).

Figure 6:
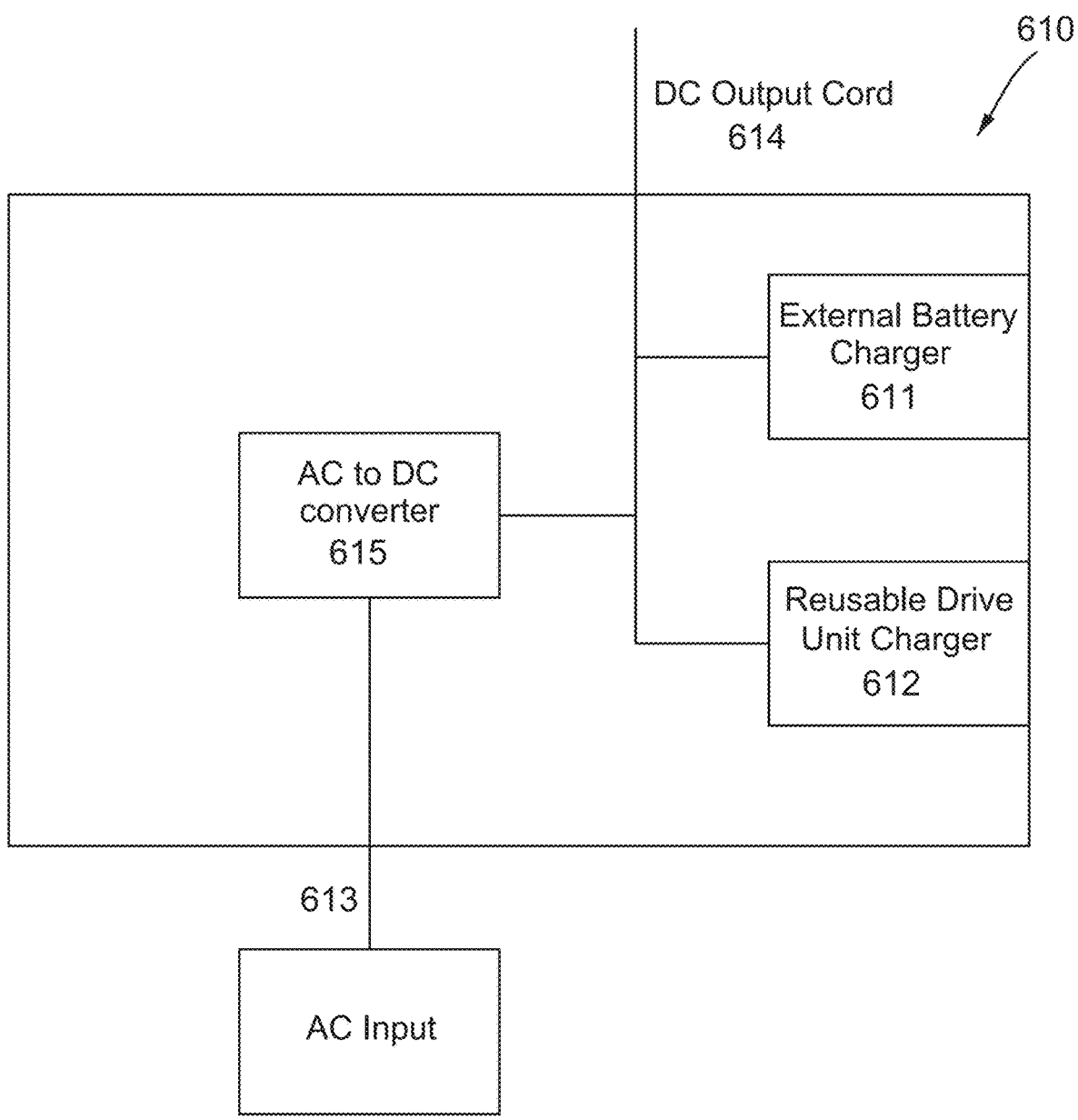
FIG. 6 is a schematic illustration of a charger base, according to an embodiment.

FIG. 6 is a schematic illustration of a charger base 610, which can be same or similar in structure and/or function to any of the charger bases described herein (e.g., the charger base 110, the charger base 210, the charger base 310, and/or the charger base 410). As shown in FIG. 6, the charger base 610 includes an AC to DC converter 615, an external battery charger 611, and a reusable driver unit charger 612. The charger base 610 can receive an AC input via an electrical connection 613 and provide a DC output via an electrical connection 614 (also referred to as a DC output cord). Each of the external battery charger 611 and the reusable drive unit charger 612 can include, for example, electrical contacts configured to be reversibly electrically coupled to any of the external power sources and reusable drive units, respectively, described herein.

Figure 7:
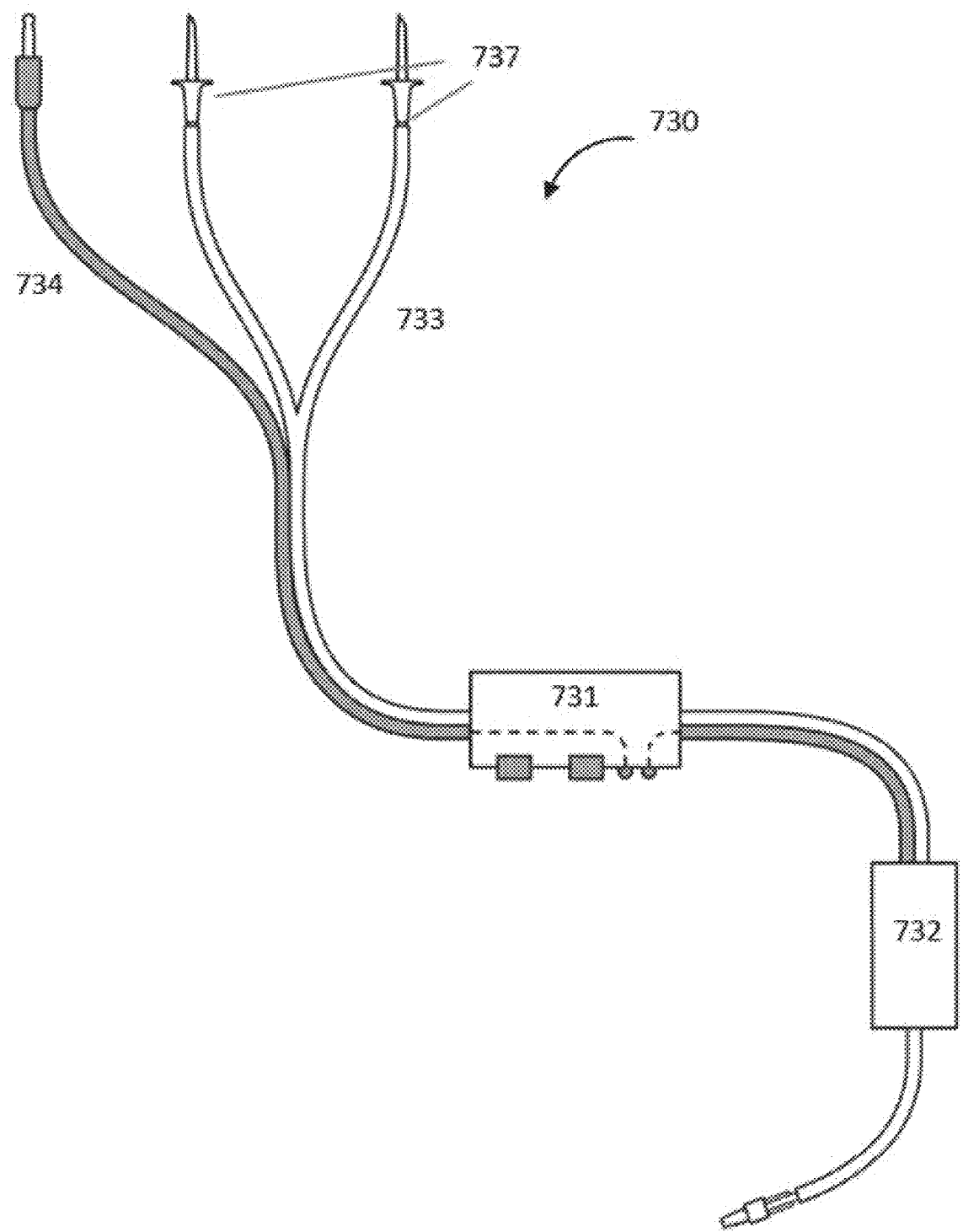
FIG. 7 is a schematic illustration of a fluid delivery assembly, according to an embodiment.

FIG. 7 is a schematic illustration of a disposing tubing assembly 730, which can be same or similar in structure and/or function to any of the disposing tubing assemblies described herein (e.g., the disposing tubing assembly 130, the disposing tubing assembly 230, the disposing tubing assembly 330, and/or the disposing tubing assembly 430). The disposable tubing assembly 730 can define a fluid path from a fluid source (e.g., a fluid container containing a fluid), through a fluid pump 731, to a patient. The fluid path can be at least partially defined by tubing 733. The disposable tubing assembly 730 can include, for example, at least one spike 737 coupled to the tubing 733. Each spike 737 can be configured to puncture a fluid container (e.g., containing a fluid such as blood or saline) to create a fluid connection between the spike 737 and the fluid container. The disposable tubing assembly 730 can optionally include at least one fluid warmer 732, which can, for example, heat fluid by converting electrical energy to thermal energy. The warmer 732 can be the same or similar in structure and/or function to any of the warmers described herein.

Optionally, the disposable tubing assembly 730 can include an integrated power supply cord 734 (also referred to as an elongated cable). The integrated power supply cord 734 can include or form a first electrical connection (e.g., near the spike(s) 737) which is configured to be connected to an external power source, such as any of the external power sources described herein (e.g., external battery 350 described above) and/or a DC power supply cord such as any of the power supply cords described herein (e.g., DC power supply cord 214 described above). The disposable tubing assembly 730 optionally includes a second electrical connection which is configured to reversibly connect to a reusable drive unit (e.g., the reusable drive unit 240 described above or any of the reusable drive units described herein) and a third electrical connection coupled to a warmer 732 included in or coupled to the disposable tubing assembly 730.

The fluid pump 731 can optionally be configured to pump fluid at a pressure greater than about 300 mmHg (~6 psi). In some embodiments, the upper limit of the pressure of the fluid pumped by the fluid pump 731 is about 100 psi. In some embodiments, the fluid pump 731 includes at least two syringe bodies. In some embodiments, the fluid pump 731 includes at least two one-way check valves such that fluid is prevented from flowing from the patient and/or the fluid pump 731 to the spikes 737 and always flows from the spikes 737 to the patient regardless of position of the fluid pump 731 (e.g., regardless of syringe plunger position and/or direction of travel). In some embodiments, the tubing 733 can include nearly constant diameter tubing coupling the spikes 737 to the fluid pump 731 and coupling the fluid pump 731 to the patient (e.g., via the warmer 732). In some embodiments, the tubing 733 can include smooth (e.g., tapered) transitions between diameter changes. In some embodiments, the tubing 733 can include at least one section of compliant tubing which can expand under transient pressure spikes (e.g., to minimize hemolysis). Optionally, a distal air filter (not shown) can be included in or coupled to the disposable tubing assembly 730 and disposed between the fluid pump 731 and the patient (e.g., between the warmer 732 and the patient).

As shown in FIG. 7, a portion of the length of the power supply cord 734 is coupled to a portion of the length of the tubing 733 such that the portion of the power supply cord 734 extends parallel to the portion of the length of the tubing 733. As shown, the portion of the tubing 733 can be fluid inlet tubing and the power supply cord 734 and the tubing 733 can be coupled together from the fluid pump 731 to a location on each of the power supply cord 734 and the tubing 733 a distance from the fluid pump 731 (e.g., a location near a fluid source or external power source to which the tubing 733 and the power supply cord 734 are coupled, respectively). For example, the power supply cord 734 and the tubing 733 can be coupled together from the fluid pump 731 to a location more than halfway or three-quarters the length of the power supply cord 734 and/or the tubing 733.

Figure 8:
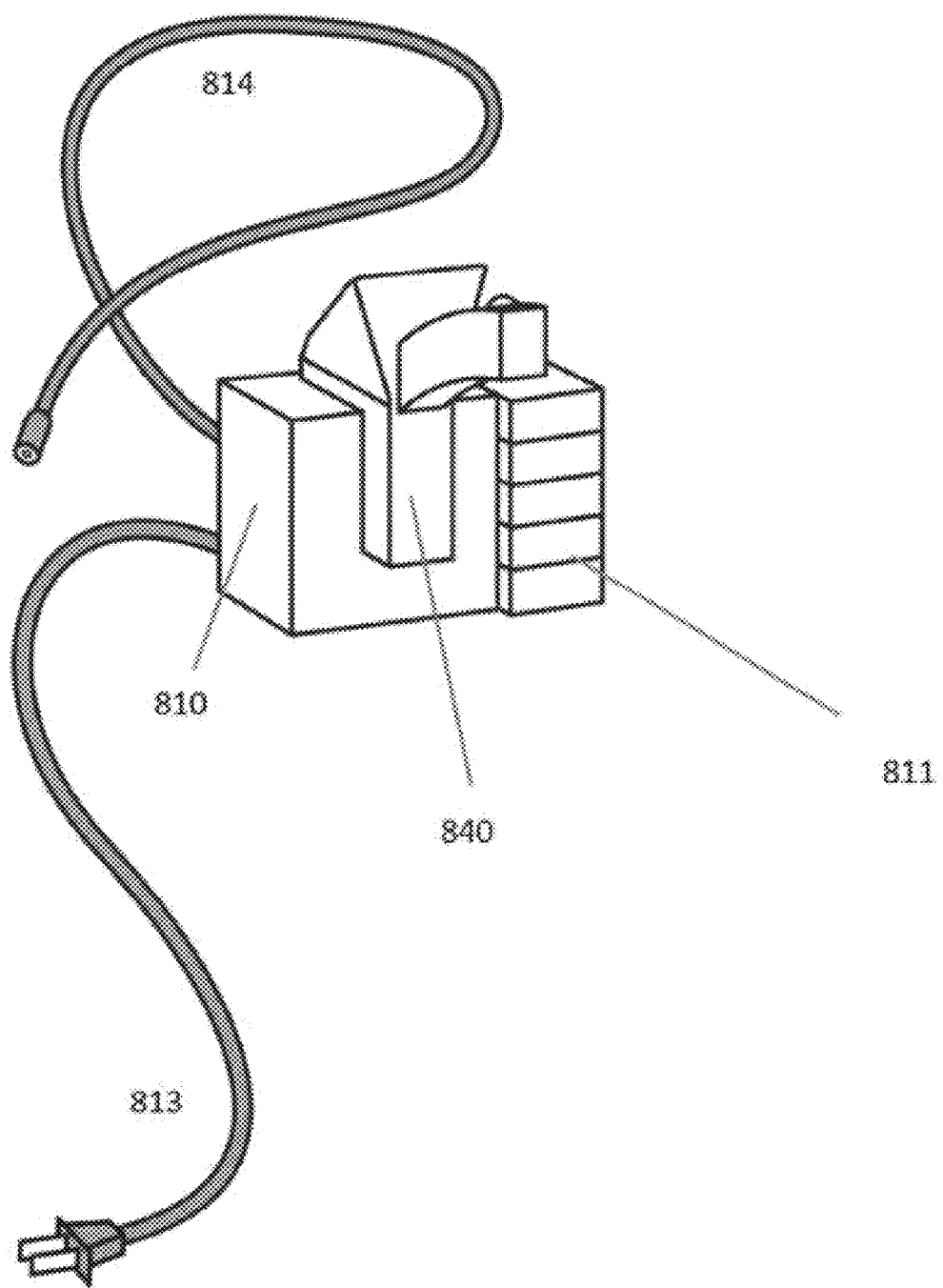
FIG. 8 is a schematic illustration of a charger base, according to an embodiment.

FIG. 8 is a schematic illustration of a charger base 810, which can be similar in structure and/or function to any of the charger bases described herein (e.g., the charger base 110, the charger base 210, the charger base 310, the charger base 410, and/or the charger base 610). The charger base 810 can be a physical support and electrical charging station. The charger base 810 can include a power cord 813 and a direct current (DC) output cord 814. Additionally, the charger base 810 can include an AC to DC converter (not shown) (e.g., AC to DC converter 615 described above). The power cord 813 can couple the charging base 810 to a source of AC power (e.g., an AC wall outlet). The DC output cord 814 can be configured to be coupled to a disposable tubing assembly such as any of the disposable tubing assemblies described herein (e.g., the disposable tubing assembly 730) to provide power to a warmer and/or to a reusable drive unit via the disposable tubing assembly.

The charger base 810 can include a physical dock including a receptacle configured to receive and support a reusable drive unit 840, which can be the same or similar in structure and/or function to any of the reusable drive units described herein. The physical dock can be configured to electrically and mechanically connect the reusable drive unit 840 to the AC to DC converter and/or to an internal power storage component of the charger base 810 such that an internal power storage component of the reusable drive unit 840 can be charged (e.g., a power storage level of the internal power storage component of the reusable drive unit 840 can be increased). The physical dock can also be configured to mechanically support and electrically connect an external battery 811, which can be the same or similar in structure and/or function to any of the external power sources described herein, to the AC to DC converter and/or to the internal power storage component of the charger base 810 such that the external battery 811 can be charged (e.g., a power storage level of the external battery 811 can be increased). The external battery 811 can be electrically and mechanically coupled to a disposable tubing assembly such as the disposable tubing assembly 730 while docked with the charger base 810 and/or after being decoupled form the charger base 810 to provide power to the disposable tubing assembly.

As described above with respect to FIGS. 2-4, any of the systems described herein can be used in a variety of (e.g., three) different use scenarios, each having a unique use configuration. Three example use scenarios include an AC power-based use scenario (e.g., for stationary hospital use), a portable power supply-based (e.g., battery-based) use scenario (e.g., for portable use within or outside of a hospital environment, such as while traveling between locations), and an infusion-only, no warming use scenario.

Figure 9:
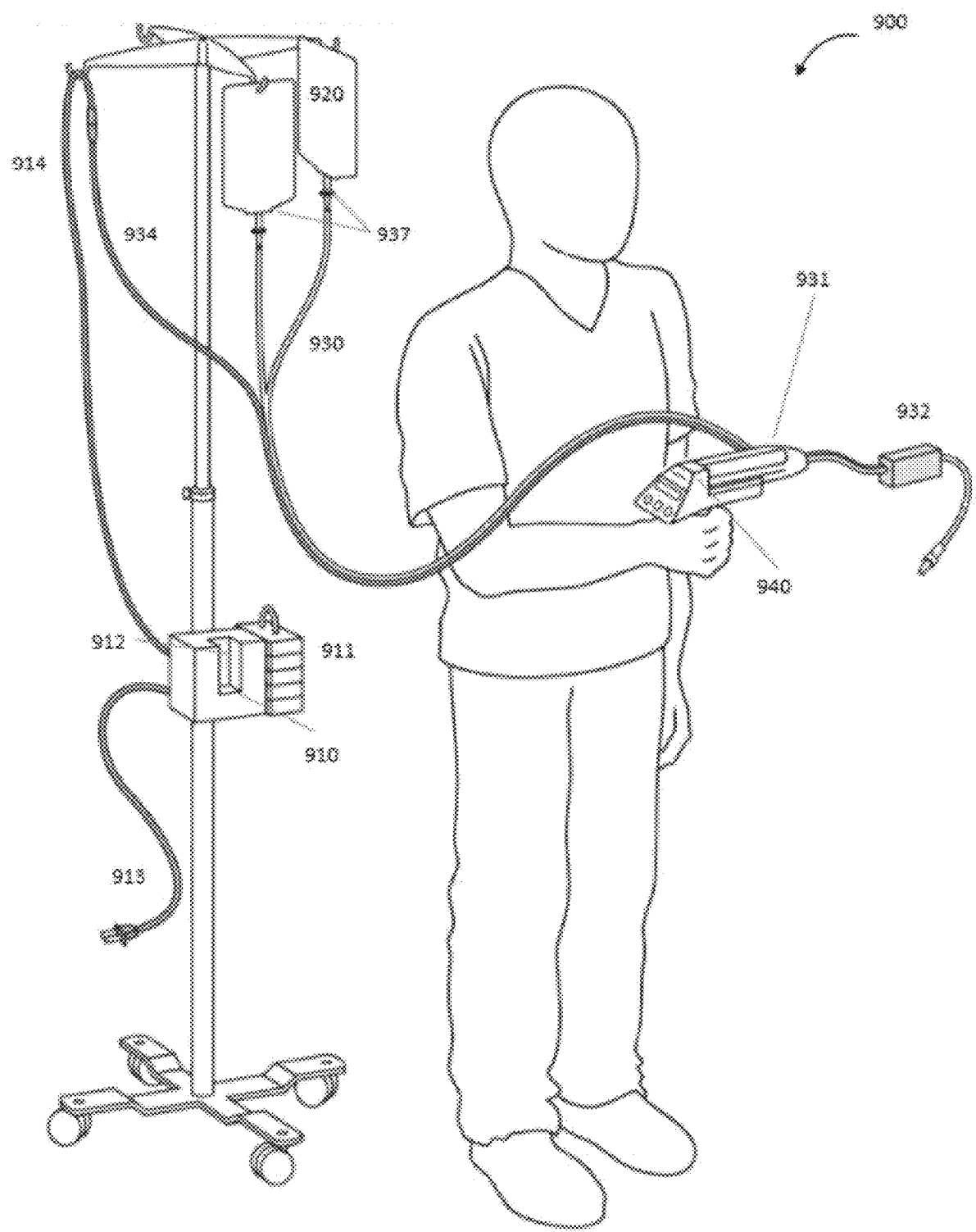
FIG. 9 is a schematic illustration of a charger base, according to an embodiment.

For example, FIG. 9 is a schematic illustration of a system 900 in a first use configuration (e.g., a configuration in which AC power can be drawn from an AC power supply such as an AC wall outlet to power operation of a reusable drive unit 940 of the system 900, such as in a hospital environment). The system 900 can be the same or similar in structure and/or function to any of the systems described herein, such as the system 200. For example, the system 900 can include a disposable tubing assembly 930, the reusable drive unit 940, and a charger base 910. The disposable tubing assembly 930 can include a fluid pump 931, a warmer 932, and spikes 937 configured to fluidically couple tubing of the disposable tubing assembly 930 with fluid sources 920 (e.g., sources of any suitable fluid such as saline, fluid including crystalloids such as 0.9% sodium chloride, blood, and/or blood products). The disposable tubing assembly 930 also includes a power supply cord 934. The charger base 910 includes a power cord 913 configured to couple the charging base 910 to a source of AC power (e.g., an AC wall outlet) and a DC output cord 914 configured to be coupled to the power supply cord 934 of the disposable tubing assembly 930 to provide power to the warmer 932 and/or to the reusable drive unit 940 via the disposable tubing assembly 930. The charger base 910 is also configured to be reversibly coupled to the external power source 911 such that the charger base 910 supports and charges the external power source 911.

In some embodiments, to set up the system 900 in the first use configuration, the disposable tubing assembly 930 can be removed from sterile packaging. The reusable drive unit 940 can be undocked from the charger base 910 (e.g., separated from mechanical and electrical engagement with the charger base 910). The fluid pump 931 can be coupled to the reusable drive unit 940. The disposable tubing assembly 930 can be fluidically coupled similarly to any known IV tubing to the fluid source(s) 920 (e.g., fluid or blood bags) via the spikes 937. Optionally, when multiple bags 920 are coupled to the spikes 937, the user may control which bag 920 is open to flow by opening or closing clamps associated with each bag 920 similarly to any known IV tubing. The power supply cord 934 can be electrically coupled to (e.g., plugged into) the DC power supply cord 914, which is connected to an AC-DC converter (e.g., AC-DC converter 615) in the charger base 910, such that power can be supplied to the warmer 932 via the power supply cord 934. The disposable tubing assembly 930 can be fluidically primed. In some embodiments, the fluid pump 931 can be activated via a user interface (e.g., the user interface 544) on the reusable drive unit 940, fluid (e.g., saline and/or blood) is pulled into the disposable tubing 930. After the disposable tubing assembly 930 has been fully primed, the distal end of the disposable tubing assembly 930 can be coupled to the patient's vasculature (e.g., to the patient's vascular access port). The user can then initiate and control infusion into the patient and/or warming of the fluid through interaction with the user interface on the reusable drive unit 940.

When fluid (e.g., blood or saline) in one or more of the fluid bags 920 is exhausted, the fluid bags may be replaced with new fluid bags to continue infusion, similarly to any other known IV tubing sets. After an infusion operation is complete, the disposable tubing assembly 930 can be decoupled from the patient, the warmer power supply cord 934 can be decoupled from the external battery 911 (e.g., via decoupling the power supply cord 934 from the DC power supply cord 914), and the fluid pump 931 can be decoupled from the reusable drive unit 940. The entire disposable tubing assembly 930 can then be discarded (e.g., thrown away).

During operation of the system 900, the fluid pump 931 can draw fluid from the fluid source 920, through the fluid inlet line, and into the fluid pump 931. In some embodiments, an optional blood filter (not shown) may be present in or coupled to the fluid inlet line of the disposable tubing assembly 930 to filter blood products prior to infusion. The fluid pump 931 can drive fluid from the fluid pump 931 through the fluid outlet line, through the warmer 932, and into the patient (e.g., via a vascular access port). In some embodiments, an optional air filter may be present in or coupled to the fluid outlet line (e.g., between the warmer 932 and the patient) to remove small air bubbles present in the disposable tubing assembly 930.

The charger base 910 can be plugged into an AC power source (e.g., an AC wall outlet). The charger base 910 includes an AC-DC converter (e.g., AC-DC converter 615) which provides DC power to the DC power supply cord 914 based on power received from the AC power source. In some embodiments, electrical current from the DC power supply cord 914 can flow via the integrated warmer power cord 934 to the fluid pump 931, from where the electrical current can flow to both the warmer 932 (e.g., via another portion of the integrated power cord 934) and to the reusable drive unit 940 (e.g., via an electrical connection between the fluid pump 931 and the reusable drive unit 940) to power a motor (e.g., the infusion motor 542) and/or to charge an internal battery (e.g., the internal backup battery 545) housed within the reusable drive unit 940. If the warmer power supply cord 934 is unplugged from the DC power supply cord 914, infusion can be continued via power from the internal backup battery of the reusable drive unit 940, but warming will be discontinued.

Figure 10:
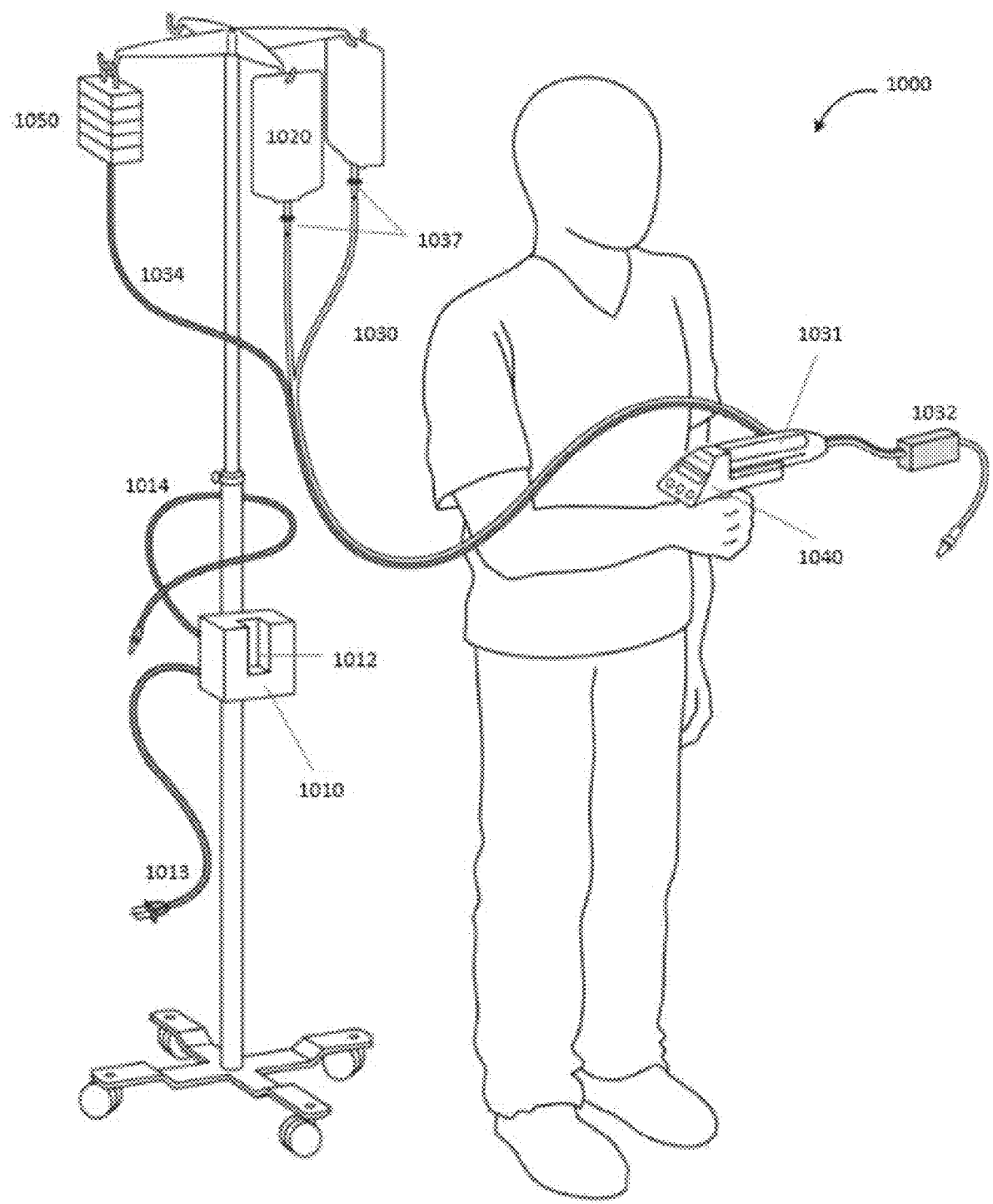
FIG. 10 is a schematic illustration of a charger base, according to an embodiment.

FIG. 10 is a schematic illustration of a system 1000 in a second use configuration (e.g., a configuration in which AC power is not drawn during an infusion operation such that the system 1000 is portable relative to a wall outlet). The system 1000 can be the same or similar in structure and/or function to any of the systems described herein, such as the system 300. For example, the system 1000 can include a disposable tubing assembly 1030, the reusable drive unit 1040, and a charger base 1010. The disposable tubing assembly 1030 can include a fluid pump 1031, a warmer 1032, and spikes 1037 configured to fluidically couple tubing of the disposable tubing assembly 1030 with fluid sources 1020 (e.g., sources of any suitable fluid such as saline, fluid including crystalloids such as 0.9% sodium chloride, blood, and/or blood products). The disposable tubing assembly 1030 also includes a power supply cord 1034. The charger base 1010 includes a power cord 1013 configured to couple the charging base 1010 to a source of AC power (e.g., an AC wall outlet) and a DC output cord 1014. The system 1000 also includes an external power supply 1050 configured to be coupled to the power supply cord 1034 of the disposable tubing assembly 1030 to provide power to the warmer 1032 and/or to the reusable drive unit 1040 via the disposable tubing assembly 1030. The charger base 1010 is configured to be reversibly coupled to the external power source 1050 via the DC output cord 1014 to provide charging power to the external power source 1050. In some embodiments, the external power supply 1050 can be configured to be coupled to the charger base 1010 like the power supply 911 described above with respect to FIG. 9 for charging and support. In some embodiments, the system 1000 can be the same system as system 900, transitioned from the first use configuration to the second use configuration.

In some embodiments, to set up the system 1000 in the second use configuration, the disposable tubing assembly 1030 can be removed from sterile packaging. The reusable drive unit 1040 can be undocked from the charger base 1010 (e.g., separated from mechanical and electrical engagement with the charger base 1010). The external power supply 1050 can be undocked from the charger base 1010. In some embodiments, the external power supply 1050 can optionally be hung from an IV pole, such that the fluid source(s) 1020 and external power supply 1050 are in close proximity, minimizing cord management needs. The fluid pump 1031 can be coupled to the reusable drive unit 1040. The disposable tubing assembly 1030 can be fluidically coupled similarly to any known IV tubing to the fluid source(s) 1020 (e.g., fluid or blood bags) via the spikes 1037. Optionally, when multiple bags 1020 are coupled to the spikes 1037, the user may control which bag 1020 is open to flow by opening or closing clamps associated with each bag 1020 similarly to any known IV tubing. The power supply cord 1034 can be electrically coupled to (e.g., plugged into) the external power supply 1050 such that power can be supplied to the warmer 1032 via the power supply cord 1034. The disposable tubing assembly 1030 can be fluidically primed. In some embodiments, the fluid pump 1031 can be activated via a user interface (e.g., the user interface 544) on the reusable drive unit 1040, fluid (e.g., saline and/or blood) is pulled into the disposable tubing 1030. After the disposable tubing assembly 1030 has been fully primed, the distal end of the disposable tubing assembly 1030 can be coupled to the patient's vasculature (e.g., to the patient's vascular access port). The user can then initiate and control infusion into the patient and/or warming of the fluid through interaction with the user interface on the reusable drive unit 1040.

When fluid (e.g., blood or saline) in one or more of the fluid bags 1020 is exhausted, the fluid bags may be replaced with new fluid bags to continue infusion, similarly to any other known IV tubing sets. After an infusion operation is complete, the disposable tubing assembly 1030 can be decoupled from the patient, the warmer power supply cord 1034 can be decoupled from the external power supply 1050, and the fluid pump 1031 can be decoupled from the reusable drive unit 1040. The entire disposable tubing assembly 1030 can then be discarded (e.g., thrown away).

During operation of the system 1000, the fluid pump 1031 can draw fluid from the fluid source 1020, through the fluid inlet line, and into the fluid pump 1031. In some embodiments, an optional blood filter (not shown) may be present in or coupled to the fluid inlet line of the disposable tubing assembly 1030 to filter blood products prior to infusion. The fluid pump 1031 can drive fluid from the fluid pump 1031 through the fluid outlet line, through the warmer 1032, and into the patient (e.g., via a vascular access port). In some embodiments, an optional air filter may be present in or coupled to the fluid outlet line (e.g., between the warmer 1032 and the patient) to remove small air bubbles present in the disposable tubing assembly 1030.

Electrical current from the external power supply 1050 can flow via the integrated warmer power cord 1034 to the fluid pump 1031, from where the electrical current can flow to both the warmer 1032 (e.g., via another portion of the integrated power cord 1034) and to the reusable drive unit 1040 (e.g., via an electrical connection between the fluid pump 1031 and the reusable drive unit 1040) to power a motor (e.g., the infusion motor 542) and/or to charge an internal battery (e.g., the internal backup battery 545) housed within the reusable drive unit 1040. In some embodiments, electrical current can be provided from the external power supply 1050 to the warmer 1032, and the reusable drive unit 1040 can operate to drive the fluid pump 1031 using power from an internal power storage component (e.g., internal backup battery) of the reusable drive unit 1040. Such a configuration may allow the system 100 to maximize fluid warming by the warmer 1032. In some embodiments, electrical current can be provided from the external power supply 1050 to the warmer 1032 and to the reusable drive unit 1040 via an electrical connection between the fluid pump 1031 and the reusable drive unit 1040 to power the infusion motor and the warmer 1032 concurrently (e.g., until the external battery 1050 is exhausted). In some embodiments, electrical current can be provided from the external power supply 1050 to the warmer 1032 and to the reusable drive unit 1040 via an electrical connection between the fluid pump 1031 and the reusable drive unit 1040 to power the warmer 1032 and charge the internal power storage component of the reusable drive unit 1040 concurrently (e.g., until the external battery 1050 is exhausted). If the warmer power supply cord 1034 is unplugged from the external power supply 1050 or the power storage of the external power supply 1050 is exhausted, infusion can be continued via power from the internal power storage component (e.g., internal backup battery) of the reusable drive unit 1040, but warming may be discontinued.

Figure 11:
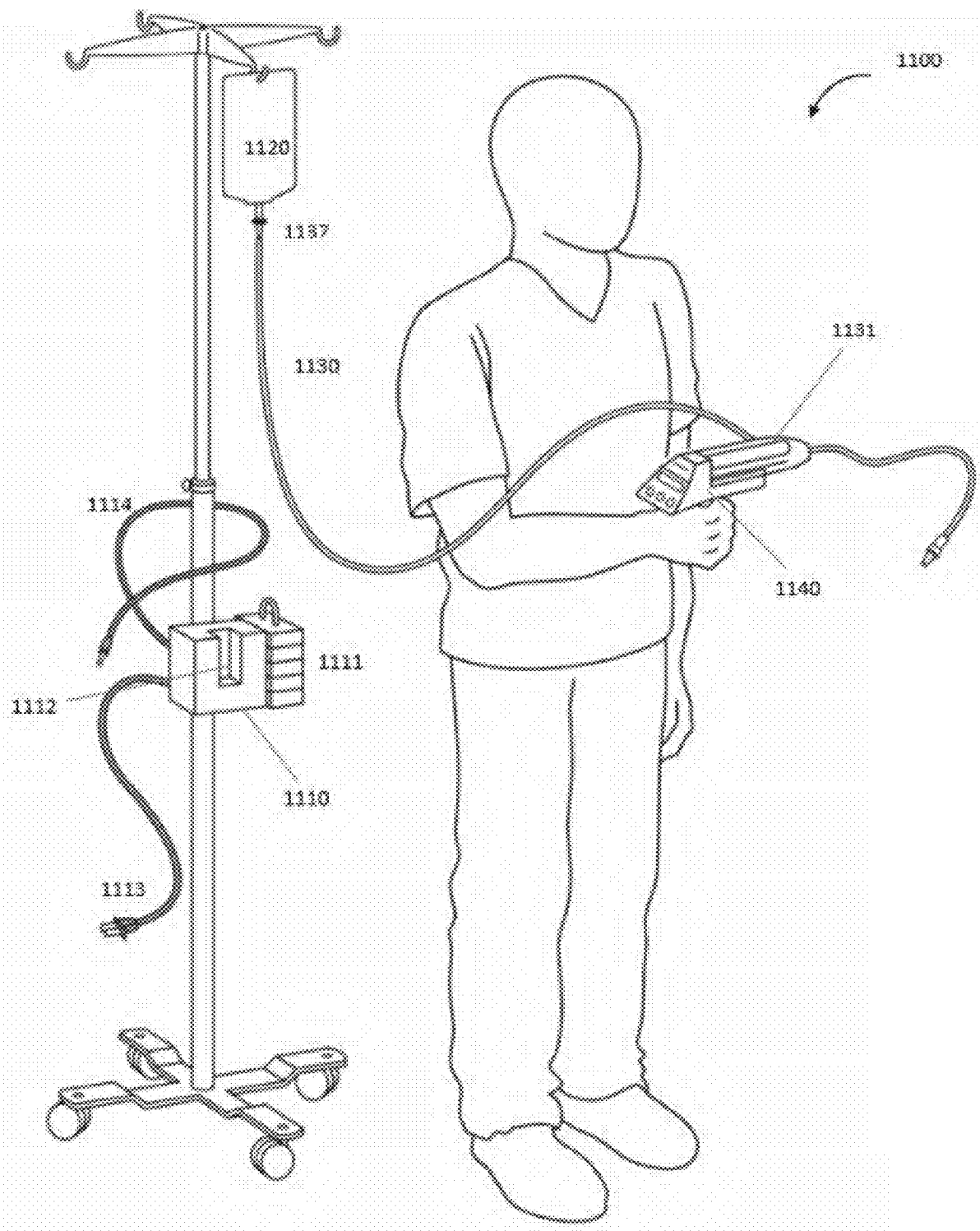
FIG. 11 is a schematic illustration of a charger base, according to an embodiment.

FIG. 11 is a schematic illustration of a system 1100 in a third use configuration (e.g., a configuration in which no warmer is included). The system 1100 can be the same or similar in structure and/or function to any of the systems described herein, such as the system 400. For example, the system 1100 can include a disposable tubing assembly 1130, the reusable drive unit 1140, and a charger base 1110. The disposable tubing assembly 1130 can include a fluid pump 1131 and spikes 1137 configured to fluidically couple tubing of the disposable tubing assembly 1130 with fluid source(s) 1120 (e.g., sources of any suitable fluid such as saline, fluid including crystalloids such as 0.9% sodium chloride, blood, and/or blood products). The charger base 1110 includes a power cord 1113 configured to couple the charging base 1110 to a source of AC power (e.g., an AC wall outlet) and a DC output cord 1114. The charger base 1110 is also configured to be reversibly coupled to the external power source 1111 such that the charger base 1110 supports and charges the external power source 1111.

In some embodiments, to set up the system 1100 in the third use configuration, the disposable tubing assembly 1130 can be removed from sterile packaging. The reusable drive unit 1140 can be undocked from a drive unit receptacle 1112 of the charger base 1110 (e.g., separated from mechanical and electrical engagement with the charger base 1110). The fluid pump 1131 can be coupled to the reusable drive unit 1140. The disposable tubing assembly 1130 can be fluidically coupled similarly to any known IV tubing to the fluid source(s) 1120 (e.g., fluid or blood bags) via the spike 1137. The disposable tubing assembly 1130 can be fluidically primed. In some embodiments, the fluid pump 1131 can be activated (e.g., for priming and/or an infusion operation) via a user interface (e.g., the user interface 544) on the reusable drive unit 1140, fluid (e.g., saline and/or blood) is pulled into the disposable tubing 1130. After the disposable tubing assembly 1130 has been fully primed, the distal end of the disposable tubing assembly 1130 can be coupled to the patient's vasculature (e.g., to the patient's vascular access port). The user can then initiate and control infusion into the patient and/or warming of the fluid through interaction with the user interface on the reusable drive unit 1140.

When fluid (e.g., blood or saline) in one or more of the fluid bags 1120 is exhausted, the fluid bags may be replaced with new fluid bags to continue infusion, similarly to any other known IV tubing sets. After an infusion operation is complete, the disposable tubing assembly 1130 can be decoupled from the patient and the fluid pump 1131 can be decoupled from the reusable drive unit 1140. The entire disposable tubing assembly 1130 can then be discarded (e.g., thrown away).

During operation of the system 1100 (e.g., for infusion to treat sepsis and/or other conditions), the fluid pump 1131 can draw fluid from the fluid source 1120, through the fluid inlet line, and into the fluid pump 1131. In some embodiments, an optional blood filter (not shown) may be present in or coupled to the fluid inlet line of the disposable tubing assembly 1130 to filter blood products prior to infusion. The fluid pump 1131 can drive fluid from the fluid pump 1131 through the fluid outlet line, and into the patient (e.g., via a vascular access port). In some embodiments, an optional air filter may be present in or coupled to the fluid outlet line (e.g., between the warmer 1132 and the patient) to remove small air bubbles present in the disposable tubing assembly 1130.

The charger base 1110 can be plugged into an AC power source (e.g., an AC wall outlet). The charger base 1110 includes an AC-DC converter (e.g., AC-DC converter 615) and can provide DC power to the reusable drive unit 1140 for charging an internal power storage component of the reusable drive unit 1140 when the reusable drive unit 1140 is docked with the charger base 1110. After undocking the reusable drive unit 1140 and coupling the reusable drive unit 1140 to the disposable tubing assembly 1130, the internal power storage component of the reusable drive unit 1140 can provide the operational power to drive the infusion motor (e.g., infusion motor 542) of the reusable drive unit 1140.

In some embodiments, any of the warmers described herein can be the same or similar in structure and/or function to any suitable warmers. For example, in some embodiments, any of the warmers described herein can include an elongated metal conduit having an inlet for receiving a flow of liquid at an initial temperature and an outlet for delivering the flow of liquid at a desired temperature. The metal conduit can be in substantially direct thermal contact with the flow of liquid. At least one temperature sensing arrangement associated with the conduit and can be included and configured to generate an output indicative of a temperature of the fluid at at least one location along said conduit. A controller associated with the temperature sensing arrangement can be included and configured for generating electrical current that flows within at least one length of the wall of said metal conduit, thereby generating heat within the wall so as to heat the fluid flowing therethrough to reach the desired temperature at the outlet. Such a warming mechanism can be the same or similar in structure and/or function to any of the warming mechanisms described, for example, in U.S. Pat. No. 7,846,130, entitled Portable Intravenous Fluid Heating System, issued Dec. 7, 2010, which is incorporated by reference herein for all purposes.

In some embodiments, any of the warmers described herein can include a plurality of groups of interconnected tube sections in a housing carrying intravenous fluid to be warmed between an input port and output port. Each of said tube sections can have an outer periphery. The warmer can include a plurality of flexible heating elements in the plurality of tube sections for heating the intravenous fluid therein. Each of said flexible heating elements can be wrapped around, in contact with, and surrounding at least the majority of the peripheral surface of an associated tube section. Such a warming mechanism can be the same or similar in structure and/or function to any of the warming mechanisms described in U.S. Pat. No. 6,142,974, entitled Portable I.V. Fluid Warming System, issued Nov. 7, 2000, which is incorporated by reference herein for all purposes.

In some embodiments, any of the warmers described herein can include a tubal segment having an inner sheath defining a hollow cylindrical body for conveying infusion fluid therethrough, an outer sheath disposed around the inner sheath, and a thermal element positioned between the inner sheath and the outer sheath and configured to convert electrical energy into heat for heating or cooling the conveyed infusion fluid in the hollow cylindrical body. Such a warming mechanism can be the same or similar in structure and/or function to any of the warming mechanisms described in U.S. Pat. No. 10,780,258, entitled Thermic Infusion System, issued Sep. 22, 2020, which is incorporated by reference herein for all purposes.

In some embodiments, any of the warmers described herein can include multiple temperature probes (e.g., thermocouples and/or thermistors) to provide feedback to maintain a target temperature or temperature range. Any of the warmers described herein (e.g., warmer 132) can be controlled by a controller (e.g., controller 541) included in any of the reusable drive units described herein (e.g., the reusable drive unit 140) which monitors the fluid temperature at multiple points in a flow path (e.g., through a disposable tubing assembly) and varies the amount of electrical energy delivered to the warmer accordingly in order to maintain the target temperature or temperature range.

A warmer, such as any of the warmers described herein, can be disposed in multiple different locations along any of the disposable tubing assemblies described herein (e.g., near a fluid pump such as any of the fluid pumps described herein). The location(s) of the warmer can be dependent on the warming mechanism being used, as shown in FIGS. 12 and 13.

Figure 12:
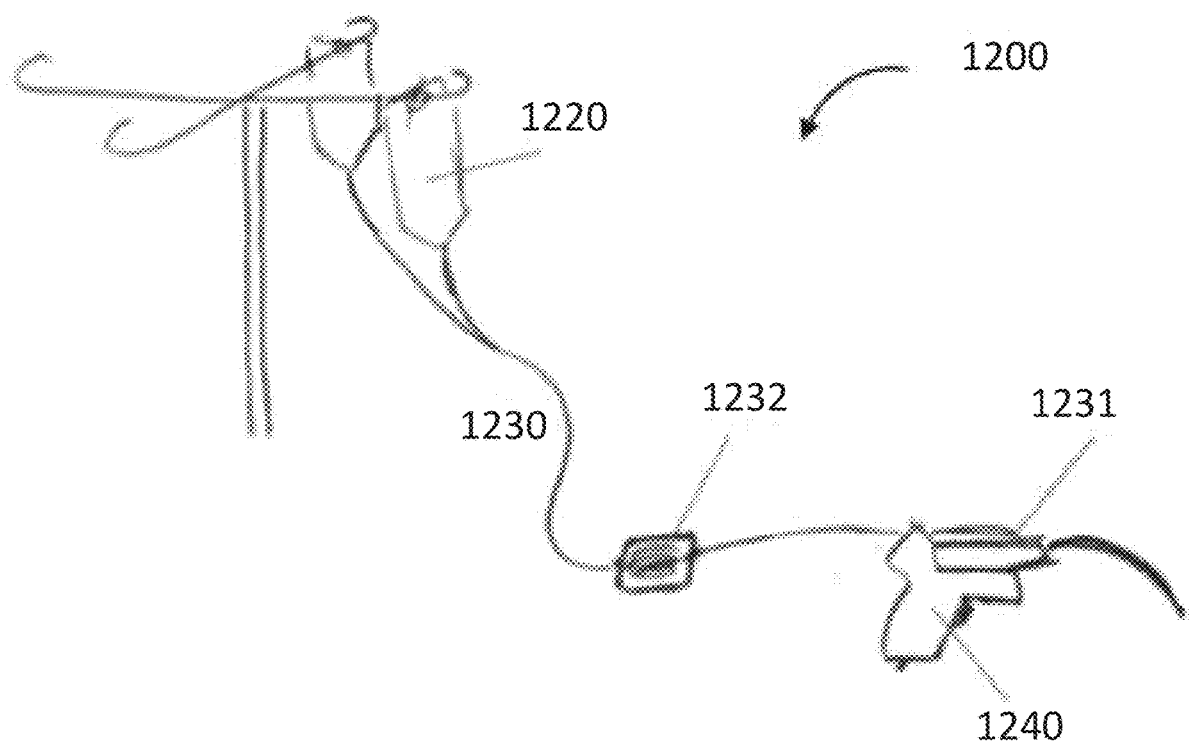
FIG. 12 is a schematic illustration of a charger base, according to an embodiment.

FIG. 12 is a schematic illustration of a system 1200. The system 1200 can be the same or similar in structure and/or function to any of the systems described herein. For example, the system 1200 includes a fluid delivery assembly 1230, a reusable drive unit 1240, and a warmer 1232. The fluid delivery assembly 1230 includes a fluid pump 1231 and can be fluidically coupled to a fluid source 1220. As shown in FIG. 12, the warmer 1232 can be disposed between the fluid source 1220 and the fluid pump 1231.

Figure 13:
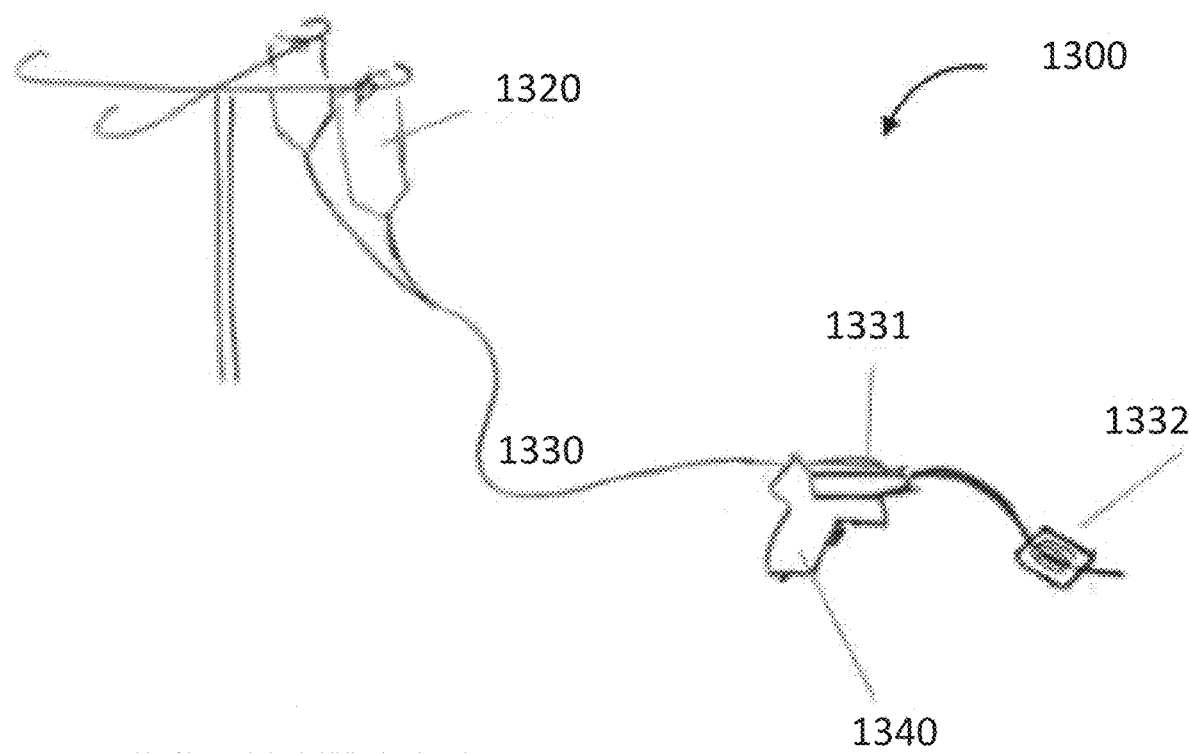
FIG. 13 is a schematic illustration of a charger base, according to an embodiment.

FIG. 13 is a schematic illustration of a system 1300. The system 1300 can be the same or similar in structure and/or function to any of the systems described herein. For example, the system 1300 includes a fluid delivery assembly 1330, a reusable drive unit 1340, and a warmer 1332. The fluid delivery assembly 1330 includes a fluid pump 1331 and can be fluidically coupled to a fluid source 1320. As shown in FIG. 13, the warmer 1332 can be disposed between the fluid pump 1331 and the patient. In some embodiments, the system 1300 can include two warmers, such as the warmer 1232 disposed between the between the fluid source 1220 and the fluid pump 1231 and the warmer 1332 disposed between the fluid pump 1331 and the patient.

Figure 14:
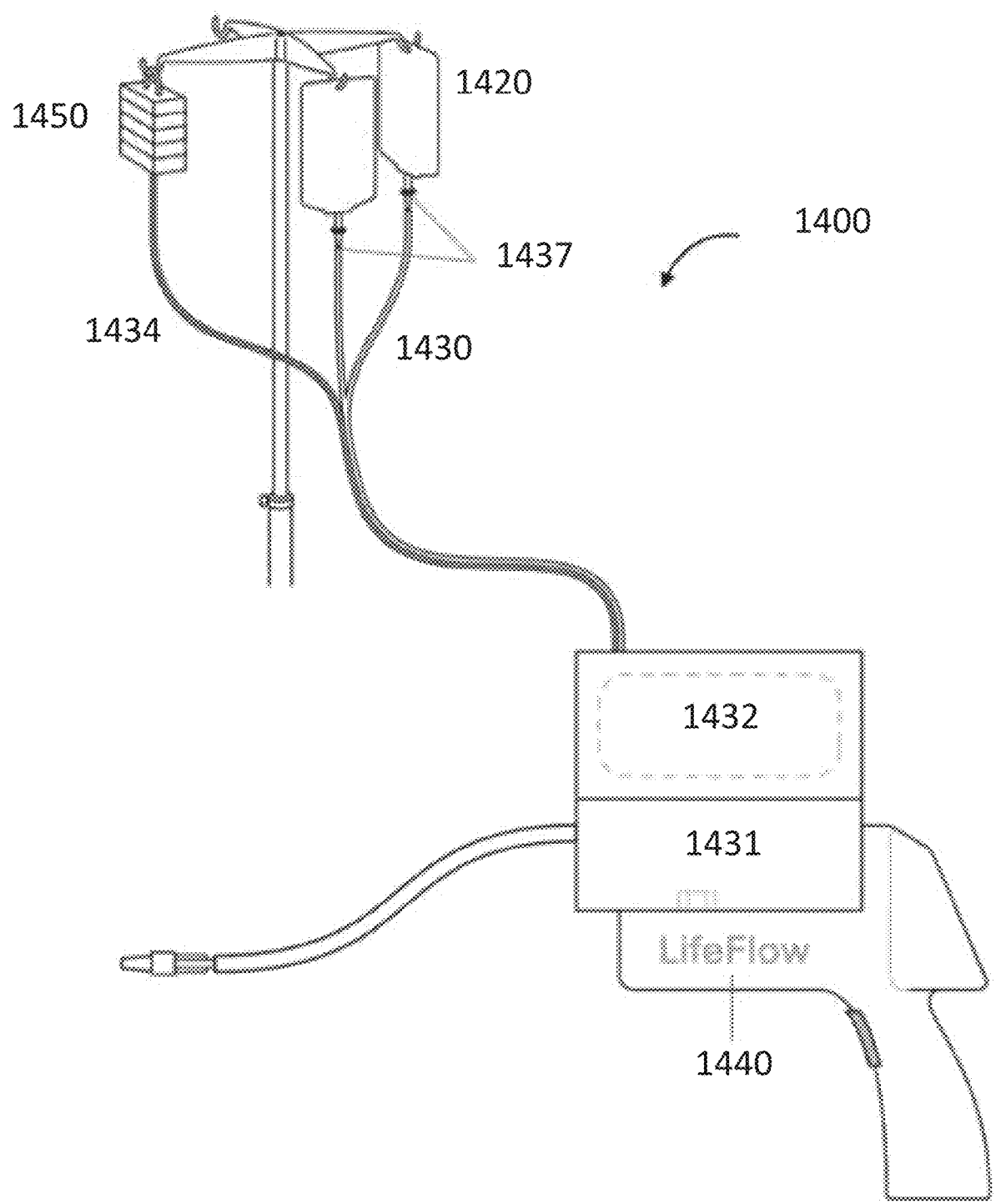
FIG. 14 is a schematic illustration of a charger base, according to an embodiment.

FIG. 14 is a schematic illustration of a system 1400. The system 1400 can be the same or similar in structure and/or function to any of the systems described herein. For example, the system 1400 includes a fluid delivery assembly 1430, a reusable drive unit 1440, and a warmer 1432. The system 1400 also includes an external power supply 1450 coupled to the warmer 1432 via a power supply cord 1434. The fluid delivery assembly 1430 includes a fluid pump 1431 and can be fluidically coupled to a fluid source 1420 via spike(s) 1437. As shown in FIG. 14, the warmer 1432 can be integrated into a common housing as the fluid pump 1431 and disposed between the fluid pump 1431 and the fluid source 1420. The warmer power supply cord 1434 can optionally be integrated into the disposable tubing assembly 1730 tubing (e.g., upstream of the warmer 1432) or not integrated (i.e., run separately). The warmer power supply cord 1434 can include at least a portion that is coupled to a length of the tubing of the disposable tubing assembly 1730 (e.g., from the portion connected to the warmer 1432 to a midpoint of the inlet tubing). The external power supply 1450 can be hung from an IV pole that also supports the fluid source 1420.

Figure 15:
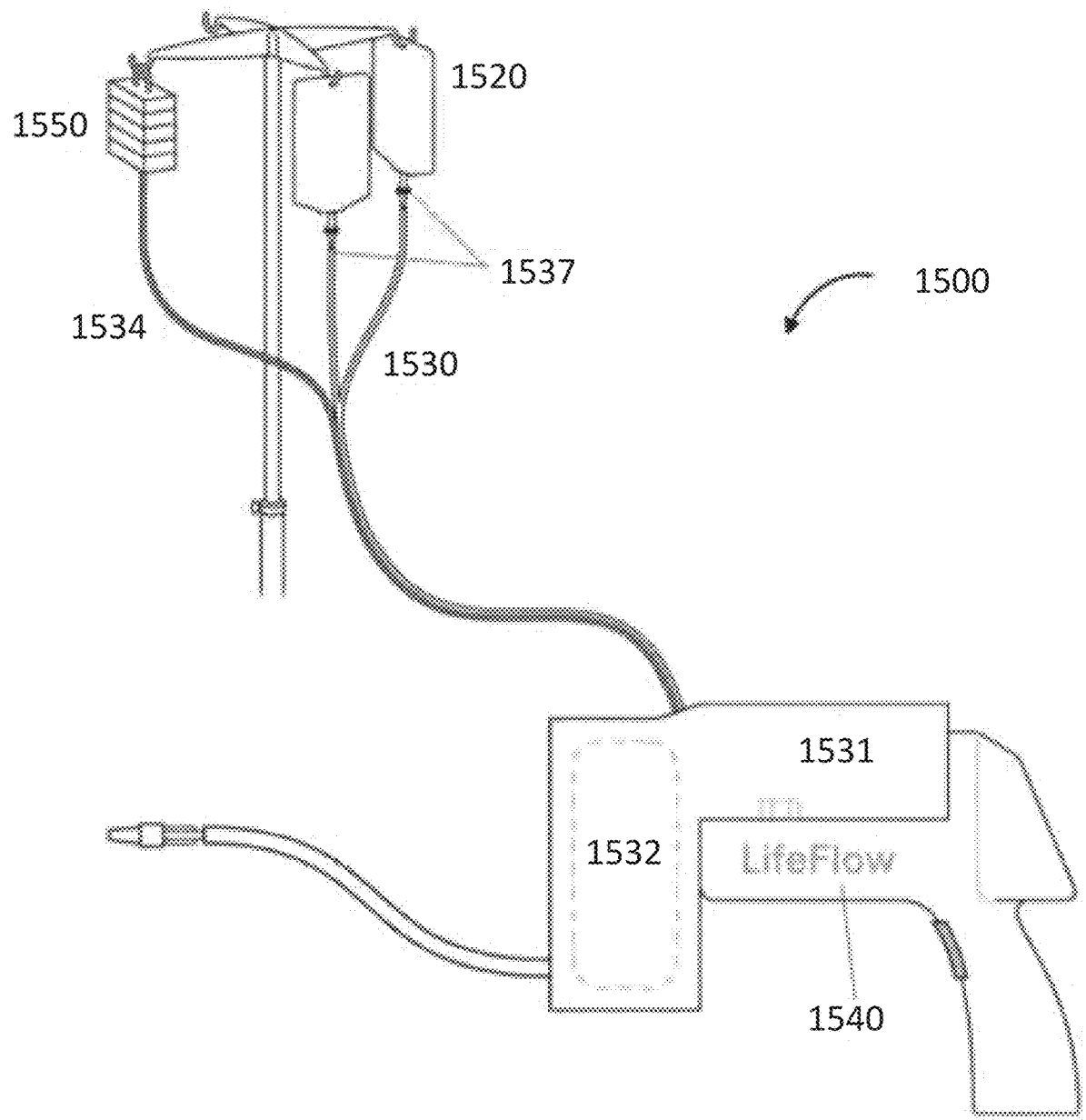
FIG. 15 is a schematic illustration of a charger base, according to an embodiment.

FIG. 15 is a schematic illustration of a system 1500. The system 1500 can be the same or similar in structure and/or function to any of the systems described herein. For example, the system 1500 includes a fluid delivery assembly 1530, a reusable drive unit 1540, and a warmer 1532. The system 1500 also includes an external power supply 1550 coupled to the warmer 1532 via a power supply cord 1534. The fluid delivery assembly 1530 includes a fluid pump 1531 and can be fluidically coupled to a fluid source 1520 via spike(s) 1537. As shown in FIG. 15, the warmer 1532 can be integrated into a common housing as the fluid pump 1531 and disposed between the fluid pump 1531 and the patient. In some embodiments, the system 1500 can include two warmers, such as the warmer 1432 disposed between the between the fluid source 1420 and the fluid pump 1431 and the warmer 1532 disposed between the fluid pump 1531 and the patient.

Figure 16:
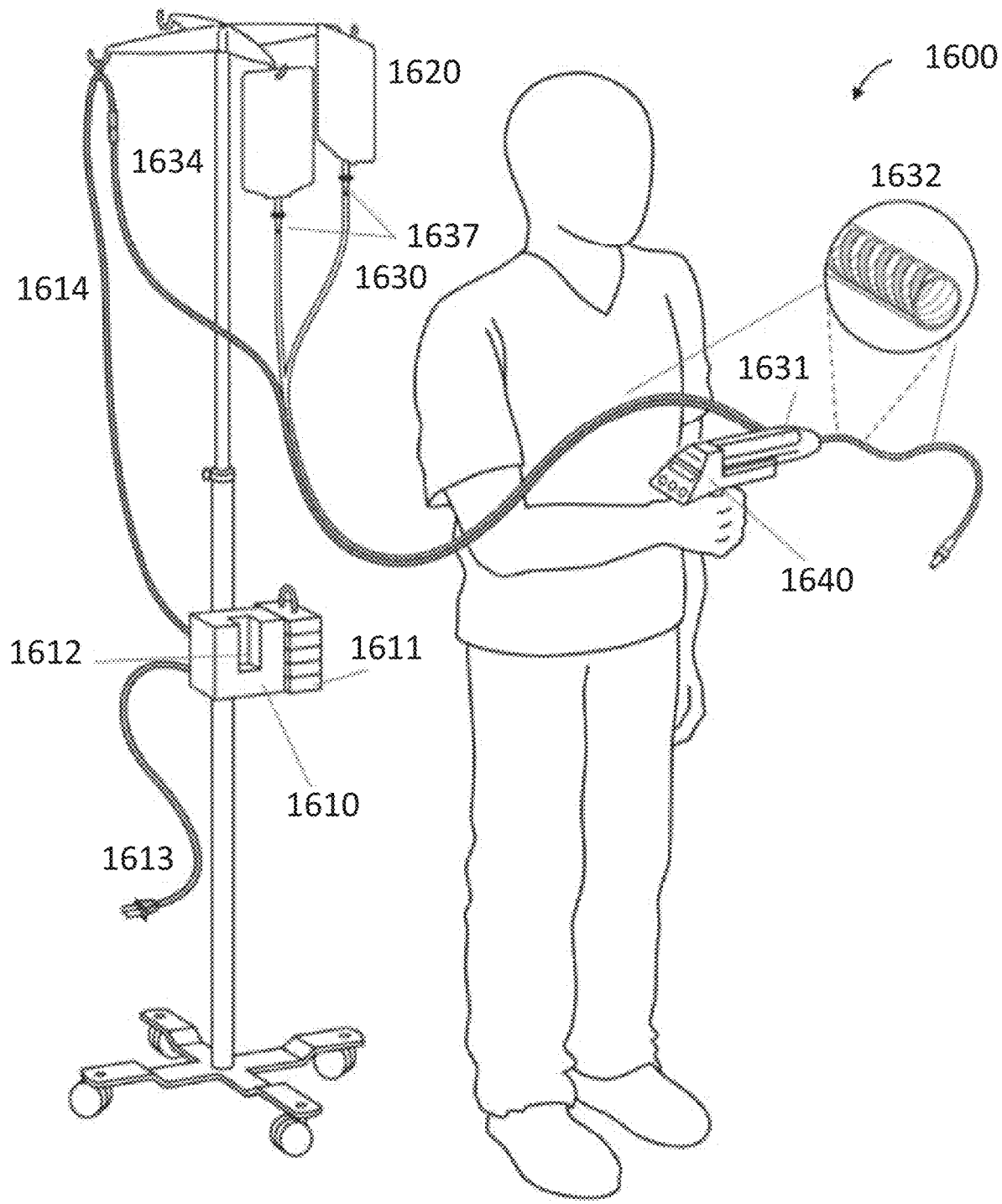
FIG. 16 is a schematic illustration of a charger base, according to an embodiment.

FIG. 16 is a schematic illustration of a system 1600. The system 1600 can be the same or similar in structure and/or function to any of the systems described herein. For example, the system 1600 includes a fluid delivery assembly 1630, a reusable drive unit 1640, a warmer 1632, and a charger base 1610 configured to receive the reusable drive unit 1640 in a receptacle 1612 of the charger base 1610. The system 1600 also includes an external power supply 1611. The charger base 1610 includes an AC power supply cord 1613 and a DC power supply cord 1614 configured to be coupled to the warmer 1632 via a power supply cord 1634. The fluid delivery assembly 1630 includes a fluid pump 1631 and can be fluidically coupled to a fluid source 1620 via spikes 1637. As shown in FIG. 16, the warmer 1632 can be integrated into the tubing of the disposable tubing assembly 1630 (e.g., both upstream and downstream relative to the fluid pump 1631). In some embodiments, a small amount of electrical resistance may be included in the cord 1634, allowing the fluid in the inlet tubing of the disposable tubing assembly 1630 to be pre-warmed prior to reaching the warmer 1632.

Figure 17:
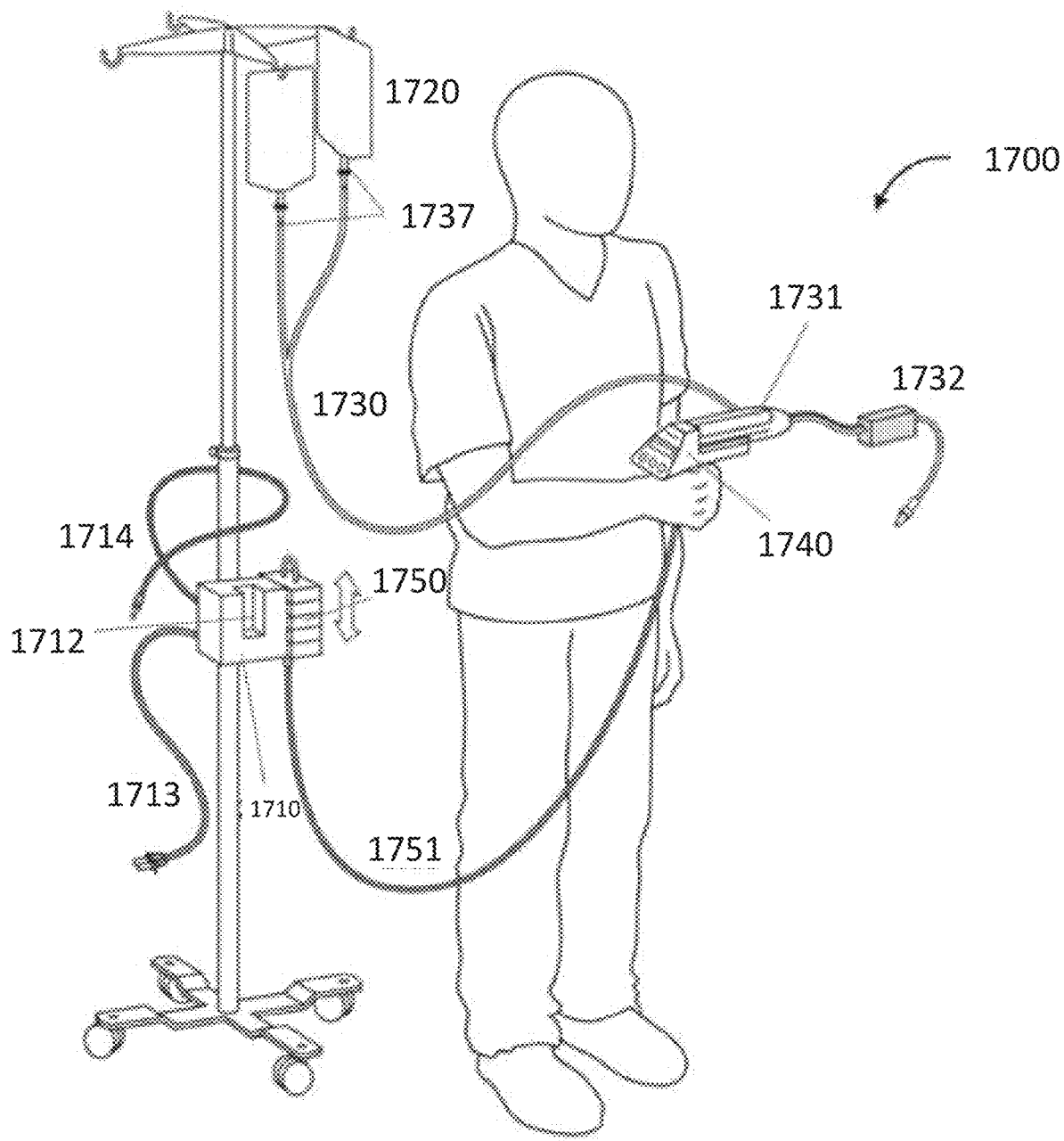
FIG. 17 is a schematic illustration of a charger base, according to an embodiment.
Figure 18:
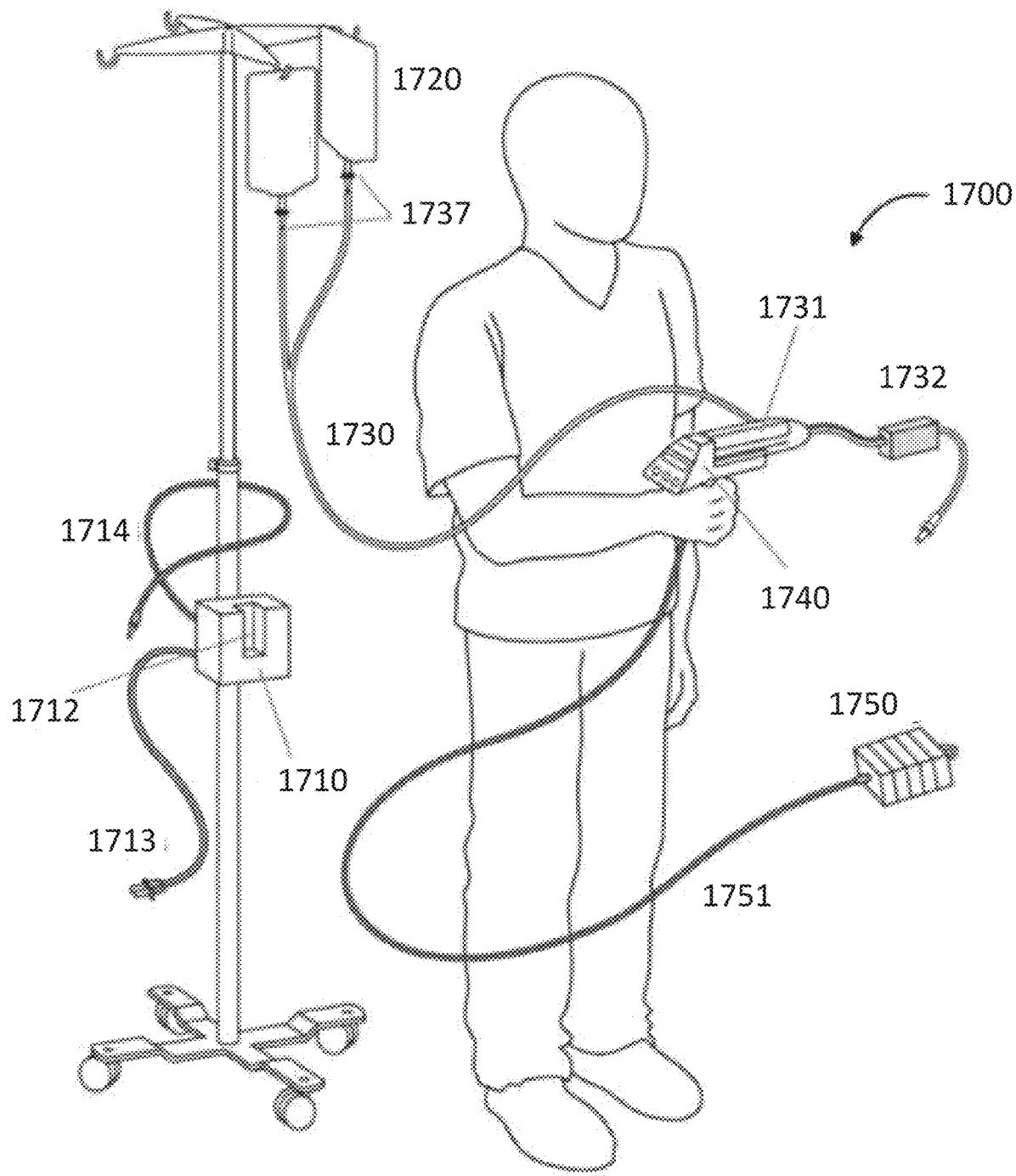
FIG. 18 is a schematic illustration of a charger base, according to an embodiment.
Figure 19:
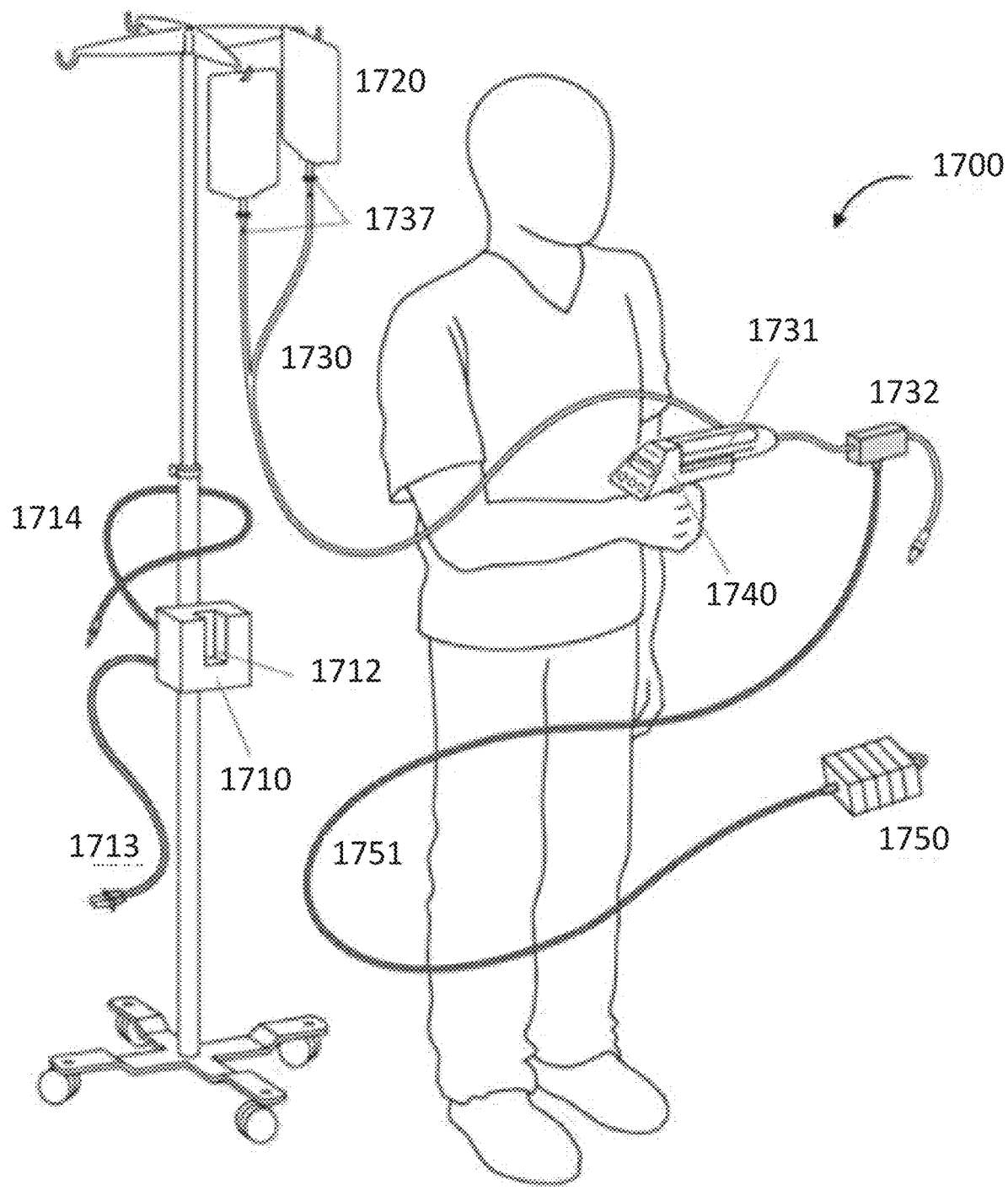
FIG. 19 is a schematic illustration of a charger base, according to an embodiment.
Figure 22:
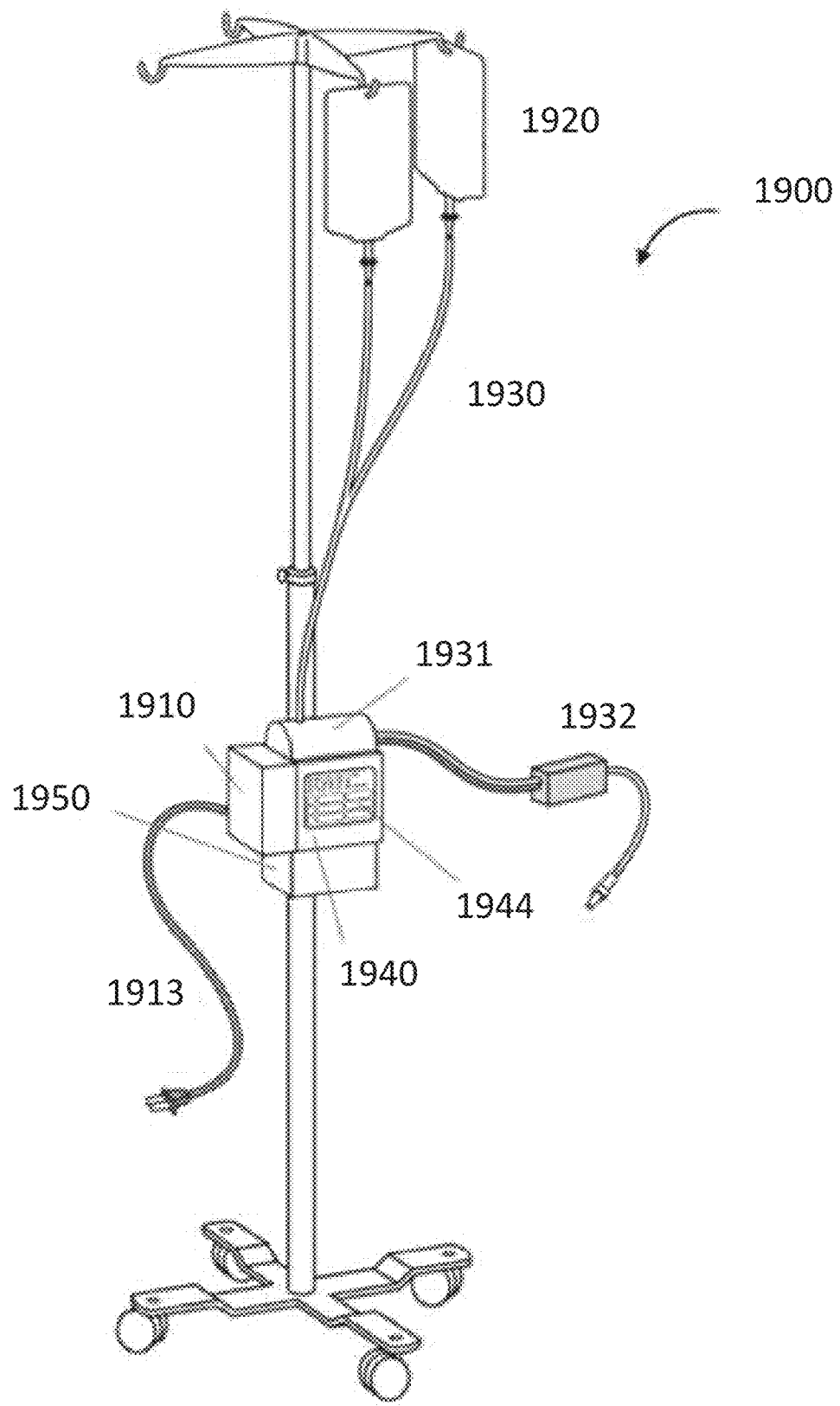

FIGS. 17-19 are schematic illustrations of a system 1700. The system 1700 can be the same or similar in structure and/or function to any of the systems described herein. For example, the system 1700 includes a fluid delivery assembly 1730, a reusable drive unit 1740, a warmer 1732, and a charger base 1710 configured to receive the reusable drive unit 1740 in a receptacle 1712 of the charger base 1710. The charger base 1710 includes an AC power supply cord 1713 and a DC power supply cord 1714. The system 1700 also includes an external power supply 1750 configured to be coupled to the warmer 1732 via a power supply cord 1751 separate from the inlet tubing of the fluid delivery assembly 1730. The external power supply 1750 can be couplable and decouplable from the charge base 1710 (as shown in FIG. 22), can be hung from a hook on the IV pole, and can be placed on a surface such as a patient bed during operation. The power supply cord 1751 can be releasably electrically coupled to a plug on the reusable drive unit 1740 and to the external power supply 1750 or to the DC power supply cord 1714. The fluid delivery assembly 1730 includes a fluid pump 1731 and can be fluidically coupled to a fluid source 1720 via spikes 1737. As shown in FIG. 17, the warmer 1732 can be disposed downstream of the fluid pump 1731 of the disposable tubing assembly 1730. In some embodiments, as shown in FIG. 19, the cord 1751 or another cord similar to and/or in addition to the cord 2251 can electrically couple the warmer 1732 directly to the external power source 1750.

In some embodiments, a user interface, such as any of the user interfaces described herein (e.g., user interface 544), can include one or more controls which enable the user, in combination with a controller of a reusable drive unit, to at least one of start a continuous infusion, start a bolus of a predetermined size, set the size of a bolus, start warming, stop warming, and/or transmit data electronically to hospital or medical facility electronic health records. In some embodiments, a user interface, such as any of the user interfaces described herein (e.g., user interface 544), can include a display (e.g., the display 543) which enables the user to view at least one of volume infused, elapsed time of infusion, infusion rate, target volume (i.e. size of bolus if running continuously), time to completion of bolus, warming on/off, warming set point, fluid input temperature, fluid output temperature, battery life, and/or error messages.

Figure 20:
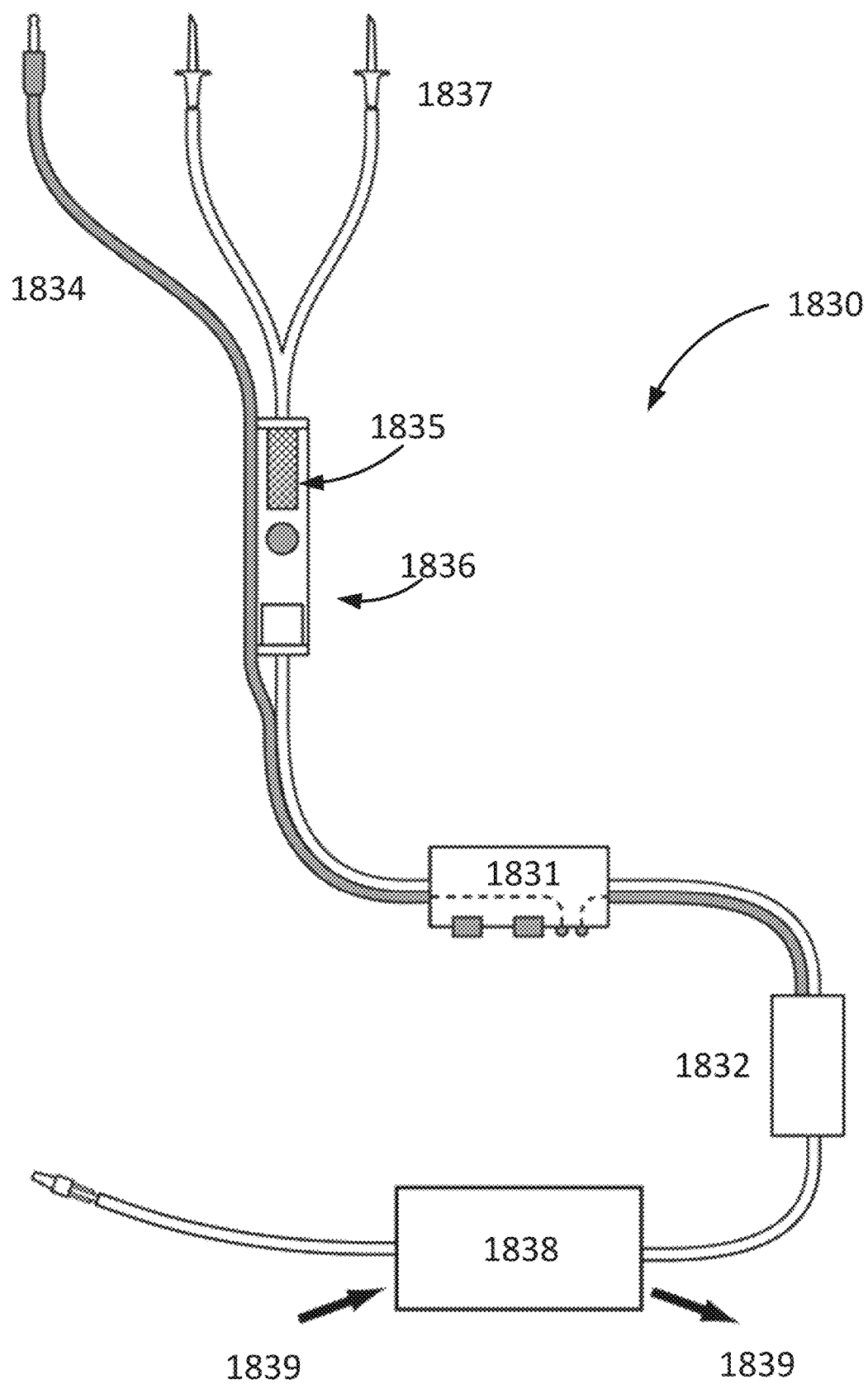
FIG. 20 is a schematic illustration of a fluid delivery assembly, according to an embodiment.

In some embodiments, any of the disposable tubing assemblies described herein can include one or more air detection and/or filtering features. For example, FIG. 20 is a schematic illustration of a disposable tubing assembly 1830. The disposable tubing assembly 1830 can be the same or similar in structure and/or function to any of the disposable tubing assemblies described herein, such as the disposable tubing assembly 730. For example, the disposable tubing assembly 1830 includes a fluid pump 1831, a warmer 1832, fluid spikes 1837, and a power supply cord 1834. The disposable tubing assembly 1830 also includes an air filter 1836 and, optionally, a blood filter 1835. The air filter 1836 can be the same as or similar to any of the air filters shown or described in U.S. Pat. No. 10,661,029, titled Systems, Apparatus, and Methods for Filtering Air from a Fluid Line, issued May 26, 2020, which is incorporated by reference herein. The air filter 1836 can be disposed upstream of the fluid pump 1831 such that the air filter 1836 can act as an occluding mechanism that stops infusion into the fluid pump 1831 if air or a significant volume of air enters the disposable tubing assembly 1830 until the air is removed and the mechanism is reset. The blood filter 1835 can filter blood products from the fluid from a fluid source prior to infusion.

As shown in FIG. 20, an oxygenation unit 1838 can be included in the disposable tubing assembly 1830 downstream from the fluid pump 1831 and warmer 1832. The oxygenator 1838 can be coupled to a gas generator such that gas flow 1839 travels in the opposite direction of the fluid flow, and along a high surface area semipermeable membrane, which allows oxygen to diffuse into the blood traveling through the oxygenation unit 1838 to the patient. Thus, the oxygenation unit 1838 disposed along the fluid path between the fluid pump 1831 and the patient allows the infusion of oxygenated blood into the patient, which can be advantageous in the event of a cardiac arrest. Although FIG. 20 shows the oxygenator 1838 included in the disposable tubing assembly 1830, in some embodiments the oxygenator 1838 may be independent of and couplable to the disposable tubing assembly 1830 (e.g., via a luer lock connection).

In some embodiments, any of the disposable tubing assemblies described herein can include or be coupled to an ultrasound air detection sensor. For example, air bubbles in the fluid line of any of the disposable tubing systems described herein may be detected via ultrasound detection. A sensor including an ultrasound transducer can produce a signal at regular intervals and listen for a reflected signal back to the sensor. If air bubbles are present, the signal will not return in a predetermined time window, indicating bubbles are present in the tubing in front of the sensor. If this occurs, the system may generate an alarm and/or activate a clamp to occlude the fluid path and stop any flow to the patient.

In some embodiments, any of the disposable tubing assemblies described herein can include or be coupled to an electrical resistance sensing sensor. For example, air bubbles in the fluid line of any of the disposable tubing systems described herein may be detected via electrical resistance. Two electrodes can be present within a length of tubing and isolated from each other, except for the saline, blood or other liquids present in the tubing. A small electric current can be passed between the two electrodes, and the resistance of the circuit is measured. If air bubbles are present between the electrodes, the resistance will change and be detected by the sensor. If this occurs, the system may generate an alarm and/or activate a clamp to occlude the fluid path and stop any flow to the patient.

In some embodiments, any of the disposable tubing assemblies described herein can include or be coupled to a downstream air filter. The air filter can include a hydrophobic membrane. Small air bubbles can be filtered out of a disposable tubing assembly by passing in close proximity to the hydrophobic membrane, allowing the air to be vented out of the tubing. The fluid can travel through the filter after passing through a fluid pump of the disposable tubing assembly.

In some embodiments, any of the disposable tubing assemblies described herein can include or be coupled to an upstream air filter. The air filter can include a hydrophobic membrane. Small air bubbles can be filtered out of a disposable tubing assembly by passing in close proximity to the hydrophobic membrane, allowing the air to be vented out of the tubing. The fluid can travel through the filter before passing through a fluid pump of the disposable tubing assembly.

In some embodiments, any of the reusable drive units described herein, such as the reusable drive unit 140, can be a mechanically-powered reusable or disposable drive unit configured to actuate a fluid pump such as the fluid pump 131. Rather than electricity being used to power the fluid pump, the user may provide energy to the fluid pump via a lever, crank, or similar mechanical mechanism. For example, the reusable drive unit 140 can be the same or similar in structure and/or function to any of the infusion devices described in U.S. Pat. No. 10,016,564, entitled Apparatus and Kits for Fluid Infusion, issued Jul. 10, 2018, which is incorporated by reference herein for all purposes.

In some embodiments, any of the systems described herein can include a temperature sensor at an outlet of the disposable tubing assembly (e.g., the disposable tubing assembly 130) that can communicate the outlet temperature of fluid downstream of a warmer, such as any of the warmers described herein, back to a reusable drive unit (e.g., the reusable drive unit 140), triggering adjustments in flow rate by a fluid pump of the disposable tubing assembly as needed to maintain a target temperature. Communication between the reusable drive unit and the warmer and/or a sensor associated with the warmer may also allow for the warmer to quickly respond to changes in flow rate to hold a target temperature and to avoid overshooting or undershooting the temperature when the flow rate changes. When the controller (e.g., the controller 541) detects that the warmer is producing the maximum power and the fluid temperature is dropping below the desired set point, the controller may reduce the fluid pump speed and reduce the flow of cold fluid through the warmer. With multiple temperature readings present throughout the length of the warmer, the reduction in fluid flow may occur quickly enough such that the fluid exiting the warmer remains above the set point. Conversely if the user stops or slows the fluid pump, the controller may decrease the power going to the warmer, without regard to the temperature sensor readings. When the fluid flow slows down, excess heat may begin to build up in the fluid and proactively reducing the energy flow can reduce the risk of the blood or fluid getting above a desired set point.

In an embodiment with a mechanically-powered drive unit, communication between the fluid pump and the warmer can provide one-way communication from the fluid pump or drive unit to the warmer. This would provide the flow rate of fluid exiting the fluid pump to the controller to allow it to adjust warming energy appropriately. When the fluid pump starts pumping or increases the rate of pumping, the controller could begin increasing energy supplied to the warmer beyond what would be indicated from the temperature sensors in the warmer. When the flow rate from the fluid pump decreases or stops, the controller could begin decreasing energy supplied to the warmer beyond what would be indicated by the temperature sensors in the warmer.

In some embodiments, one or more pressure sensors can be included in any of the systems described herein and can provide information regarding the status of the proximal (towards the fluid source) and distal (towards the patient) fluid pathways. For example, a distinct increase in pressure in the distal tubing may indicate an occlusion in the fluid pathway towards the patient and communicate that back to the reusable drive unit (e.g., reusable drive unit 140) to stop infusion and alarm the user about the issue. A pressure sensor may also be used to determine if a vacuum/negative pressure occurs in the proximal tubing. This would be indicative of either an air filter (e.g., the air filter 1836) ball occluding the tubing, clamps being left on, or an empty fluid bag, and would also trigger an error message to the user.

Figure 21:
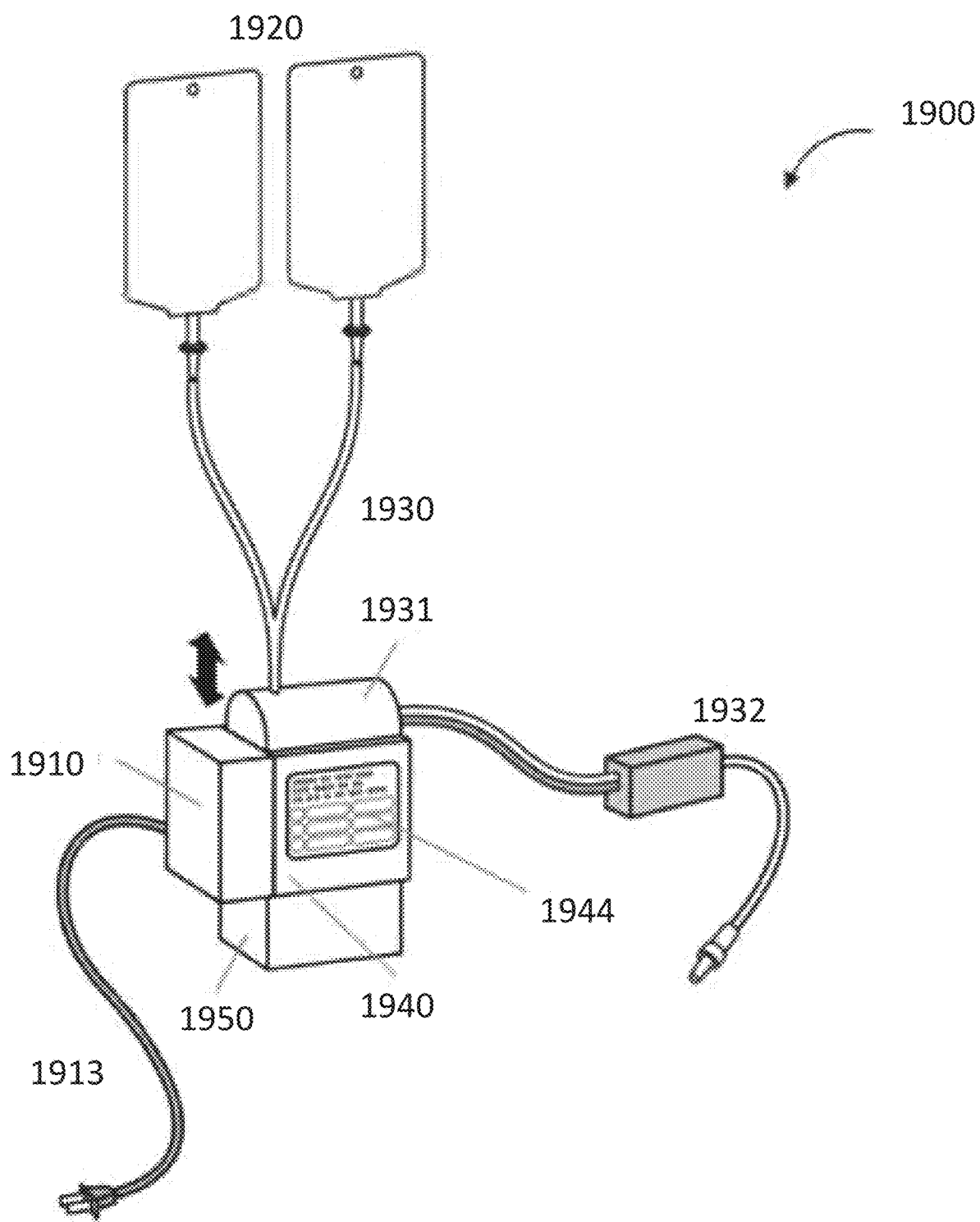
FIGS. 21 and 22 are schematic illustrations of a fluid delivery assembly, according to an embodiment.

In some embodiments, a reusable drive unit, such as any of the reusable drive units described herein, can be handheld. In some embodiments the reusable drive unit can include a grip and/or a trigger. In some embodiments, a reusable drive unit, such as any of the reusable drive units described herein, can be non-handheld and can be designed such that they can be rested on a patient bed and/or affixed to an IV pole. For example, FIGS. 21 and 22 are schematic illustrations of a system 1900. FIG. 21 shows the system 1900, which is a portable infuser system, in an unmounted configuration. FIG. 22 shows the system 1900 mounted to an IV pole. The system 1900 includes a disposable tubing assembly 1930, a charger base 1910, a reusable drive unit 1940, an external power source 1950, and a fluid source 1920. The reusable drive unit 1940 includes a user interface 1944. The disposable tubing assembly 1930 includes a fluid pump 1931 and a warmer 1932. The charger base 1910 includes an AC power cord 1913. In the configuration shown in FIG. 22, an external power supply 1950 is removable from the drive unit 1940 and the charger base 1910 contains an AC to DC converter (e.g., AC to DC converter 615), which would charge the external power supply 1950 through the drive unit 1940.

Some rapid infusers are limited in the amount of pressure they can generate (e.g., limited to 300 mmHg) due to the types of mechanisms they use to generate pressure (external pressurization of the IV bag, peristaltic pump). While some infusers may be able to deliver fluids and blood quickly through large-bore IV access or large bore central venous catheters or other venous access (e.g., 12 to 16 gauge) (upwards of 1000 mL/min), there is a drastic decrease in flow rate through peripheral IVs due to the maximum pressure (e.g., a maximum pressure of 300 mmHg). A portable rapid infuser such as the portable rapid infusers described herein can utilize a syringe-based pump which allows for higher pressures to be generated, and therefore high flow rates through both large-bore IV access and smaller bore peripheral IV access (e.g., having a gauge range of 18 to 24 gauge). By utilizing two syringes, operating 180° out of phase from each other, a substantially continuous flow of fluid can be generated by allowing one syringe to deliver fluid to the patient while the other syringe is being filled with fluid. A single-syringe pump would require a period of zero flow between syringe ejections while the syringe is filled with fluid, resulting in a highly-pulsatile pressure profile. Due to a double-syringe pump's ability to deliver substantially continuous flow, it can maintain a lower maximum pressure on the IV site compared to a single-syringe pump under the same conditions. This reduced pressure minimizes damage to blood products, potential injury to the patient, stress on the IV tubing, and instantaneous energy needs of the infuser.

Figure 23:
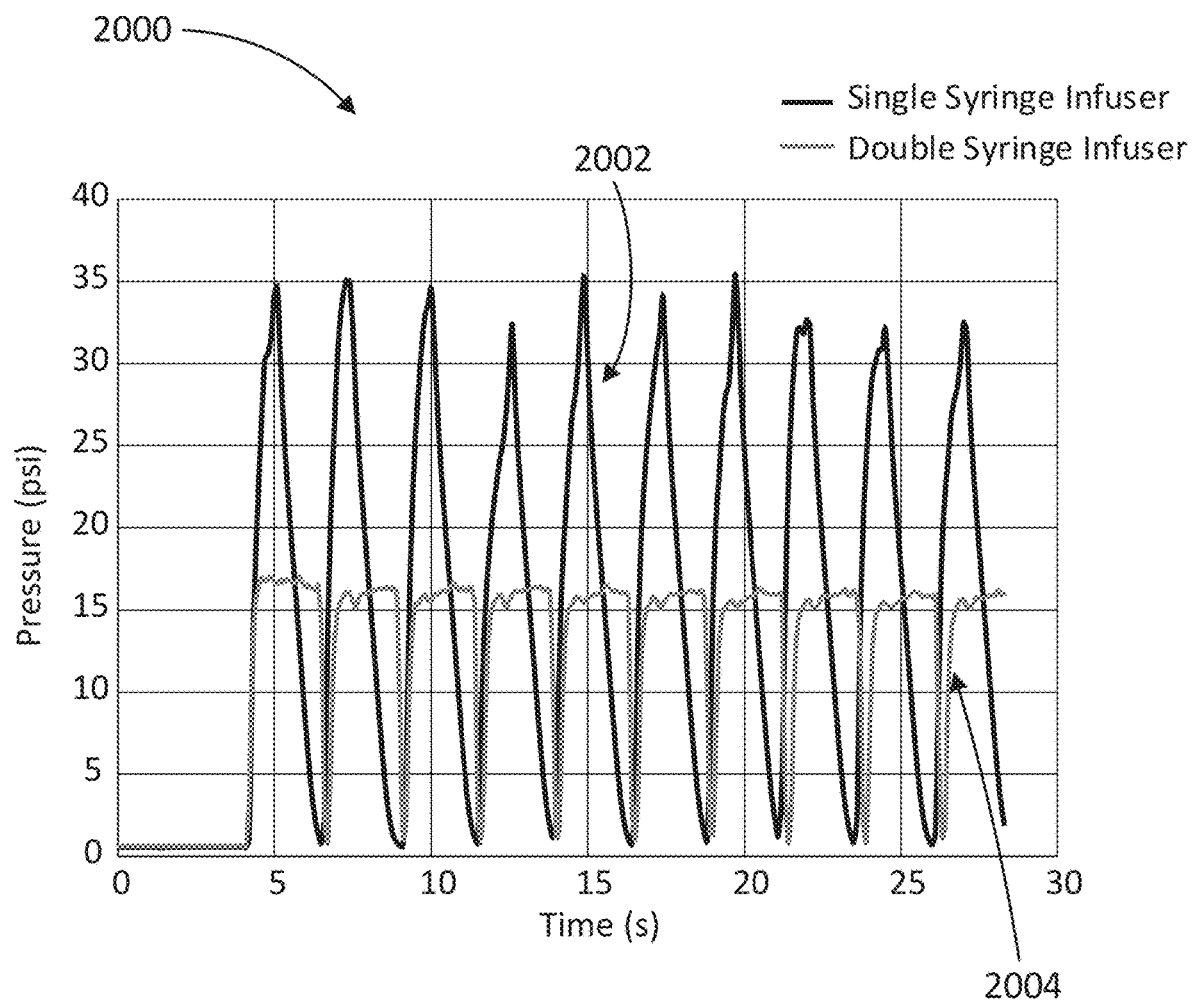
FIG. 23 is a graph showing an example comparison between a pressure profile of a single syringe infusing system and a double syringe infuser, such as any of the double syringe infusers described herein, according to an embodiment.

For example, FIG. 23 shows a graph 2000 demonstrating an example comparison of two pressure profiles over time. The first pressure profile 2002 is associated with a single syringe infuser, and the second pressure profile 2004 is associated with a double syringe infuser, such as any of the systems or devices disclosed herein. For comparison purposes, the single syringe infuser and the double syringe infuser can be operated to deliver fluid through the same diameter catheter or tubing, such as, for example, a 20 G catheter, and can deliver fluid at a sufficient pressure to result in the same overall fluid flow rate (e.g., 250 mL/min). As shown, the first pressure profile 2002 associated with the fluid delivered from the single syringe infuser is highly pulsatile, while the second pressure profile 2004 associated with the fluid delivered from the double syringe infuser is substantially continuous (and substantially non-pulsatile), with lower maximum pressures compared to the single syringe infuser while producing the same or a similar overall fluid delivery rate. Rather than including acute pressure peaks associated with instantaneous fluid flow spikes like those shown in the first pressure profile 2002, the second pressure profile 2004 includes plateaued pressure portions with brief pressure valleys between the plateaued pressure portions, resulting in a substantially continuous flow rate from the double syringe infuser. The brief pressure valleys included in the second pressure profile 2004 can be associated with the transition period between a first syringe transitioning from a delivery to a drawing or filling state and a second syringe transitioning from a drawing or filling state to a delivery state, and vice versa. Thus, the first syringe of the double syringe infuser can be operated to deliver about the same amount of fluid at a lower pressure for about the same time duration as a delivery stroke and a refill stroke of the syringe of the single syringe infuser. Rather than the pressure and flow rate in the output fluid line dropping while the first syringe refills like in a single syringe infuser, the second syringe of the double syringe infuser can be operated to deliver fluid at the same lower pressure as the fluid delivered from the first syringe (for about the same time duration as a delivery stroke and refill stroke of the syringe of the single syringe infuser) while the first syringe of the double syringe infuser refills.

In some embodiments, a system can include a fluid delivery assembly and a drive assembly. The fluid delivery assembly is configured to be releasably mechanically and, optionally, electrically coupled to the drive assembly. When the fluid delivery assembly is releasably coupled to the drive assembly, the drive assembly can control delivery of fluid from the fluid delivery assembly (e.g., to a patient). For example, the drive assembly can be releasably coupled to the fluid delivery assembly to control delivery of fluid from the fluid delivery assembly to provide continuous (e.g., non-pulsatile) fluid flow from the fluid delivery assembly.

In some embodiments, the portable rapid infuser is configured to be handheld, allowing the infuser to be transported easily during and between uses and also providing the user control of the infusion process by allowing them to control the rate of infusion via a variable speed controller. In some embodiments, a display on the infuser gives the user real-time feedback of the volume of fluid delivered, allowing the user to more appropriately treat the patient.

Figure 24:
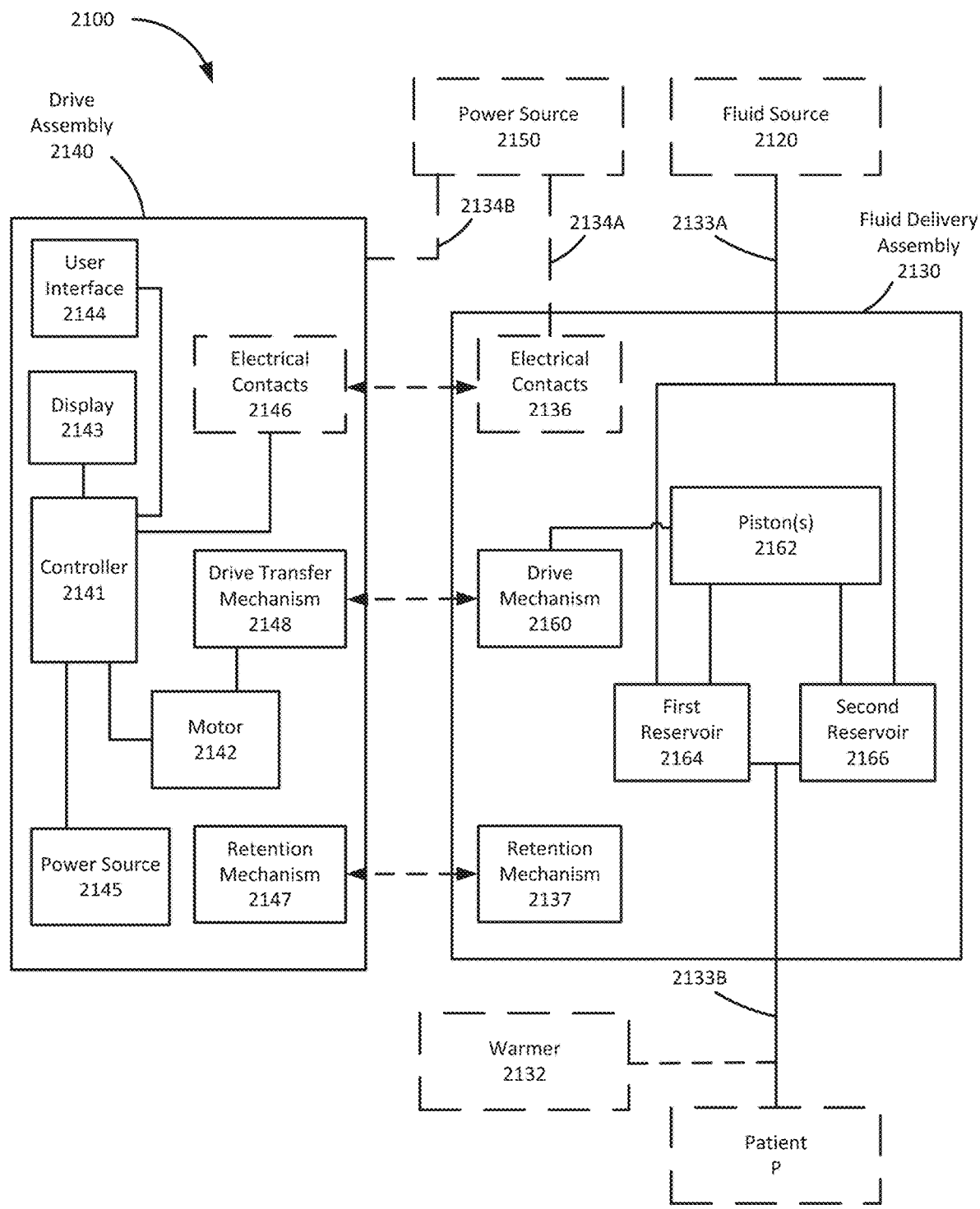
FIG. 24 is a schematic illustration of a system, according to an embodiment.

FIG. 24 is a schematic illustration of a system 2100 (also referred to as an infusion mechanism, an infuser, a rapid infuser, or a dual reservoir infuser). The system 2100 can include a fluid delivery assembly 2130 (also referred to as a disposable tubing assembly or a disposable cartridge assembly) and a drive assembly 2140 (also referred to as a reusable drive unit). The fluid delivery assembly 2130 is configured to be releasably mechanically and, optionally, electrically coupled to the drive assembly 2140. When the fluid delivery assembly 2130 is releasably coupled to the drive assembly 2140, the drive assembly 2140 can control delivery of fluid from the fluid delivery assembly 2130 (e.g., to a patient P). For example, the drive assembly 2140 can be releasably coupled to the fluid delivery assembly 2130 to control delivery of fluid from the fluid delivery assembly 2130 to provide continuous (e.g., non-pulsatile) fluid flow from the fluid delivery assembly 2130. The drive assembly 2140 can be the same or similar in structure and/or function to any of the drive assemblies described herein. The fluid delivery assembly 2130 can be the same or similar in structure and/or function to any of the fluid delivery assemblies described herein, such as the system 100.

The fluid delivery assembly 2130 can be configured to be fluidically coupled to a fluid source 2120 via a fluid line 2133A (e.g., tubing) such that fluid can be drawn from the fluid source 2120. The fluid source 2120 can include one or more fluid containers (e.g., fluid bags) containing, for example, saline or blood. In some embodiments, the fluid source 2120 can be included in the fluid delivery assembly 2130 and/or the system 2100. The fluid delivery assembly 2130 can also include a fluid line 2133B (e.g., tubing) couplable to a patient P such that fluid can be expelled by the fluid delivery assembly 2130 to the patient.

The fluid delivery assembly 2130 includes a drive mechanism 2160, and a fluid pump including one or more pistons 2162, a first reservoir 2164, and a second reservoir 2166. The drive mechanism 2160 is configured to control translation of the one or more pistons 2162 such that, while fluid is being drawn into one of the first reservoir 2164 or the second reservoir 2166, the other reservoir expels fluid, and vice versa. Thus, the drive mechanism 2160 can control the translation of the one or more pistons 2162 to produce substantially continuous flow from the fluid line 2133B. The flow may be substantially non-pulsatile.

The fluid delivery assembly 2130 can include a set of one-way check valves such that fluid can be drawn from the fluid source 2120 into the first reservoir 2164 and the second reservoir 2166, but cannot be expelled from the first reservoir 2164 or the second reservoir 2166 toward the fluid source 2120 via the fluid line 2133A, and so that fluid can be expelled from the first reservoir 2164 and the second reservoir 2166 to the patient P via the fluid line 2133B but not drawn from the fluid line 2133B into the first reservoir 2164 or the second reservoir 2166. Additionally, the check valves can be oriented relative to the first reservoir 2164 and the second reservoir 2166 such that fluid is prevented from being drawn from the first reservoir 2164 into the second reservoir 2166 and vice versa. For example, the fluid delivery assembly 2130 can include four one-way check valves, with a first check valve being disposed along the fluid path from the fluid source 2120 to the first reservoir 2164 (e.g., between the fluid line 2133A and the first reservoir 2164), a second check valve being disposed along the fluid path from the fluid source 2120 to the second reservoir 2166 (e.g., between the fluid line 2133A and the second reservoir 2166), a third check valve disposed along the fluid path from the first reservoir 2164 to the patient P (e.g., between the first reservoir 2164 and the fluid line 2133B), and a fourth check valve disposed along the fluid path from the second reservoir 2166 to the patient P (e.g., between the second reservoir 2166 and the fluid line 2133B). The check valves can be passive valve that do not require external input or control. Thus, fluid flow can be passively controlled, and fluid can flow only one direction through each check valve, regardless of the position or translation direction of each piston of the one or more pistons 2162.

In some embodiments, the drive mechanism 2160 can be operable to translate a first piston of the pistons 2162 to draw fluid from the fluid source 2120 into the first reservoir 2164 via the fluid line 2133A and to simultaneously translate a second piston of the pistons 2162 to expel fluid from the second reservoir 2166 to the patient via the fluid line 2133B. The drive mechanism 2160 can also reverse translation of the first and second pistons of the pistons 2162 to simultaneously draw fluid from the fluid source 2120 into the second reservoir 2166 via the fluid line 2133A and to expel fluid from the first reservoir 2164 to the patient via the fluid line 2133B. For example, in some embodiments, the first reservoir 2164 can be defined by a first syringe and the second reservoir 2166 can be defined by a second syringe. The first syringe can include a first plunger coupled to the first piston and the second syringe can include a second plunger coupled to the second piston. The drive mechanism 2160 can be configured to interact with (e.g., engage with directly or engage with an intermediate transfer component engaged with) the first plunger and the second plunger to control translational movement of the first plunger and the second plunger and, thus, the first piston and the second piston, to draw fluid into and expel fluid from the first reservoir 2164 and the second reservoir 2166, respectively, and vice versa.

In some embodiments, the drive mechanism 2160 can include a drive shaft interface, one or more gears (e.g., pinion gears), one or more racks (e.g., rack gears), and/or one or more driveshafts. For example, in some embodiments, each of the plungers of the first syringe and the second syringe may include or be coupled to a rack gear drivable by a pinion gear. In some embodiments, the fluid delivery assembly 2130 can include a pinion gear coupled to the rack gear of the first syringe and coupled to the rack gear of the second syringe (e.g., disposed between the two rack gears) and configured to be rotated (e.g., clockwise and counterclockwise) to drive one of the rack gears in a first direction and the second rack gear in a second direction opposite the first direction. The pinion gear can define a drive shaft interface configured to receive a drive shaft (e.g., of the drive assembly 2140) such that rotation of the drive shaft causes rotation of the pinion gear. . . . In some embodiments, the fluid delivery assembly 2130 can include two pinion gears, with each pinion gear coupled to one of the two rack gears such that the rack gears can be driven (e.g., forward and backward) by the respective pinion gear. In some embodiments, as described below, rather than including the drive mechanism 2160 (e.g., the pinion gears) in the fluid delivery assembly 2130, the drive mechanism 2160 (e.g., the pinion gears) can be included in the drive assembly 2140 and engageable with the rack gears when the fluid delivery assembly 2130 is properly coupled to the drive assembly 2140.

In some embodiments, the first reservoir 2164 and the second reservoir 2166 can be defined by the same container (e.g., tube) and the fluid delivery assembly 2130 can include only one piston 2162 defining a boundary of the first reservoir 2164 and the second reservoir 2166. The drive mechanism 2160 can be operable to translate the piston 2162 to simultaneously draw fluid from the fluid source 2120 into the first reservoir 2164 via the fluid line 2133A and to expel fluid from the second reservoir 2166 to the patient via the fluid line 2133B, and to translate the piston 2162 in the opposite direction to simultaneously draw fluid from the fluid source 2120 into the second reservoir 2166 via the fluid line 2133A and to expel fluid from the first reservoir 2164 to the patient via the fluid line 2133B. In some embodiments, rather than being only one piston 2162 disposed in the container defining the first reservoir 2164 and the second reservoir 2166, the fluid delivery assembly 2130 can include two pistons within the container coupled together (e.g., via the drive mechanism). In some embodiments, for example, the drive mechanism 2160 can include one or more magnets that can be disposed within the piston 2162 or disposed between two pistons 2162 within the container such that translation of the one or more pistons 2162 can be controlled via magnetic interaction with the one or more magnets of the drive mechanism 2160.

The drive assembly 2140 includes a controller 2141, a motor 2142, and a drive transfer mechanism 2148. The controller 2141 is operably coupled to the motor 2142 and configured to control the motor 2142 to control movement of the drive transfer mechanism 2148. The drive assembly 2140 can also include a display 2143, a user interface 2144, and a power source 2145. The display 2143 can display information about the pumping operation, such as amount of fluid delivered and/or pressure of fluid delivered. The user interface 2144 can allow the user to control fluid flow (e.g., initiation and ceasing of fluid infusion and for parameter adjustment such as flow rate). The power source 2145 can include, for example, a battery. In some embodiments, the user can set the amount of fluid to be delivered (e.g., via the user interface 2144) as a predetermined infusion volume, and does not need to continually engage with the system 2100 for the system 2100 to continue delivering fluid (e.g., the user can set the drive assembly 2140 and fluid delivery assembly 2130 down and walk away). In some embodiments, the user interface 2144 can include a button or trigger that is pressure responsive such that depressing the user interface 2144 more causes the infusion rate to increase. In some embodiments, the infusion rate can be preset and does not change regardless of the pressure applied to the user interface 2144 button or trigger.

The drive transfer mechanism 2148 can be configured to engage (e.g., mechanically or magnetically) with the drive mechanism 2160 (e.g., when the fluid delivery assembly 2130 is coupled to the drive assembly 2140) to control the drive mechanism 2160 (and, thus, the translation of the piston(s) 2162) under the control of the motor 2142. The drive transfer mechanism 2148 can include, for example, one or more drive shafts, one or more gears, and/or a reciprocating magnet. In some embodiments, the drive transfer mechanism 2148 can include or be coupled to strain gauges, a torsion load cell, and/or other force sensing mechanisms (e.g., disposed on one or more shafts such as the one or more drive shafts) such that the controller can identify increases in resistance to rotation (as described in more detail below with respect to FIGS. 34A-34D). In some embodiments, a drive shaft of the drive transfer mechanism 2148 projects from a surface of the drive assembly 2140 and is configured to be engaged with a pinion of the drive mechanism 2160 of the fluid delivery assembly 2130 (e.g., received within a drive shaft receptacle (e.g., an opening) of the pinion such that rotation of the drive shaft by the motor 2142 causes rotation of the pinion). The controller 2141 can control the motor 2142 such that the motor 2142 alternates between rotating the drive shaft in a first direction and in a second direction opposite the first direction (e.g., by the motor 2142 first spinning in a first direction and then spinning in a second direction under control of the controller 2141). In some embodiments, the drive transfer mechanism includes one or more pinion gears projecting from a surface of the drive assembly 2140 and configured to engage with gears (e.g., rack gears) associated with the first reservoir 2164 and the second reservoir 2166, respectively such that the motor 2142 can control motion of the rack gears via the pinion gears of the drive transfer mechanism 2148 to control fluid delivery of the fluid delivery assembly 2130. The controller 2141 can control the motor 2142 such that the motor 2142 alternates between rotating the one or more pinion gears in a first direction and in a second direction opposite the first direction (e.g., by the motor 2142 being operatively coupled to the one or more pinion gears such as via a drive shaft and first spinning in a first direction and then spinning in a second direction under control of the controller 2141). In some embodiments, the drive transfer mechanism 2148 includes an interrupted bevel gear and two driven gears couplable to the interrupted bevel gear and mounted on a drive shaft of the drive transfer mechanism 2148. The interrupted bevel gear can have teeth disposed on only a portion of a perimeter of the interrupted bevel gear (e.g., less than half of the perimeter) such that the teeth of the interrupted bevel gear only engage with one of the two driven gears at any time. The motor 2142 can operate to cause rotation of the interrupted bevel gear in one direction, and the teeth of the interrupted bevel gear can alternate contact with each of two driven gears such that the drive shaft of the drive transfer mechanism 2148 is alternatingly rotated in a first direction and a second direction depending on which driven gear is engaged with the teeth of the interrupted bevel gear. When the drive shaft is coupled to or engaged with the drive mechanism 2160 (e.g., coupled to or engaged with a pinion of the drive mechanism 2160), plungers coupled to the drive mechanism 2160 (e.g., via rack gears) can be continuously translated in alternating directions. In embodiments in which the piston(s) 2162 include or are coupled to one or more magnets such that the pistons can be translationally urged via magnetic interaction, the drive transfer mechanism 2148 can include one or more magnets configured to be reciprocated along a travel path by the motor 2142 and configured such that the piston(s) are translated under control of the one or more magnets of the drive transfer mechanism 2148 when the drive assembly 2140 and the fluid delivery assembly 2130 are coupled.

As shown in FIG. 24, the fluid delivery assembly 2130 can include a retention mechanism or feature 2137 and the drive assembly 2140 can include a complementary retention mechanism or feature 2147. The retention mechanism 2137 and the retention mechanism 2147 can be configured to engage with each other to ensure that the fluid delivery assembly 2130 and the drive assembly 2140 are maintained in a coupled orientation relative to each other until the fluid delivery procedure has ended (e.g., to prevent accidental decoupling). The retention mechanism 2137 and the retention mechanism 2147 can include, for example, a mechanical latch and complementary detent, one or more magnetic connections, or any other suitable coupling mechanism(s). In some embodiments, the retention mechanism 2137 and/or the retention mechanism 2147 can include or also function as alignment features to ensure proper alignment between the fluid delivery assembly 2130 and the drive assembly 2140 for a fluid delivery procedure. In some embodiments, the system 2100 can include separate alignment features (not shown) configured to encourage, urge, and/or maintain proper alignment between the fluid delivery assembly 2130 and the drive assembly 2140. In some embodiments, the retention mechanisms 2137, 2147 and/or the alignment features can include posts and receiving holes for the posts, projections and one or more receiving grooves for the projections, projections which trap a portion of the other assembly between the projections, or any other suitable features which prevent rotation of the fluid delivery assembly 2130 relative to the drive assembly 2140 when the drive transfer mechanism 2148 is providing torque to the drive mechanism 2160.

In some embodiments, the fluid delivery assembly 2130 can be coupled to a warmer 2132 (also referred to as a warmer assembly) via the fluid line 2133B such that fluid delivered from the fluid delivery assembly 2130 can be warmed above a threshold temperature or to a temperature within a threshold temperature range prior to and/or for delivery to the patient. In some embodiments, the warmer 2132 can include a heating element and a heat exchanger. In some embodiments, the warmer 2132 can include tubing (e.g., disposable tubing) that can be coupled to an end of the fluid line 2133B such that fluid can flow from the fluid line 2133B, into the tubing of the warmer 2132, and away from a heating element and/or heat exchanger of the warmer toward or to the patient via the tubing of the warmer 2132. In some embodiments, the fluid line 2133B can be coupled to or engaged with the warmer 2132 such that fluid traveling through the fluid line 2133B can be heated by the warmer 2132 while in the fluid line 2133B prior to reaching a patient. In some embodiments, the warmer 2132 can include a power source, which can be, for example, a rechargeable battery. In some embodiments, in addition to or as an alternative to the power source, the warmer 2132 can be configured to receive operational power and/or charging power for the power source via an electrical connection from the drive assembly 2140, the fluid delivery assembly 2130, and/or an AC power source such as a wall outlet. In some embodiments, the system 2100 does not include the warmer 2132. In some embodiments, any of the systems described herein can include or be coupled to a warmer such as the warmer 2132. In some embodiments, the warmer 2132 can be included in the fluid delivery assembly 2130.

Optionally, the fluid delivery assembly 2130 can include electrical contacts 2136 and the drive assembly 2140 can include electrical contacts 2146 configured to be aligned with the electrical contacts 2136 when the drive assembly 2140 and the fluid delivery assembly 2130 are coupled. The electrical contacts 2136, 2146 can include, for example, pogo pins and a plate, a pin configured to be received within a receptacle, and/or two metal plates configured to directly contact each other with or without a spring force. In some embodiments, the fluid delivery assembly 2130 can be configured to provide operational power and/or charging power to the drive assembly 2140 via the electrical contacts 2136 and the electrical contacts 2146. For example, the fluid delivery assembly 2130 can be configured to be coupled to a power source 2150 via an electrical connection 2134A such that power can be drawn from the power source 2150 via the electrical connection 2134A and delivered to the drive assembly 2140 via the electrical contacts 2136 and the electrical contacts 2146. The power source 2150 can include, for example, an AC power source (e.g., a wall outlet) and/or an external battery. Additionally, in some embodiments, data can be transferred between the fluid delivery assembly 2130 and the drive assembly 2140 via the electrical contacts 2136 and the electrical contacts 2146 such that, for example, identification information can be received by the drive assembly 2140 and used to determine, for example, motor speed based on pumping parameters associated with the identification information. In some embodiments, the power source 2150 can be configured to be coupled to the drive assembly 2140 and configured to provide operational power and/or charging power to the drive assembly 2140. For example, the power source 2150 can be coupled to the drive assembly 2140 (e.g., to the electrical contacts 2146 and/or to the power source 2145) via an electrical connection 2134B. In some embodiments, the power source 2150 can be configured to be coupled to the warmer 2132 via an electrical connection (not shown) and/or via the drive assembly 2140 and/or the fluid delivery assembly 2130. The electrical connections described herein can be any suitable electrical coupling, such as an electrical contact, wire, or power cord. In some embodiments, the power source 2150 can include a charger base configured to be electrically and mechanically coupled to the fluid delivery assembly 2130, the drive assembly 2140, and/or the warmer 2132 such that charging power and/or operational power can be provided to the drive assembly 2140 and/or the warmer 2132. The charger base can be coupled to an AC power source (e.g., a wall outlet) to increase a stored power level of a power source included in the charger base via an electrical connection (e.g., a plug). The charger base can also include electrical contacts and/or an electrical connection such as an elongated wire or plug configured to electrically couple the power source included in the charger base with the drive assembly 2140 and/or the warmer 2132 to provide power from the power source to the drive assembly 2140 and/or the warmer 2132 (e.g., during and/or prior to use of the system 2100).

In use, the fluid delivery assembly 2130 can be coupled to the drive assembly 2140 such that the drive transfer mechanism 2148 and the drive mechanism 2160 are operably coupled. In some embodiments, the fluid delivery assembly 2130 can be coupled to the drive assembly 2140 such that the electrical contacts 2136 are aligned with the electrical contacts 2146 and/or such that the retention mechanism 2137 is engaged with the retention mechanism 2147. The fluid line 2133A can be fluidically coupled to a fluid source 2120 (e.g., via an IV tubing spike) and can be fluidically coupled to one or more blood filters and/or chambers disposed in line with the fluid source 2120 and the fluid line 2133A. The fluid line 2133B can be fluidically coupled to a patient (e.g., a patient's vasculature) via, for example, a luer lock connector attached to a patient's IV access. The drive assembly 2140 can then initiate operation of the motor 2142 (under control of the user via the user interface 2144) such that the piston(s) 2162 are translated by the drive mechanism 2160 under control of the drive transfer mechanism 2148 to alternatingly dispense fluid from the first reservoir 2164 and the second reservoir 2166 while alternatingly drawing fluid into the second reservoir 2166 and the first reservoir 2164, respectively. In some embodiments, some or all of the components of the system 2100 can be included in a kit, such as a kit including a box or bag and including any suitable number of fluid (e.g., blood or saline) bags and the components or a subset of the components of the system 2100.

Figure 25:
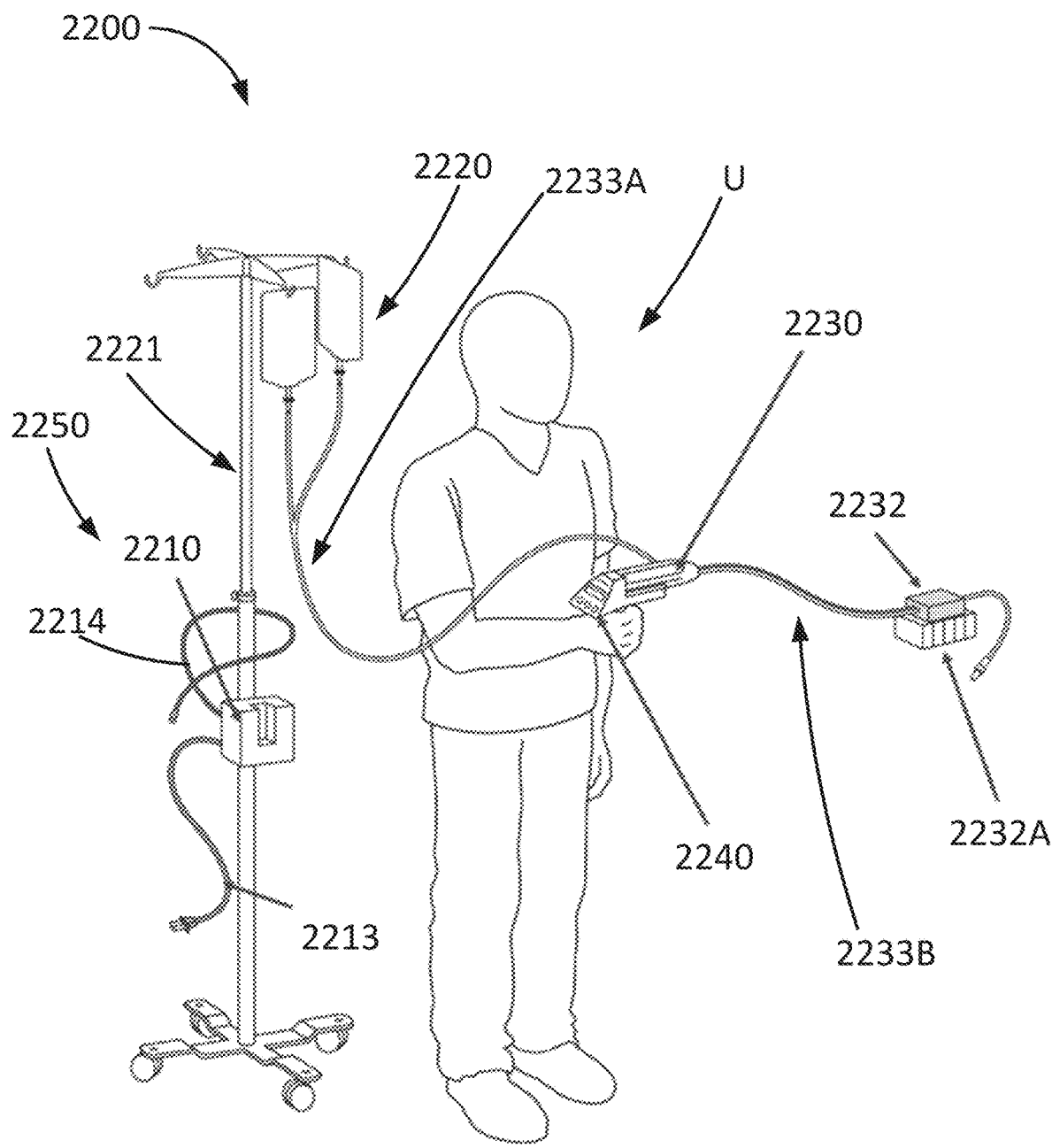
FIG. 25 is a schematic illustration of a system, according to an embodiment.

FIG. 25 is a schematic illustration of a system 2200. The system 2200 can be the same or similar in structure and/or function to any of the systems described herein, such as the system 22100. For example, the system 2200 includes a fluid delivery assembly 2230 and a drive assembly 2240 that can be the same or similar in structure and/or function to any of the fluid delivery assemblies and drive assemblies, respectively, described herein. FIG. 25 shows a user U (e.g., a healthcare practitioner) holding a grip portion of the drive assembly 2240. The fluid delivery assembly 2230 is coupled to a fluid source 2220 hanging from an IV pole 2221 via a fluid line 2233A. Although the fluid source 2220 is shown as including two fluid bags, in some embodiments the fluid source 2220 can include any suitable number of or type of fluid containers. The fluid delivery assembly 2230 is fluidically coupled to a fluid line 2233B via which fluid can be delivered from the fluid delivery assembly 2230.

As shown in FIG. 25, the fluid delivery assembly 2230 can be coupled to a warmer 2232 (also referred to as a warmer assembly) via the fluid line 2233B such that fluid delivered from the fluid delivery assembly 2230 can be warmed above a threshold temperature or to a temperature within a threshold temperature range prior to and/or for delivery to the patient. The warmer 2232 can be the same or similar in structure and/or function to any of the warmers described herein, such as the warmer 22132. In some embodiments, the warmer 2232 can include a heating element and a heat exchanger. In some embodiments, the warmer 2232 can include tubing (e.g., disposable tubing) that can be coupled to an end of the fluid line 2233B such that fluid can flow from the fluid line 2233B, into the tubing of the warmer 2232, and away from a heating element and/or heat exchanger of the warmer toward or to the patient via the tubing of the warmer 2232. In some embodiments, the fluid line 2233B can be coupled to or engaged with the warmer 2232 such that fluid traveling through the fluid line 2233B can be heated by the warmer 2232 while in the fluid line 2233B prior to reaching a patient. As shown in FIG. 25, the warmer 2232 can include a power source 2232A, which can be, for example, a rechargeable battery. In some embodiments, in addition to or as an alternative to the power source 2232A, the warmer 2232 can be configured to receive operational power and/or charging power for the power source 2232A via an electrical connection from the drive assembly 2240, the fluid delivery assembly 2230, an AC power source such as a wall outlet, and/or a power source 2250 including a charger base 2210 (described below). In some embodiments, the system 2200 does not include the warmer 2232.

The power source 2250 that can be the same or similar in structure and/or function to any of the power sources described herein. The power source 2250 can include the charger base 2210, which is configured to be electrically and mechanically coupled to the fluid delivery assembly 2230, the drive assembly 2240, and/or the warmer 2232 such that charging power and/or operational power can be provided to the drive assembly 2240 and/or the warmer 2232. The charger base 2210 can be coupled to an AC power source (e.g., a wall outlet) to increase a stored power level of a power source (e.g., a rechargeable battery) included in the charger base 2210 via an electrical connection 2213 (e.g., a plug). The charger base 2210 can also include electrical contacts and/or an electrical connection 2214 (e.g., an elongated wire or plug) configured to electrically couple the power source included in the charger base 2210 with the drive assembly 2240 and/or the warmer 2232 to provide power from the power source to the drive assembly 2240 and/or the warmer 2232 (e.g., during and/or prior to use of the system 2200). In some embodiments, the charger base 2210 can define a recess configured to receive a portion of the drive assembly 2240 to hold and/or charge the drive assembly 2240 between uses. In some embodiments, as shown on FIG. 25, the charger base 2210 can be mounted on the IV pole 2221.

Figure 26A:
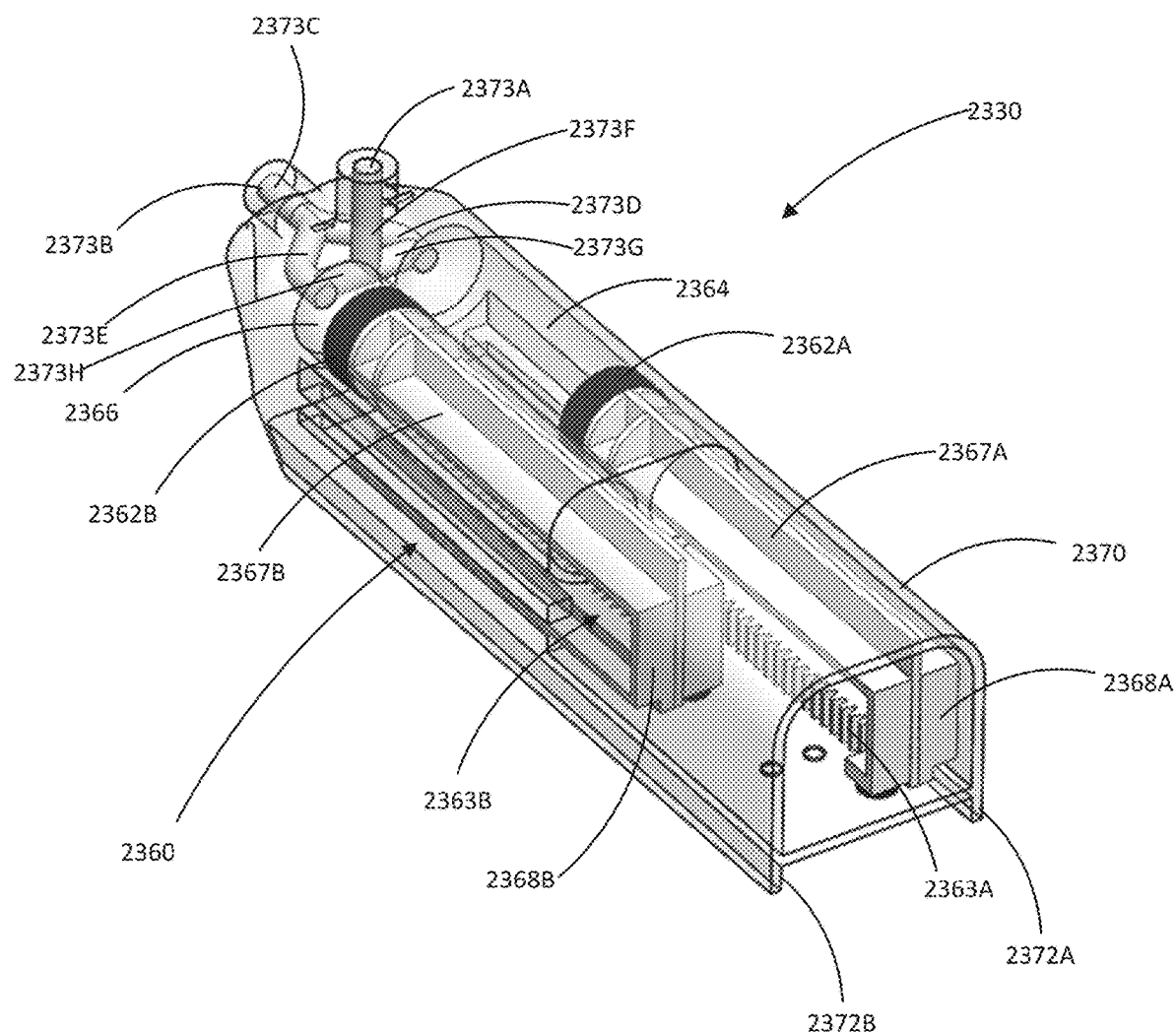
FIGS. 26A-26D are various views of a fluid delivery assembly in various stages of operation, according to an embodiment.
Figure 26B:
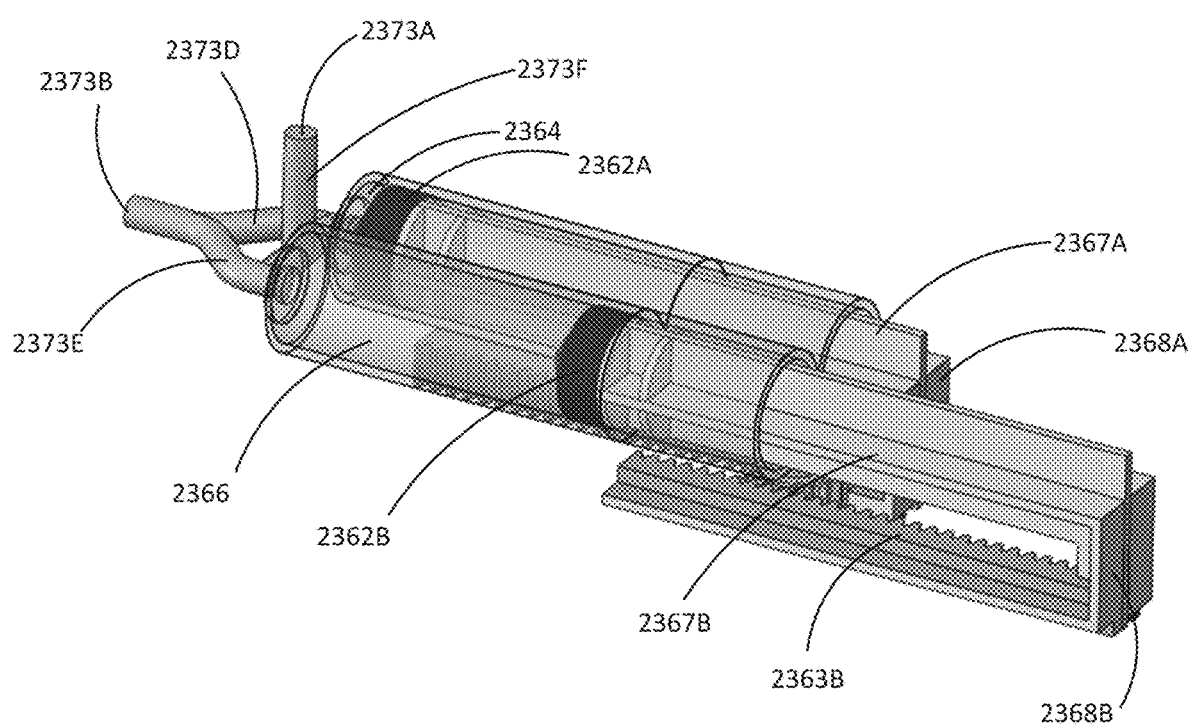
Figure 26C:
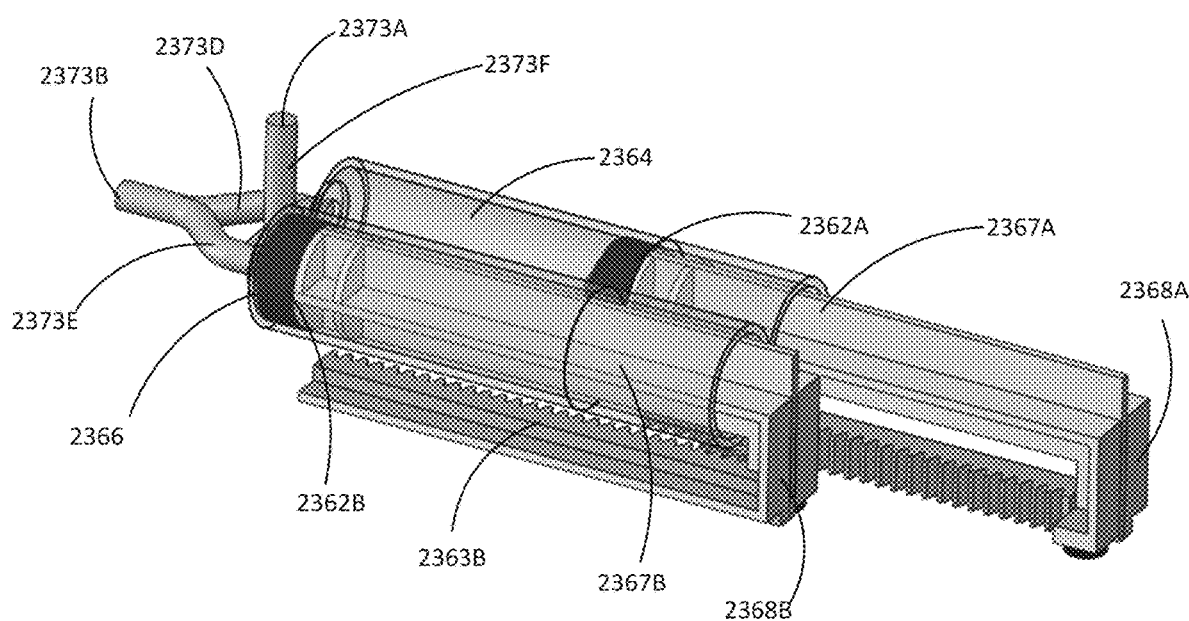
Figure 26D:
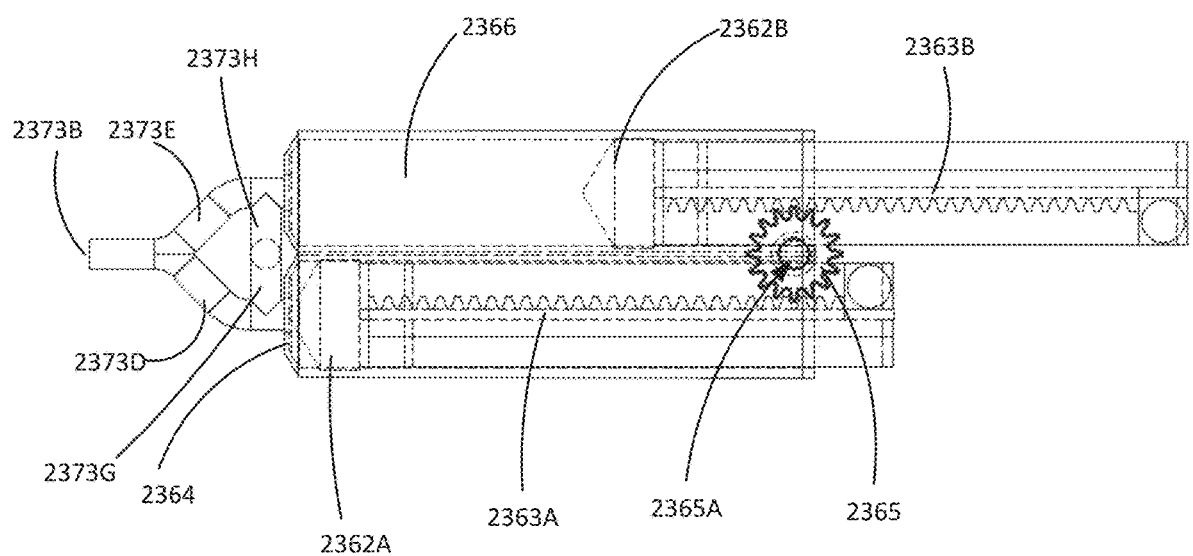

FIGS. 26A-26D are various views of a fluid delivery assembly 2330 in various stages of operation. Specifically, FIG. 26A is a perspective view of the fluid delivery assembly 2330 in a first configuration, and FIGS. 26B and 26D are a perspective view and a bottom view, respectively, of the fluid delivery assembly 2330 in a second configuration. FIG. 26C is a perspective view of the fluid delivery assembly 2330 in a third configuration. FIG. 26A shows the fluid delivery assembly 2330 having a housing 2370, and in FIGS. 26B-26D the housing 2370 is not shown. The fluid delivery assembly 2330 can be the same or similar in structure and/or function to any of the fluid delivery assemblies described herein, such as the fluid delivery assembly 2130. For example, the fluid delivery assembly 2330 includes a drive mechanism 2360, and a fluid pump including a first piston 2362A, a second piston 2362B, a first reservoir 2364, and a second reservoir 2366.

The fluid delivery assembly 2330 also includes a fluid inlet 2373A and a fluid outlet 2373B configured such that fluid can be drawn from a fluid source (e.g., the fluid source 2120) into the first reservoir 2364 and the second reservoir 2366 via the fluid inlet 2373A (e.g., via a fluid line fluidically coupling the fluid source to the fluid inlet 2373A such as the fluid line 2133A) and dispensed to a patient via the fluid outlet 2373B (e.g., via a fluid line fluidically coupled to the fluid outlet 2373B such as the fluid line 2133B). The fluid inlet 2373A can be coupled to each of the first reservoir 2364 and the second reservoir 2366 via any suitable lumen(s) or passageways (e.g., via tubing defining lumen(s) or passageways(s)). For example, as shown in FIG. 26A, the fluid outlet 2373B can be formed at the end of an outlet passageway 2373C fluidically coupled to a first end of a first fluid passageway 2373D and a first end of a second fluid passageway 2373E. The second end of the first fluid passageway 2373D can be coupled to an inlet of the first reservoir 2364 and the second end of the second fluid passageway 2373E can be coupled to an inlet of the second reservoir 2366. The fluid inlet 2373A can be formed at the end (upstream) of an inlet passageway 2373F that is fluidically coupled to a third fluid passageway 2373G and a fourth fluid passageway 2373H. The third fluid passageway 2373G can be coupled to the first fluid passageway 2373D and the fourth fluid passageway 2373H can be coupled to the second fluid passageway 2373E.

Although not shown, a set of passive check valves can be disposed relative to the fluid inlet 2373A and the fluid outlet 2373B (e.g., within the passageways described above) to control the direction of fluid flow relative to the fluid source and the patient. For example, a check valve can be disposed within the inlet passageway 2373F such that fluid can flow from the fluid inlet 2373A into the first reservoir 2364 (via the third fluid passageway 2373G and the end of the first fluid passageway 2373D) and into the second reservoir 2366 (via the fourth fluid passageway 2373H and the end of the second fluid passageway 2373E), but fluid cannot flow from the first reservoir 2364 and the second reservoir 2366 out of the fluid inlet 2373A. Alternatively or additionally, check valves can be disposed within the third fluid passageway 2373G and the fourth fluid passageway 2373H to prevent fluid flow to the inlet passageway 2373F. For example, a check valve can be disposed within the third fluid passageway 2373G and within the fourth fluid passageway 2373H. To prevent fluid from being drawn from the fluid outlet 2373B into the first reservoir 2364 and the second reservoir 2366, a check valve can be disposed within the outlet passageway 2373C and/or within the first fluid passageway 2373D and the second fluid passageway 2373E downstream of the couplings with the third fluid passageway 2373G and with the fourth fluid passageway 2373H.

As shown in FIG. 26A, the first reservoir 2364, the second reservoir 2366, the first piston 2362A, the second piston 2362B, and at least a portion of the drive mechanism 2360 can be disposed within the common housing 2370. Additionally, as shown in FIG. 26A, the fluid inlet 2373A and the fluid outlet 2373B, along with the passageways fluidically coupling the fluid inlet 2373A and the fluid outlet 2373B to the first reservoir 2364 and the second reservoir 2366, can be included within or defined by the housing 2370. In some embodiments, although not shown, the fluid inlet 2373A, the fluid outlet 2373B, and the associated passageways can be disposed outside of the housing 2370 and coupled to the housing 2370 and/or the first reservoir 2364 and the second reservoir 2366. As shown in FIG. 26A, the housing 2370 can include retention and/or alignment features, such as a first projecting flange 2372A and a second projecting flange 2372B (also referred to as "fins") that project from a lower surface of the housing 2370 such that the housing 2370 defines a space between the first projecting flange 2372A and the second projecting flange 2372B configured to receive a portion of a drive assembly. The first projecting flange 2372A and the second projecting flange 2372B can retain the drive assembly between the first projecting flange 2372A and the second projecting flange 2372B such that, when a pinion gear 2365 (described below) of the fluid delivery assembly 2330 is rotated under control of a drive assembly, the housing 2370 will not rotate relative to the drive assembly. The first projecting flange 2372A can be disposed parallel to the second projecting flange 2372B. As shown, in some embodiments, each of the first projecting flange 2372A and the second projecting flange 2372B can extend from a first end to a second end of the housing 2370. In some embodiments, the first projecting flange 2372A and the second projecting flange 2372B can extend only a portion of a distance between the first end and the second end of the housing 2370. In some embodiments, the first projecting flange 2372A and the second projecting flange 2372B can each include discrete flange portions.

The drive mechanism 2360 includes a single pinion gear 2365, a first rack gear 2363A, a first plunger 2367A, a second rack gear 2363B, and a second plunger 2367B. The first plunger 2367A is configured to translate the first piston 2362A within the first reservoir 2364 and the second plunger 2367B is configured to translate the second piston 2362B within the second reservoir 2366. The first plunger 2367A is coupled to the first rack gear 2363A and the second plunger 2367B is coupled to the second rack gear 2363B such that movement of the first rack gear 2363A causes corresponding movement of the first plunger 2367A and movement of the second plunger 2367B causes corresponding movement of the second plunger 2367B. For example, as shown in FIG. 26A, the first plunger 2367A can be coupled to the first rack gear 2363A via a proximal end connector 2368A and the second plunger 2367B can be coupled to the second rack gear 2363B via a proximal end connector 2368B. In some embodiments, one or both of the first plunger 2367A and the second plunger 2367B can be coupled to any portion of the first rack gear 2363A and the second rack gear 2363B, respectively, that does not interfere with engagement between the pinion gear 2365 and teeth of the first rack gear 2363A and the second rack gear 2363B (e.g., an upper surface).

The first rack gear 2363A and the teeth of the second rack gear 2363B are disposed such the teeth of the first rack gear 2363A face the teeth of the second rack gear 2363B. The pinion gear 2365 is disposed between the first rack gear 2363A and the second rack gear 2363B such that the pinion gear 2365 is engaged with teeth of each of the first rack gear 2363A and the second rack gear 2363B and can simultaneously translate each of the first rack gear 2363A and the second rack gear 2363B along parallel translation paths. Thus, the pinion gear 2365 can drive the first plunger 2367A and the second plunger 2367B via engagement with the first rack gear 2363A and the second rack gear 2363B, respectively. The pinion gear 2365 can be rotated in a first direction (e.g., counterclockwise when viewed from the bottom as shown in FIG. 26D) to drive the first rack gear 2363A in a first direction (e.g., proximally) and the second rack gear 2363B in a second direction (e.g., distally) opposite the first direction such that the first piston 2362A is pulled proximally to draw fluid into the first reservoir 2364 and, simultaneously, the second piston 2362B is pushed distally to expel fluid from the second reservoir 2366. The pinion gear 2365 can be rotated in a second direction (e.g., clockwise when viewed from the bottom) to drive the second rack gear 2363B in the first direction (e.g., proximally) and the first rack gear 2363A in the second direction (e.g., distally) such that the second piston 2362B is pulled proximally to draw fluid into the second reservoir 2366 and, simultaneously, the first piston 2362A is pushed distally to expel fluid from the first reservoir 2364. Thus, while one of the first reservoir 2364 and the second reservoir 2366 is filling, the other of the first reservoir 2364 and the second reservoir 2366 can be expelling, and vice versa.

For example, in FIG. 26C, the fluid delivery assembly 2330 is in a configuration (referred to above as a third configuration) in which the first plunger 2367A and the second plunger 2367B are disposed such that the first reservoir 2364 is at a maximum volume and the second reservoir 2366 is at a minimum volume. In FIGS. 26B and 26D, the fluid delivery assembly 2330 is in a second configuration in which the first plunger 2367A and the second plunger 2367B are disposed such that the first reservoir 2364 is at a minimum volume and the second reservoir 2366 is at a maximum volume. FIG. 26A shows the fluid delivery assembly 2330 in a configuration (referred to above as a first configuration) in which the first plunger 2367A and the second plunger 2367 are between the ends of their respective translation paths and the first reservoir 2364 and the second reservoir 2366 are between their minimum and maximum volumes, with the first reservoir 2364 being closer to its maximum volume and the second reservoir 2366 being closer to its minimum volume.

The pinion gear 2365 can be transitioned (e.g., under control of a drive assembly such as the drive assembly 2140) between rotating in the first direction and rotating in the second direction at intervals such that the pinion gear 2365 transitions rotational direction when each of the first plunger 2367A and the second plunger 2367B reach opposite ends of their respective strokes. The pinion gear 2365 defines an opening 2365A configured to receive a drive shaft configured to rotate the pinion gear 2365 in the first direction and the second direction. For example, the opening can have a perimeter shaped to receive a drive shaft having a complementary shape or a shape configured to engage with teeth projecting into the opening such that the pinion gear 2365 does not rotate relative to the drive shaft when the drive shaft is disposed within the opening.

Figure 27A:
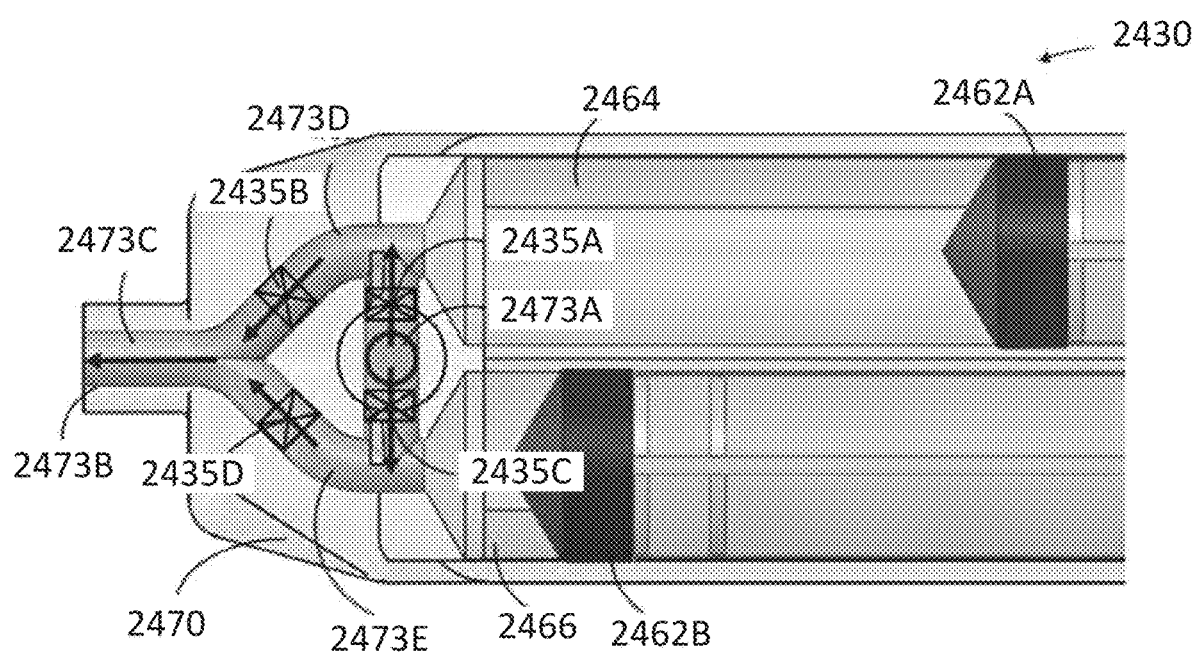
FIGS. 27A and 27B are a top view and a perspective view of a front portion a fluid delivery assembly, according to an embodiment.
Figure 27B:
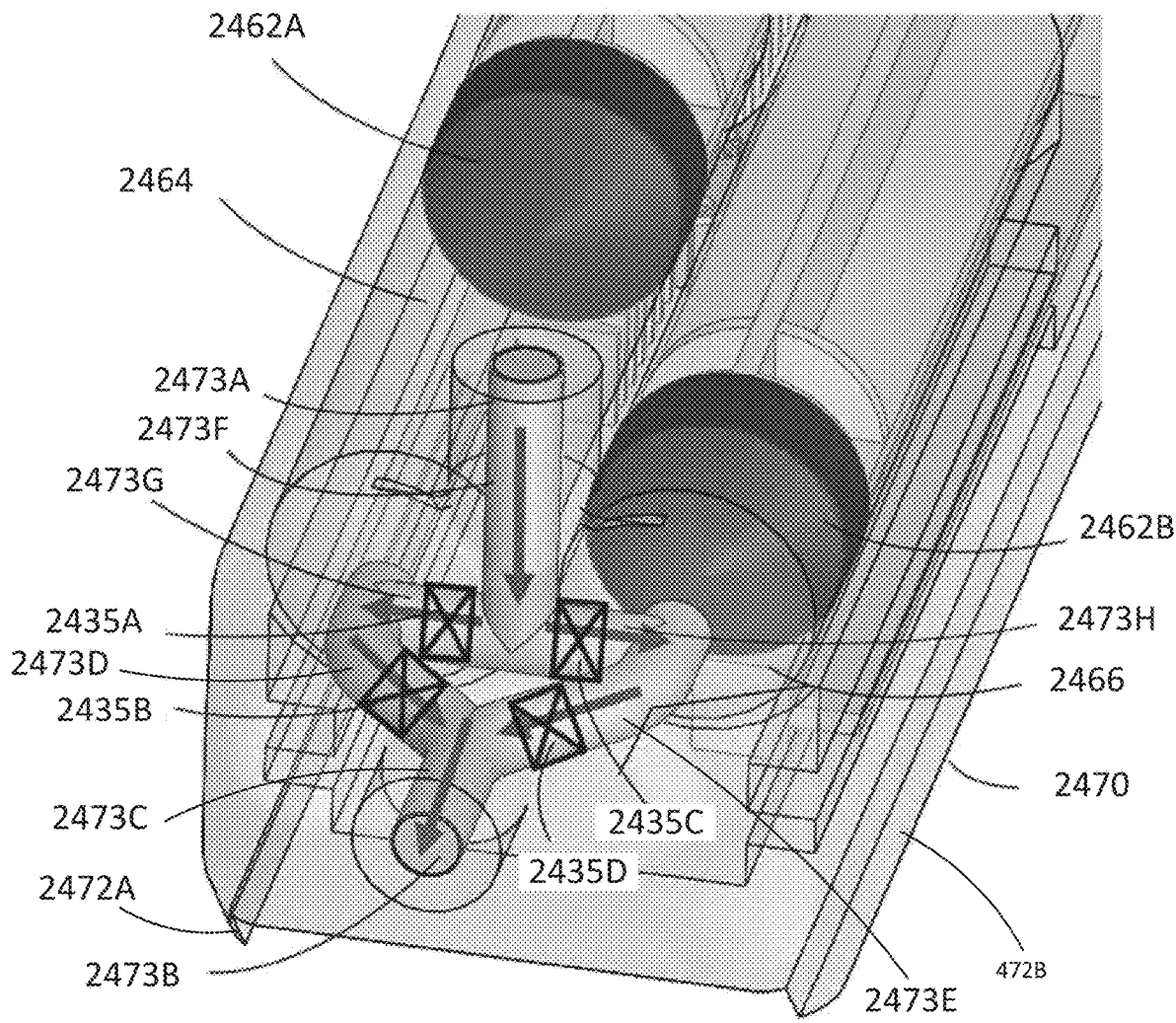

FIGS. 27A and 27B are a top view and a perspective view of a front portion a fluid delivery assembly 2430. The fluid delivery assembly 2430 can be the same or similar in structure and/or function to any of the fluid delivery assemblies described herein, such as the fluid delivery assembly 330 described above with respect to FIGS. 26A-26D. For example, the fluid delivery assembly 2430 includes a housing 2470, a first reservoir 2464, a second reservoir 2466, a first piston 2462A, a second piston 2462B. The housing 2470 can include retention and/or alignment features, such as a first projecting flange 2472A and a second projecting flange 2472B that project from a lower surface of the housing 2470. Additionally, the fluid delivery assembly 2430 includes a fluid inlet 2473A and a fluid outlet 2473B configured such that fluid can be drawn from a fluid source (e.g., the fluid source 2120) into the first reservoir 2464 and the second reservoir 2466 via the fluid inlet 2473A (e.g., via a fluid line fluidically coupling the fluid source to the fluid inlet 2473A such as the fluid line 2133A) and dispensed to a patient via the fluid outlet 2473B (e.g., via a fluid line fluidically coupled to the fluid outlet 2473B such as the fluid line 2133B). The fluid outlet 2473B can be formed at the end of an outlet passageway 2473C fluidically coupled to a first end of a first fluid passageway 2473D (also referred to as a fluid path or fluid line) and a first end of a second fluid passageway 2473E (also referred to as a fluid path or fluid line). The second end of the first fluid passageway 2473D can be coupled to an inlet of the first reservoir 2464 and the second end of the second fluid passageway 2473E can be coupled to an inlet of the second reservoir 2466. The fluid inlet 2473B can be formed at the end of an inlet passageway 2473F that is fluidically coupled to a third fluid passageway 2473G (also referred to as a fluid path or fluid line) and a fourth fluid passageway 2473H (also referred to as a fluid path or fluid line). The third fluid passageway 2473G can be coupled to the first fluid passageway 2473D and the fourth fluid passageway 2473H can be coupled to the second fluid passageway 2473E.

FIGS. 27A and 27B include schematic boxes representing locations of one-way check valves 2435A, 2435B, 2435C, 2435D along flow paths relative to the first reservoir 2464 and the second reservoir 2464. The embodiment shown in FIGS. 27A and 27B includes four one-way check valves, with a first check valve 2435A being disposed along the fluid path 2473G between the fluid inlet 2473A and the first reservoir 2464 (e.g., between the fluid line 2473F and the first reservoir 2464) and a third check valve 2435C being disposed along the fluid path 2473H between the fluid inlet 2473A and the second reservoir 2466 (e.g., between the fluid line 2473F and the second reservoir 2466). The first check valve 2435A functions such that fluid may flow through the fluid line 2473G toward the first reservoir 2464 beyond the first check valve 2435A and enter the first reservoir 2464, but no fluid may return from the first reservoir 2464 backwards into the fluid line 2473G beyond the first check valve 2435A toward the fluid inlet 2473A. The third check valve 2435C functions such that fluid may flow through the fluid line 2473H toward the second reservoir 2466 beyond the third check valve 2435C and enter the second reservoir 2466, but no fluid may return from the second reservoir 2466 backwards into the fluid line 2473H beyond the third check valve 2435C toward the fluid inlet 2473A. The second check valve 2435B is disposed along the fluid path 2473D and the fourth check valve 2435D is disposed along the fluid path 2473E. The second check valve 2435B allows fluid to exit the first reservoir 2464 and flow through the fluid outlet 2473B, but prevents fluid from traveling to the first reservoir 2464 from the fluid outlet 2473B or from the second reservoir 2466. The fourth check valve 2435D allows fluid to exit the second reservoir 2464 and flow through the fluid outlet 2473B, but prevents fluid from traveling to the second reservoir 2466 from the fluid outlet 2473B or from the first reservoir 2464. In some embodiments, the check valves 2435A-2435D can function passively, and can include a flapper valve, a ball valve, or other suitable one-way check valve.

Figure 28A:
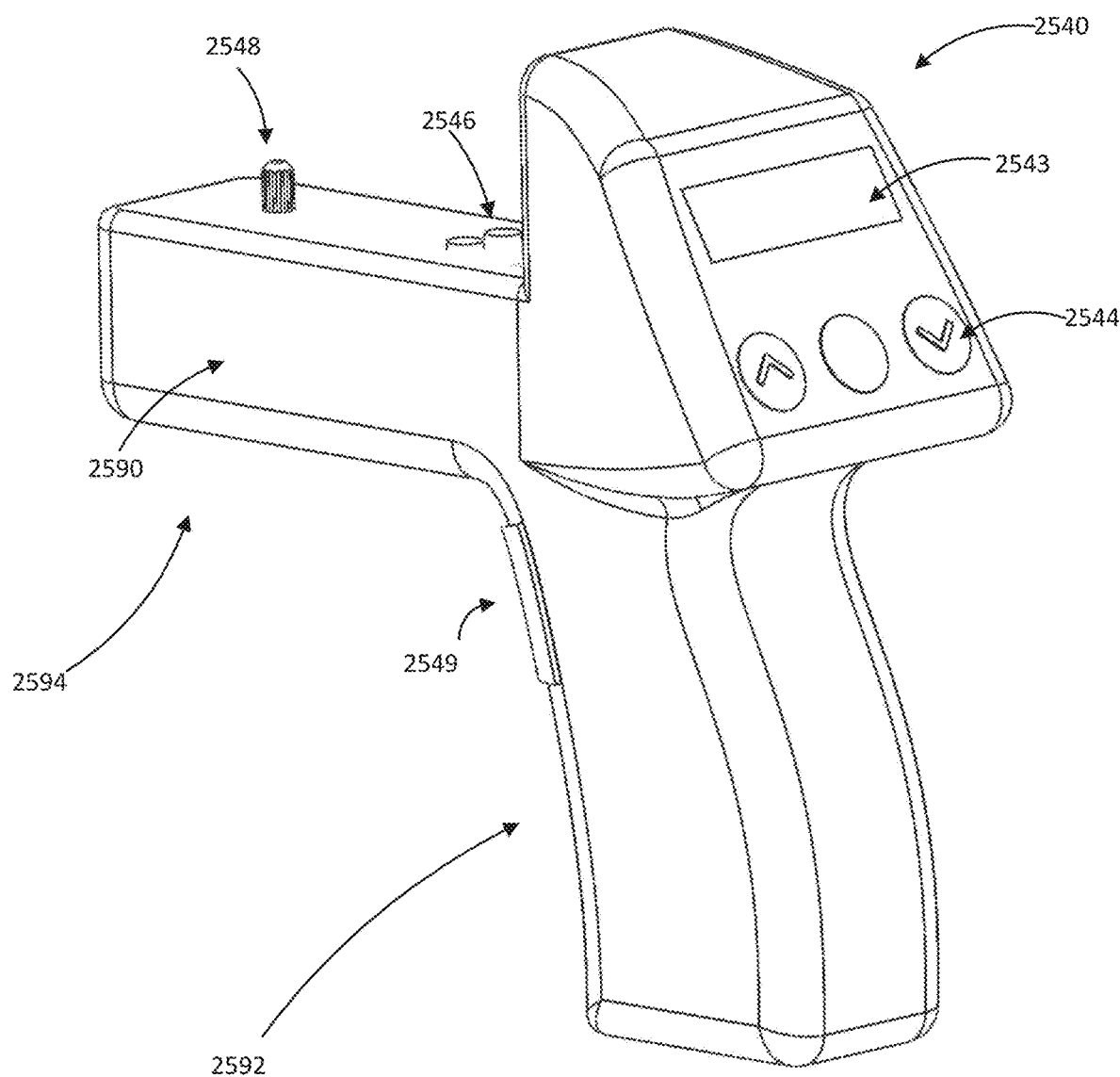
FIGS. 28A and 28B are illustrations of a perspective view and a side view of a drive assembly, according to an embodiment.
Figure 28B:
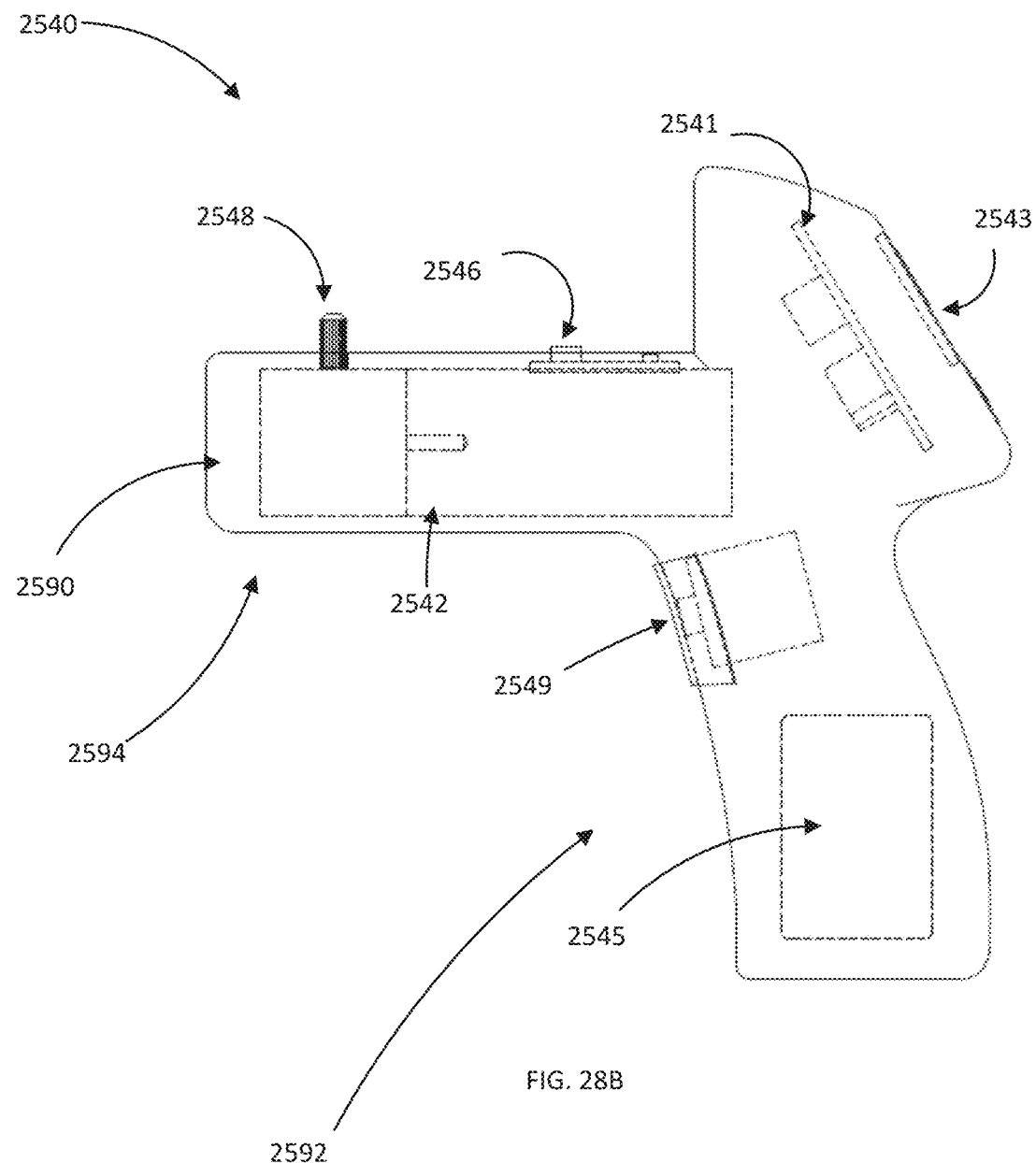

FIGS. 28A and 28B are illustrations of a perspective view and a side view of a drive assembly 2540 (also referred to as a portable rapid infuser or an infuser), with a housing 2590 of the drive assembly 2540 shown as being transparent in FIG. 28B. The drive assembly 2540 can be the same or similar in structure and/or function to any of the drive assemblies described herein, such as the drive assembly 2140 described above. For example, the drive assembly 2540 includes a controller 2541, a motor 2542, and a drive transfer mechanism 2548 (also referred to as a driveshaft). The motor 2542 is configured to provide mechanical power to rotate the drive transfer mechanism 2548. The controller 2541 is operably coupled to the motor 2542 and configured to control the motor 2542 to control movement of the drive transfer mechanism 2548 (e.g., rotational direction and speed). The drive assembly 2540 can also include a display 2543 and a power source 2545 (e.g., a battery) configured to provide operational power to the other components of the drive assembly 2540 (e.g., the motor 2542, the controller 2541, and the display 2543). The display 2543 can display information about the pumping operation, such as a real-time updated total amount of fluid delivered and/or real-time pressure of fluid delivered. The drive assembly 2540 can include one or more user interface features, such as a control mechanism 2549 (e.g., a button or a dial) and user interface buttons 2544 (e.g., disposed on a surface of the housing 2590 including the display 2543). The user interface features can allow the user to control fluid flow (e.g., initiation and ceasing of fluid infusion and for parameter adjustment such as flow rate).

The drive assembly 2540 is configured to be handheld and portable, allowing the drive assembly 2540 to be transported easily during and between uses. As shown in FIG. 28A, the housing 2590 of the drive assembly 2540 can include a grip portion 2592 extending away from a fluid delivery assembly engagement portion 2594 such that a user can grip the grip portion 2592 during use of the drive assembly 2540. The control mechanism 2549 can be disposed on a distal portion of the grip portion 2592 such that, when a user is gripping the grip portion 2592, an index finger of the user can rest upon the control mechanism 2549. In some embodiments, the user can initiate operation of the motor 2552 to start fluid infusion via engagement with the control mechanism 2549 (e.g., via pressing on the control mechanism 2549) and can cease operation of the motor 2552 to stop fluid infusion via disengaging with the control mechanism 2549 (e.g., via releasing the control mechanism 2549). In some embodiments, the control mechanism 2549 can be a variable speed control mechanism 2549 such that the speed of the motor 2552 and, thus, the speed of the driveshaft 2548 and the rate of fluid infusion, can depend on the amount of engagement between the user's finger and the variable speed control mechanism 2549 (e.g., based on the amount of pressure applied and/or the distance the control mechanism 2549 is depressed relative to an initial position). In some embodiments, the user interface buttons 2544 can be used to set and/or change a rate of fluid infusion, and the control mechanism 2549 can be used to start and stop fluid infusion. Although not shown, in some embodiments, the user interface buttons 2544 can be accessible by a user's thumb while the user is holding the grip portion 2592 and has an index finger in contact with the control mechanism 2549.

The driveshaft 2548 is operatively coupled to the motor 2542 and projects upward from an upper surface of the fluid delivery assembly engagement portion 2594 such that the driveshaft 2548 can be engaged with (e.g., received by) a drive mechanism of a fluid delivery assembly, such as by any of the drive mechanisms described herein. For example, the driveshaft 2548 can have any suitable shape such that the driveshaft 2548 can couple to (e.g., be inserted into an opening of) a pinion gear, such as the pinion gear 2365 described above with respect to the drive mechanism 2360, and the pinion gear will rotate under control of the motor 2542 due to rotation of the driveshaft 2548. For example, the driveshaft 2548 can include ribs, teeth, or any suitable non-circular shape (e.g., octagonal, hexagonal, square) such that the driveshaft 2548 can be disposed within the opening of the pinion gear and rotate the pinion gear. Thus, a fluid delivery assembly, such as any of the fluid delivery assemblies described herein (e.g., fluid delivery assembly 2130 or fluid delivery assembly 330) can be coupled to the drive assembly 2540 by vertically translating the fluid delivery assembly 2530 into engagement with an upper surface of the fluid delivery assembly engagement portion 2594 such that the driveshaft 2548 is inserted into an opening of a pinion gear of the fluid delivery assembly to operably couple the motor 2542 to the drive mechanism of the fluid delivery assembly. With the driveshaft 2548 coupled to the drive mechanism of the fluid delivery assembly, the drive assembly 2540 can control translation of one or more pistons of the fluid delivery assembly (e.g., the first piston 2362A and the second piston 2362B simultaneously) relative to reservoirs of the fluid delivery assembly. In some embodiments, the drive assembly 2540 can be formed such that the drive assembly 2540 is easily cleanable with minimal crevices within which fluids and/or debris can be trapped. For example, the outer surface of the drive assembly 2540 (e.g., the housing 2590) can include only flat and/or rounded surfaces and no sharp corners.

The drive assembly 2540 can also include electrical contacts 2546 that are electrically coupled to the controller 2541 and allow the drive assembly 2540 to interface with electrical contacts of a fluid delivery assembly, such as any of the fluid delivery assemblies described herein (e.g., the fluid delivery assembly 2130). The electrical contacts 2546 can be located, for example, on the upper surface of the fluid delivery assembly engagement portion 2594 such that, when a fluid delivery assembly is coupled to the drive assembly 2540, electrical contacts of the fluid delivery assembly align with and contact the electrical contacts 2546. The electrical contacts 2546 allow for data and/or power to be transmitted between the drive assembly 2540 and a fluid delivery assembly. The electrical contacts 2546 can include, for example, pogo pins configured to contact a plate of a fluid delivery device, a plate configured to contact pogo pins of a fluid delivery device, a pin configured to be received within a receptacle of a fluid delivery device, a receptacle configured to receive a pin of a fluid delivery device, and/or a metal plate configured to directly contact a metal plate of a fluid delivery device with or without a spring force.

Figure 29A:
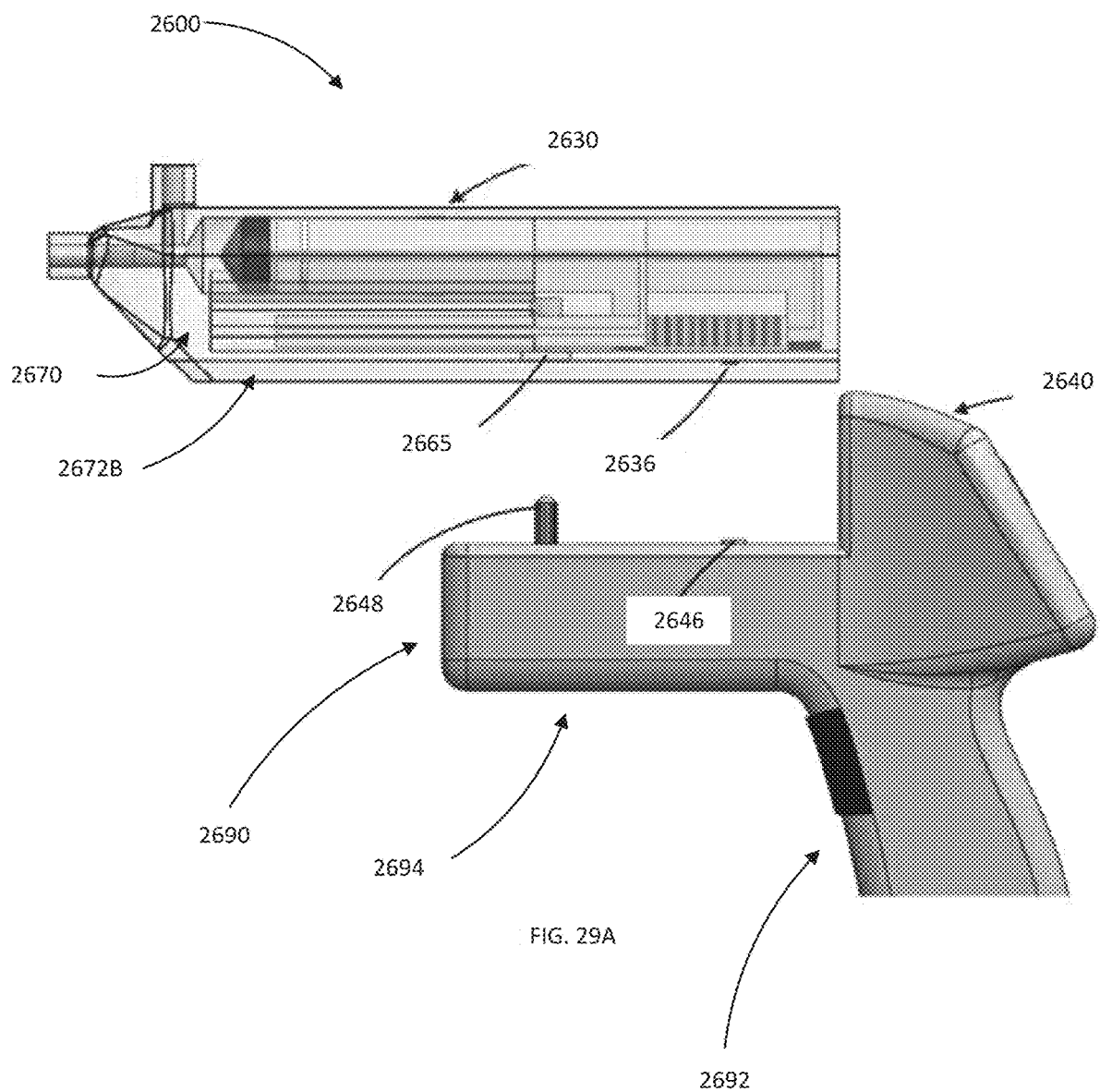
FIGS. 29A and 29B are illustrations of side views of a fluid delivery system in a first configuration and a second configuration, respectively, according to an embodiment.
Figure 29B:
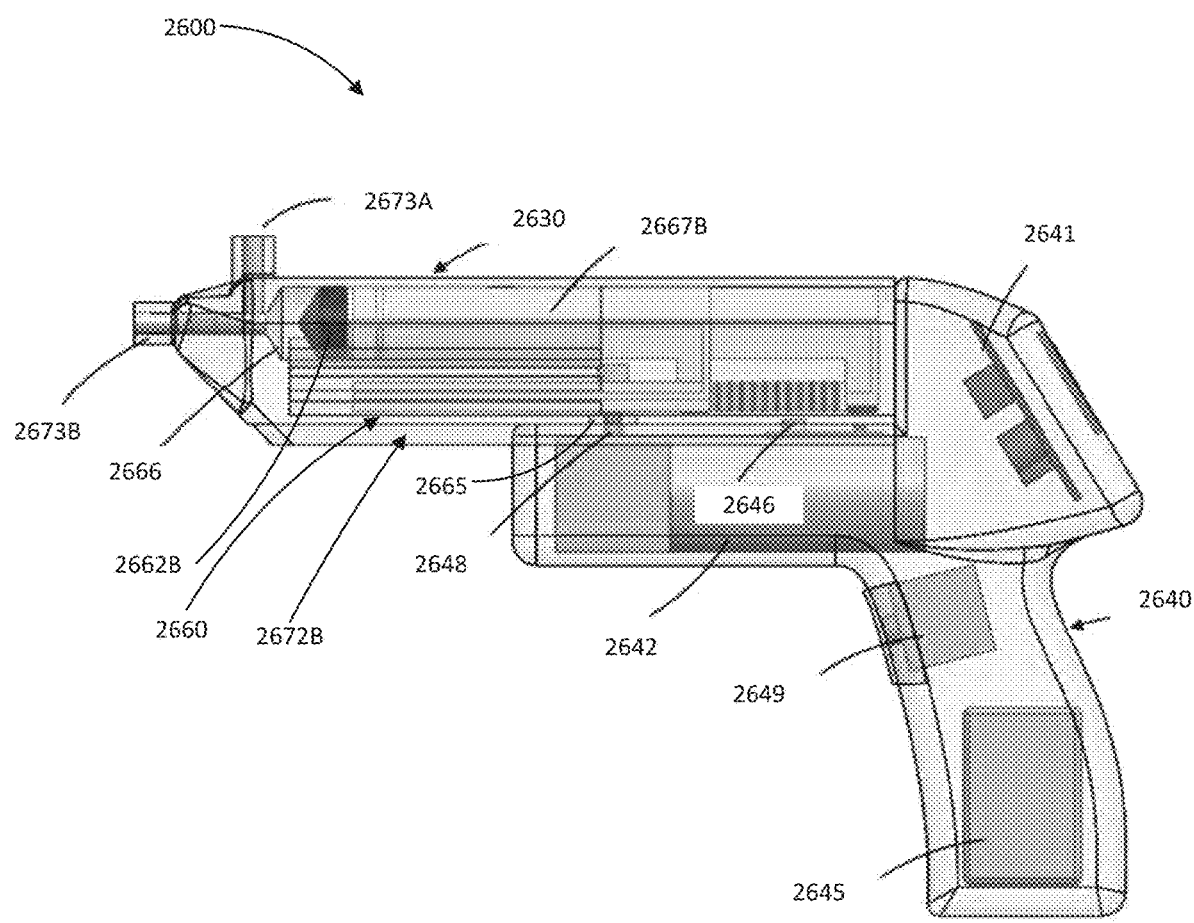
Figure 29C:
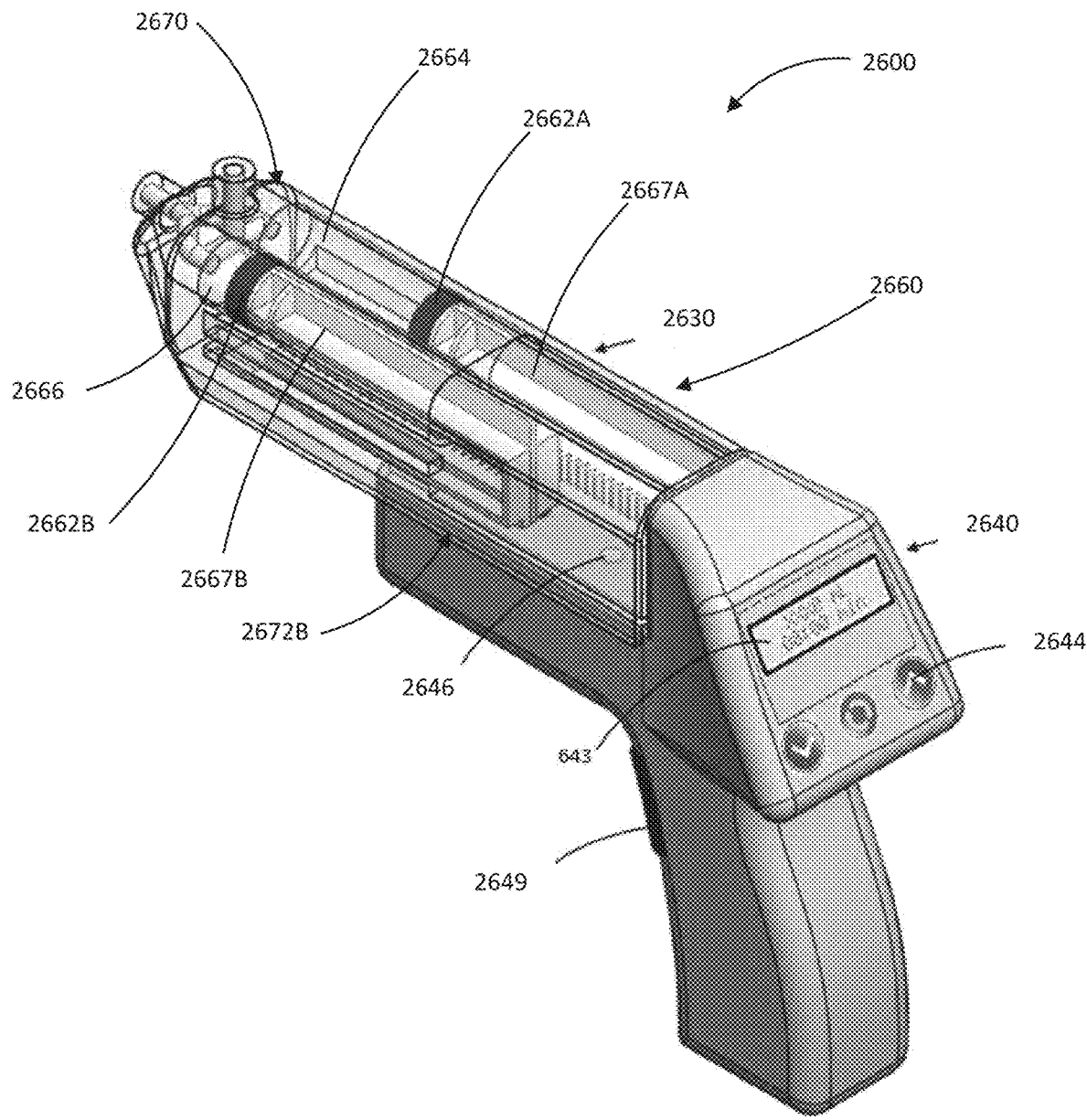
FIG. 29C is a perspective view of the fluid delivery system in the second configuration.

FIGS. 29A and 29B are side views of a fluid delivery system 2600 (also referred to as an infusion mechanism) in a first configuration and a second configuration, respectively. FIG. 29C is a perspective view of the fluid delivery system 2600 in the second configuration. The fluid delivery system 2600 can be the same or similar in structure and/or function to any of the fluid delivery systems described herein. For example, the fluid delivery system includes a fluid delivery assembly 2630 and a drive assembly 2640. The fluid delivery assembly 2630 that can be the same or similar in structure and/or function to the fluid delivery assembly 2330 and the drive assembly 2640 that can be the same or similar in structure and/or function to the drive assembly 2540. For example, the fluid delivery assembly 2630 includes a housing 2670, a fluid inlet 2673A, a fluid outlet 2673B, a first reservoir 2646, a second reservoir 2666, a first piston 2662A, a second piston 2662B, a first plunger 2667A, and a second plunger 2667B. The housing 2670 includes a first projecting flange 2672A and a second projecting flange 2672B (also referred to as "fins") that can be the same or similar in structure and/or function to any of the projecting flanges described herein. The fluid delivery assembly 2630 also includes electrical contact(s) 2636. The drive assembly 2640 includes a housing 2690 (including a grip portion 2692 and a fluid delivery assembly engagement portion 2694), a controller 2641, a motor 2642, and a drive transfer mechanism 2648 (also referred to as a driveshaft), a display 2643, and a power source 2645. The drive assembly 2640 also includes one or more user interface features, such as a control mechanism 2649 (e.g., a button or a dial) and user interface buttons 2644 (e.g., disposed on a surface of the housing 2690 including the display 2643). The drive assembly 2640 also includes electrical contact(s) 2646.

FIG. 29A shows the fluid delivery system 2600 in the first configuration with the fluid delivery assembly 2630 decoupled from the drive assembly 2640, and FIGS. 29B and 29C show the fluid delivery system 2600 in the second configuration with the fluid delivery system 2630 coupled to the drive assembly 2640. The fluid delivery assembly 2630 (also referred to as a disposable tubing assembly or a disposable cartridge assembly) can be easily coupled to the drive assembly 2640 (also referred to as a reusable drive unit) and decoupled and separated from the drive assembly 2640 by a user. Prior to use of the system 2600 to deliver a fluid infusion, the fluid delivery assembly 2630 can be releasably coupled to the drive assembly 2640. FIG. 29A shows the system prior to being coupled. FIG. 29B shows the system after the drive assembly 2640 and the fluid delivery assembly 2630 are coupled. The coupling of the drive assembly 2640 and the fluid delivery assembly 2630 includes one or more of the following connections being made: an upper portion of the fluid delivery assembly engagement portion 2694 of the drive assembly 2640 is received into a space defined between the first projecting flange 2672A and the second projecting flange 2672B such that the upper portion of the drive assembly 2640 including the drive transfer mechanism 2648 is encapsulated and the housing 2670 is prevented from rotating relative to the drive assembly 2640, a retention mechanism (not shown) on the drive assembly 2640 can mechanically and releasably couple to a retention mechanism on the fluid delivery assembly 2630 (e.g., a mechanical latch mechanism), the drive transfer mechanism 2648 of the drive assembly 2640 mechanically couples to the pinion 2665 of the drive mechanism 2660 of the fluid delivery assembly 2630, and the electrical contact(s) 2646 of the drive assembly 2640 connects electrically to the electrical contact(s) 2636 of the fluid delivery assembly 2630. In some embodiments, as shown in FIGS. 29A and 29B, the system 2600 is configured such that movement of the fluid delivery assembly 2630 in one direction relative to the drive assembly 2640 results in the drive shaft 2648 coupling to the pinion 2665 and the electrical contact(s) 2646 coupling to the electrical contact(s) 2636 (e.g., simultaneously or near simultaneously). For example, the fluid delivery assembly 2630 can be translated downward from the position shown in FIG. 29A into contact with the drive assembly 2640 as shown in FIG. 29B such that the fluid delivery assembly 2630 is mechanically and electrically coupled to the drive assembly 2640.

Figure 30A:
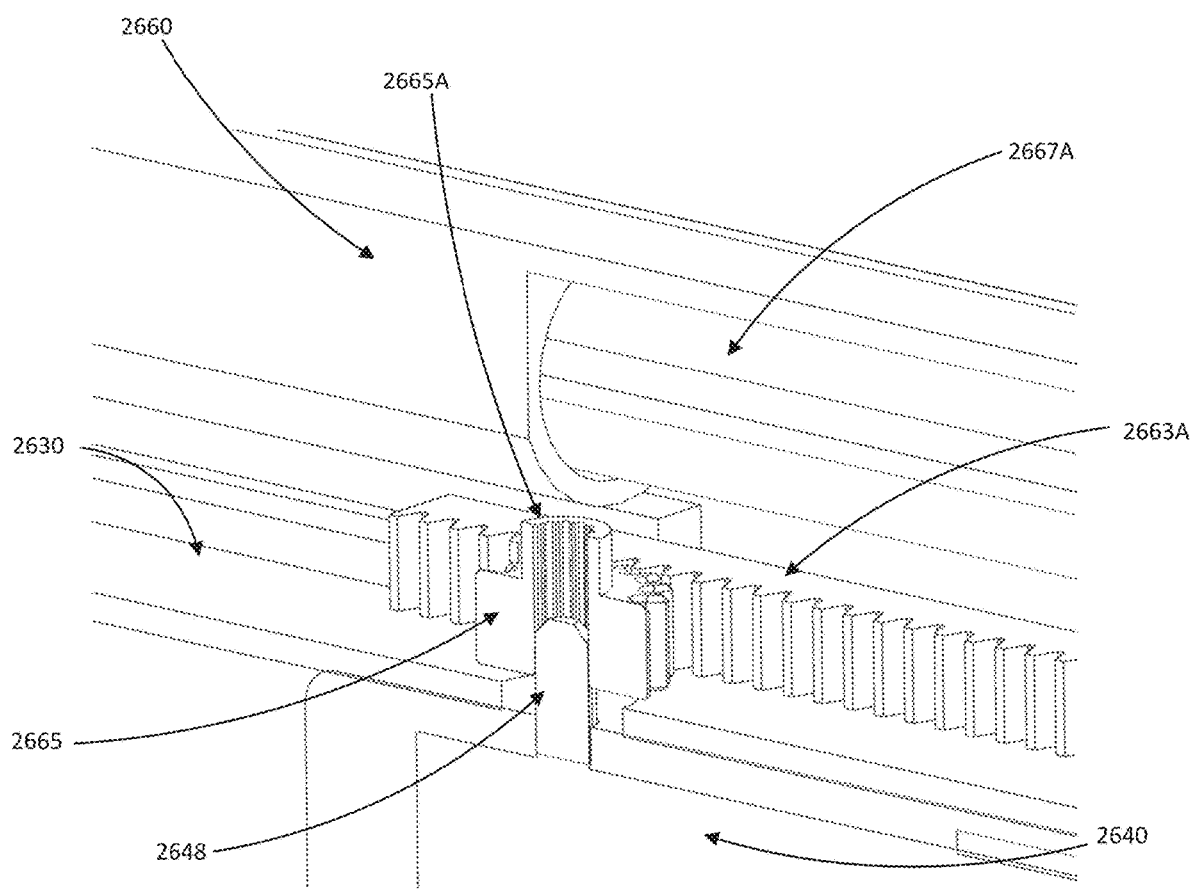
FIG. 30A-30C are various views of a drive mechanism of a disposable tubing assembly and a drive transfer mechanism of a drive assembly of the fluid delivery system of FIGS. 29A-29C.
Figure 30B:
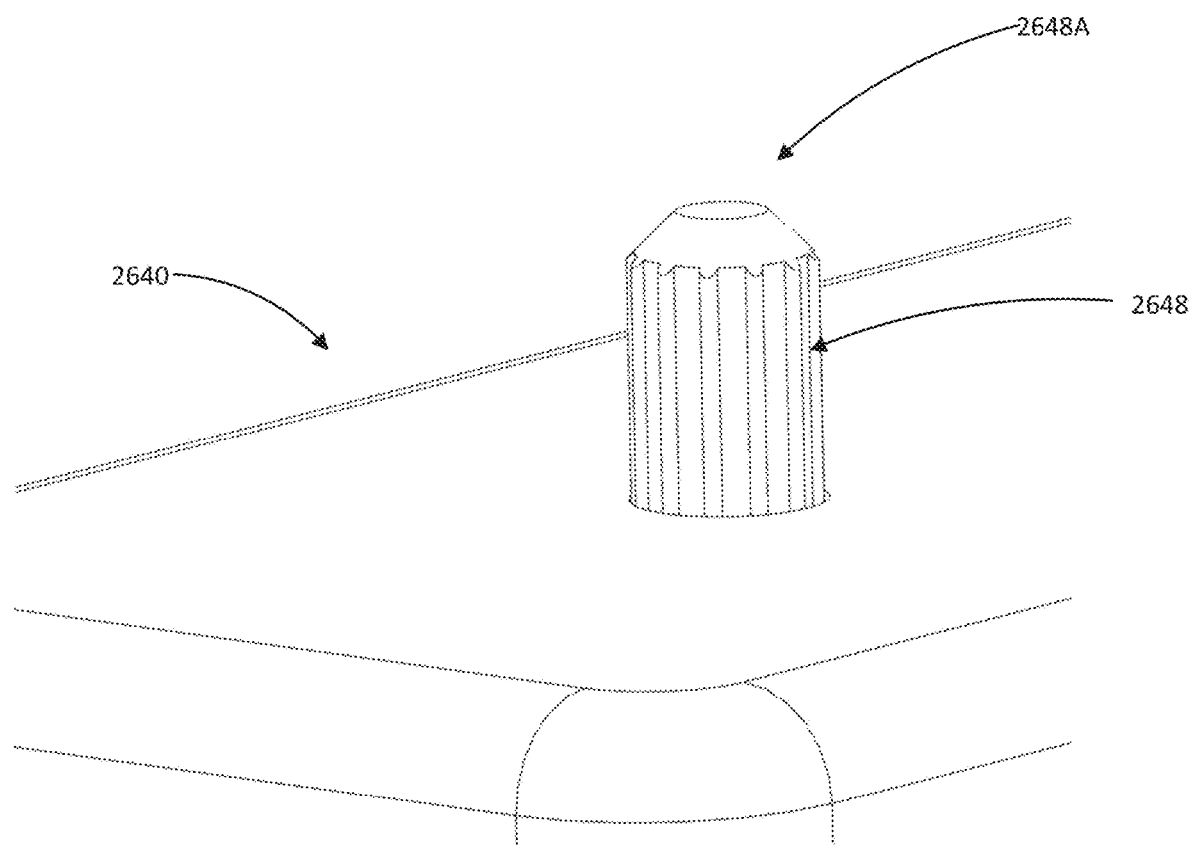
Figure 30C:
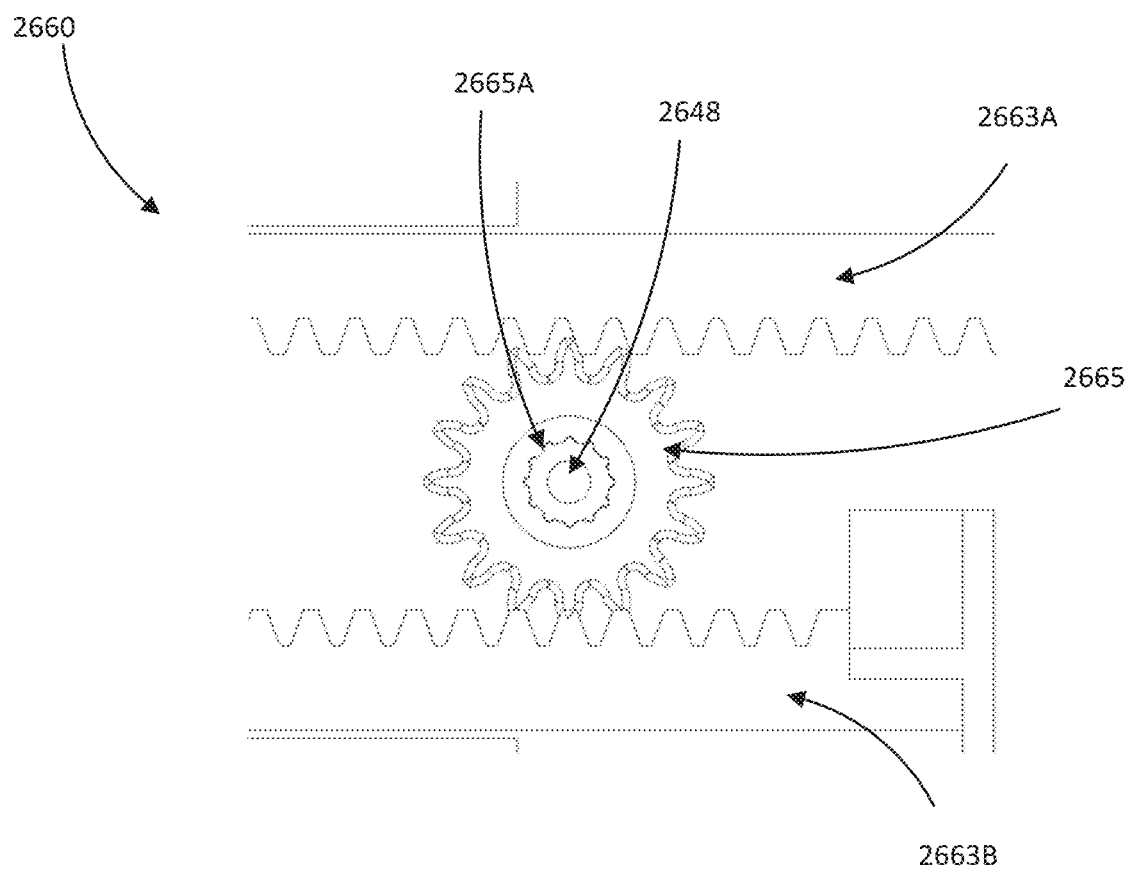

FIGS. 30A-30C are various views of the drive mechanism 2660 of the disposable tubing assembly 2630 and the drive transfer mechanism 2648 of the drive assembly 2640. FIG. 30A is a perspective view of a cross-section of the drive transfer mechanism 2648 engaged with and disposed within the opening 2665A of the pinion 2665. FIG. 30B is a perspective view of the portion of the drive transfer mechanism 2648 extending from an upper surface of the drive assembly 2640. FIG. 30C is a top view of a portion of the drive mechanism 2660 of the disposable tubing assembly 2630 mated with the drive transfer mechanism 2648. In some embodiments, as shown, the pinion gear 2665 can define a drive transfer mechanism interface defining the opening 2665A configured to receive the drive transfer mechanism 2648 such that rotation of the drive transfer mechanism 2648 causes rotation of the pinion gear 2665. In some embodiments, the drive transfer mechanism's 2648 cross-section is defined by a spline with multiple teeth. The pinion's 2665 drive transfer mechanism interface includes a similarly shaped spline cross-section. The spline shapes allow for the drive transfer mechanism 2648 and the pinion 2665 to couple in multiple relative angular orientations. As shown in FIGS. 30A and 30C, the drive transfer mechanism 2648 can be mated through a middle of the pinion 2665. As shown in FIG. 30B, the drive transfer mechanism 2648 can be shaped to include a lead-in portion 2648A (e.g., a tapered or beveled end portion) to aid with proper alignment between (e.g., to urge) the drive transfer mechanism 2648 and the pinion 2665 during their coupling.

Figure 31:
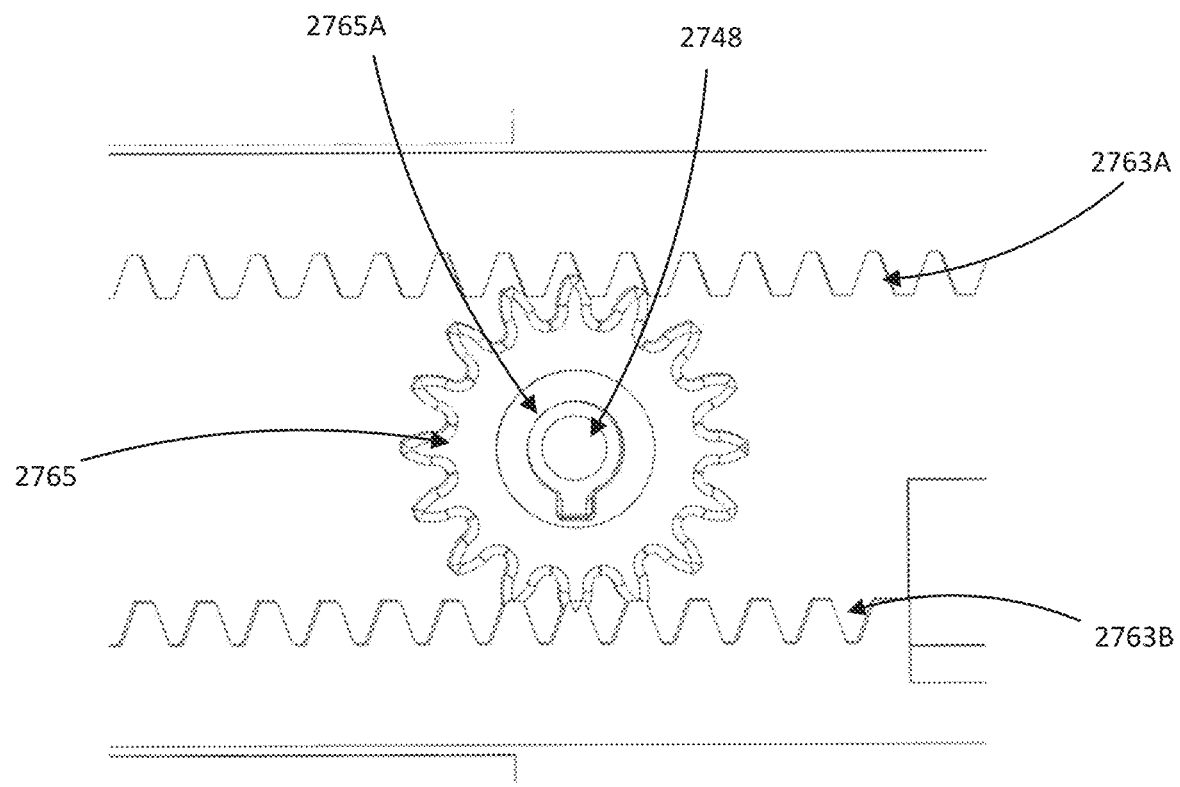
FIG. 31 is a schematic illustration of a top view of a drive transfer mechanism engaged with a keyed pinion, according to an embodiment.

In some embodiments, rather than a pinion of a drive mechanism of a fluid delivery assembly being unkeyed such that the drive shaft of the drive assembly can mate with the pinion in a variety of relative rotational positions, the pinion can be keyed. For example, FIG. 31 is a top view of a drive transfer mechanism 2748 and a keyed pinion 2765. The drive transfer mechanism 2748 and the pinion 2765 can be the same or similar in structure and/or function to any of the drive transfer mechanisms and pinions, respectively, described herein. The drive transfer mechanism 2748 can be included in any of the drive assemblies described herein and the pinion 2765 can be included in any of the fluid delivery assemblies described herein. The drive transfer mechanism 2748 and the pinion 2765 are only able to mate in a single relative angular orientation rather than in multiple relative angular orientations as in the non-keyed interface shown in FIG. 30C. As shown in FIG. 31, the drive transfer mechanism 2748 can have a keyed portion (also referred to as a key) projecting away from a central axis of the drive transfer mechanism 2748 beyond adjacent sidewall portions of the drive transfer mechanism 2748, and the pinion 2765 can define an opening 2765A with a single keyway to accept the key of the drive transfer mechanism 2748. The drive transfer mechanism 2748 and the pinion 2765 only mate in the single angular orientation where the key of the drive transfer mechanism 2748 aligns with the keyway in the pinion 2765.

In some embodiments, the keyed drive transfer mechanism 2748 can include or be coupled to a spring-loaded component, which allows a portion of the drive transfer mechanism 2748 to be recessed until the keyed portions of the drive transfer mechanism 2748 and the pinion 2765 are aligned. For example, in some embodiments, the keyed portion of the drive transfer mechanism 2748 can be transitioned to a recessed position such that the key portion does not project beyond the adjacent sidewall portions of the drive transfer mechanism 2748. The spring can be configured to urge the keyed portion toward a projecting configuration. Thus, the disposable tubing assembly including the pinion 2765 is coupled to the drive assembly including the drive transfer mechanism 2748 with the pinion 2765 and the drive transfer mechanism 2748 out of the keyed alignment, the keyed portion of the drive transfer mechanism 2748 can be urged into the recessed position by the inner wall of the pinion 2765. The drive transfer mechanism 2748 can freely rotate relative to the pinion 2765 while the spring is depressed, until the keyways are rotated into alignment (i.e., the key portion of the drive transfer mechanism 2748 is rotated into alignment with the keyway in the pinion 2765). Upon alignment, the spring force can advance the key portion of the drive transfer mechanism 2748 such that it is engaged with the keyway of the pinion 2765 and they rotate together. In some embodiments, the drive transfer mechanism 2748 is configured to be urged to a fully extended positioned relative to an upper surface of the drive assembly 2740 by a spring, and if the drive transfer mechanism 2748 is pressed against the pinion 2765 out of alignment with the keyway, the drive transfer mechanism 2748 can urge the spring away from its neutral configuration. The drive transfer mechanism 2748 can rotate freely relative to the pinion 2765 until the key portion of the drive transfer mechanism 2748 aligns with the keyway of the pinion 2765, at which point the spring can urge the drive transfer mechanism 2748 axially into keyed engagement with the pinion 2765 such that they rotate together.

Figure 32A:
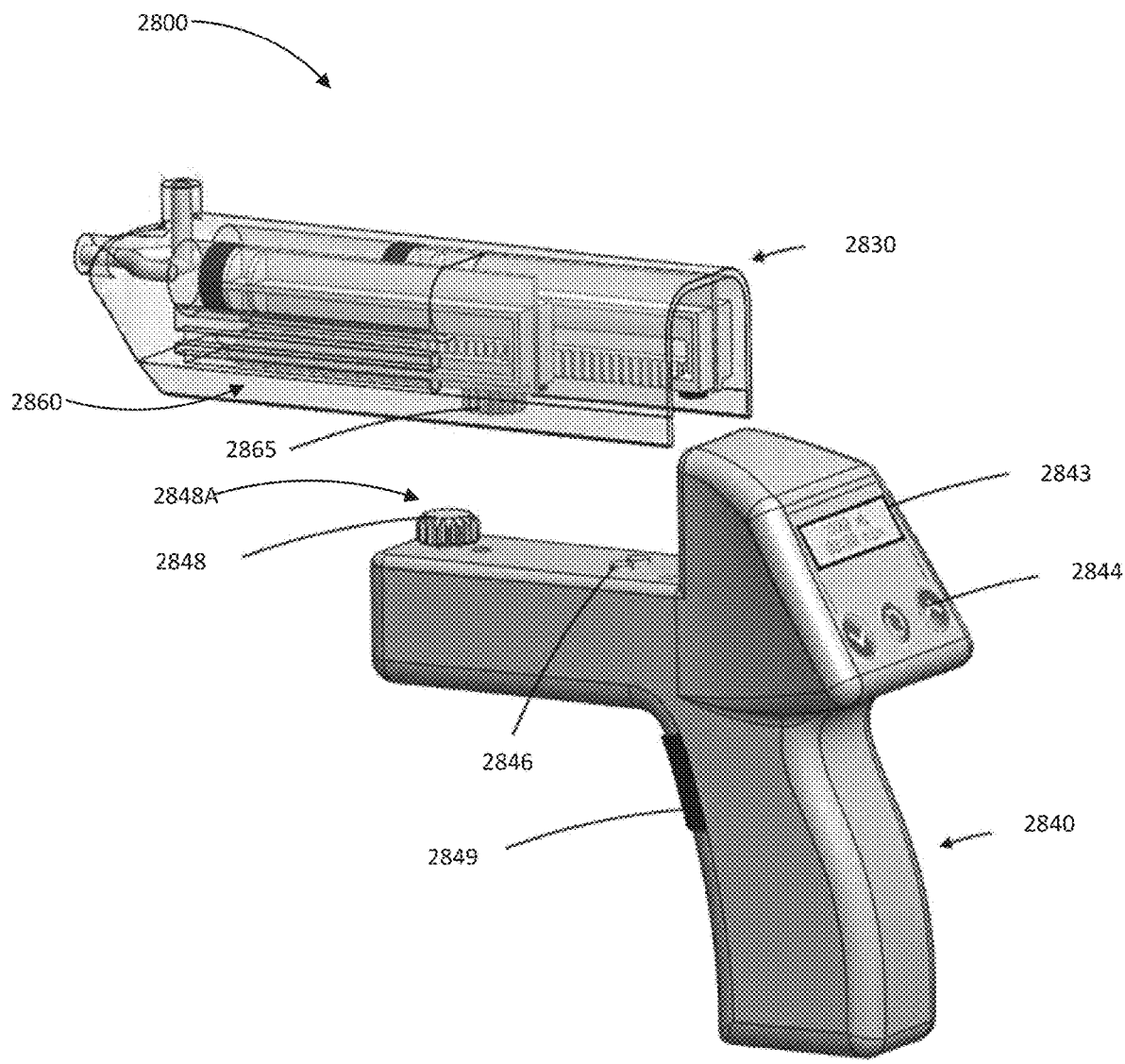
FIGS. 32A-32C are various views of a system, according to an embodiment.
Figure 32B:
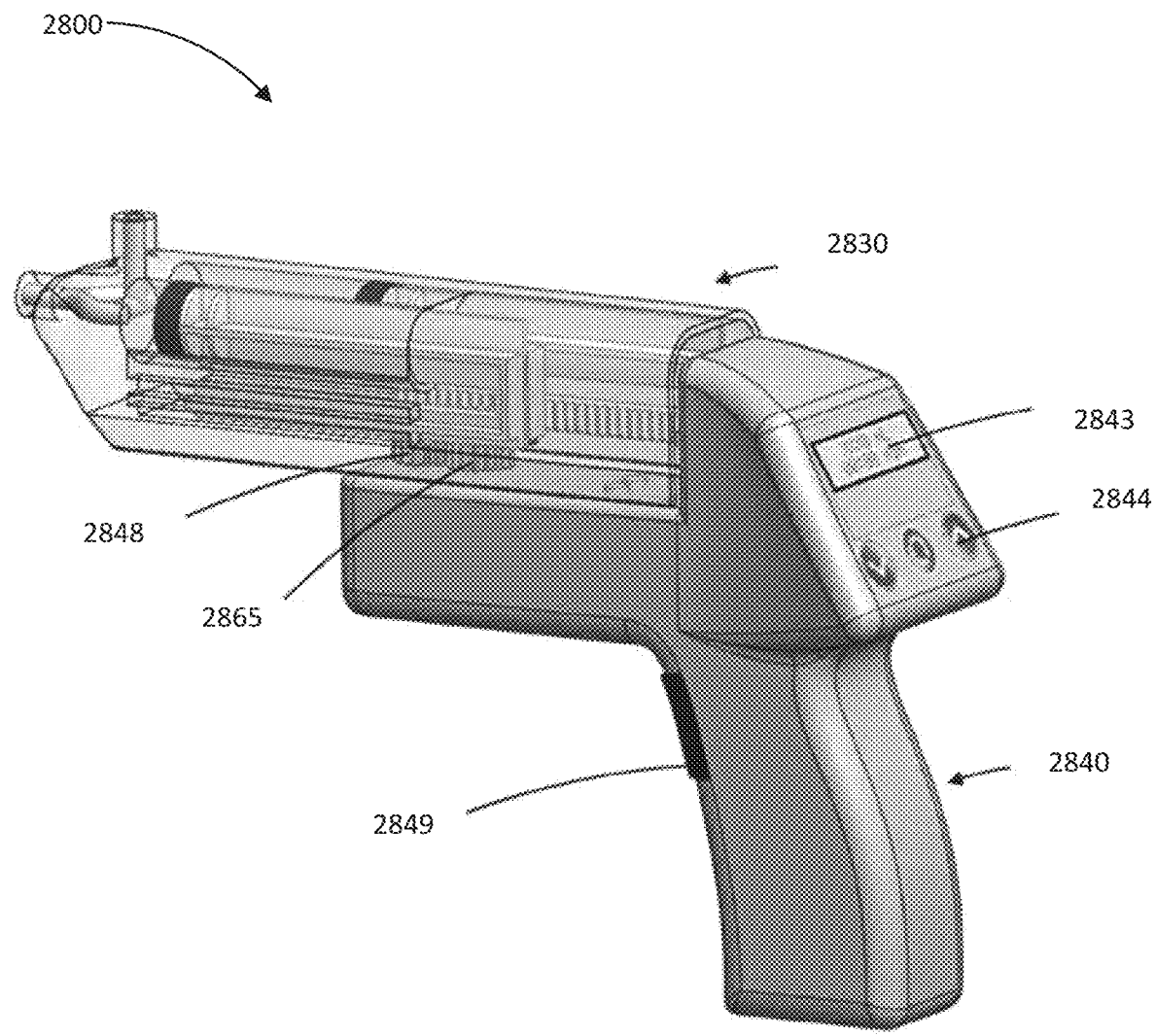
Figure 32C:
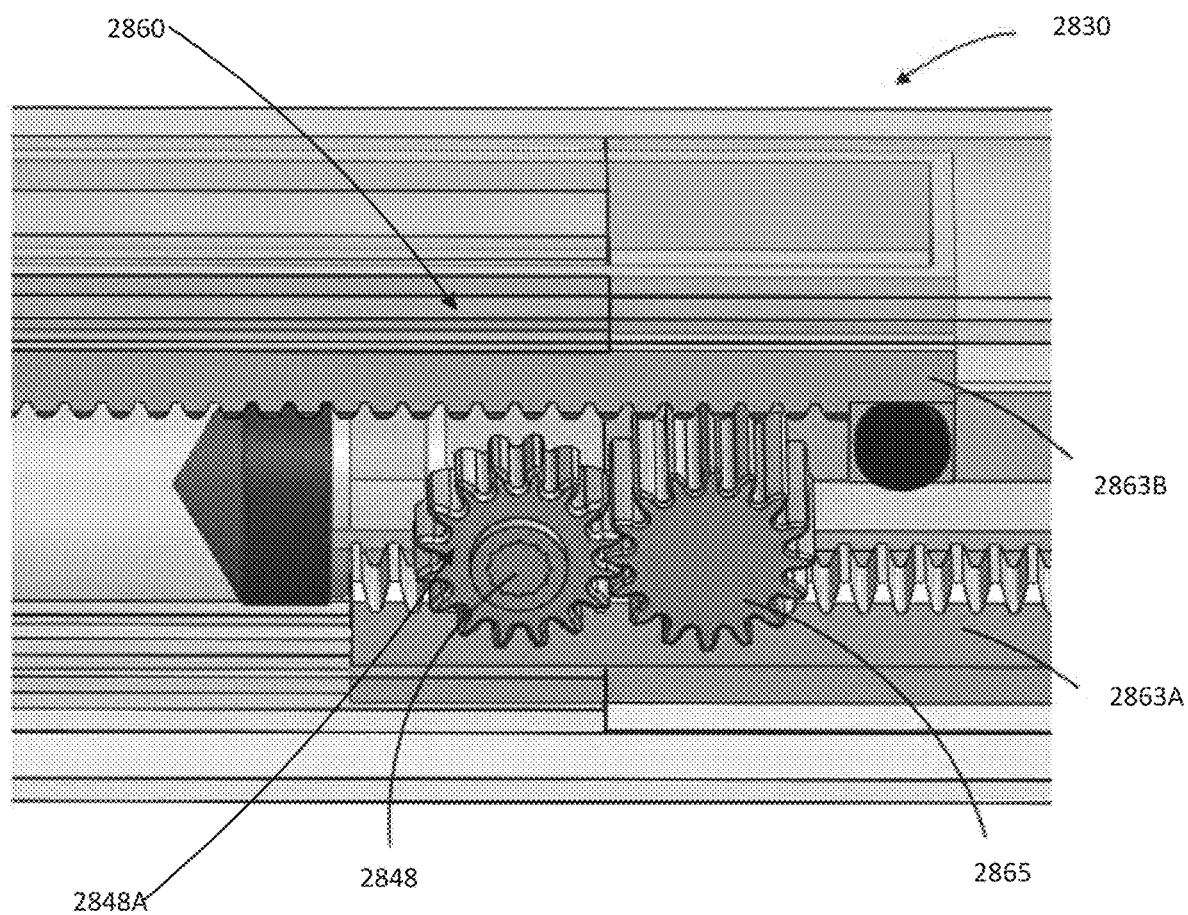

In some embodiments, the mechanical coupling between the drive assembly and the fluid delivery assembly can include a double pinion mechanism. For example, FIGS. 32A, 32B, and 32C are various views of a system 2800 including a drive assembly 2840 including a drive transfer mechanism 2848 including a gear 2848A (e.g., mounted to a drive shaft of the drive transfer mechanism 2848) and a fluid delivery assembly 2830 including a pinion 2865. The gear 2848A and the pinion 2865 are couplable to form a double pinion mechanism such that the drive assembly 2840 can control a drive mechanism 2860 of the fluid delivery assembly 2830 including the pinion 2865. The system 2800 can be the same or similar in structure and/or function to any of the other systems described herein. For example, the drive assembly 2840 can include a display 2843, a control mechanism 2849, user interface buttons 2844, and electrical contacts 2846.

FIG. 32A is a perspective view of the system 2800 showing the drive assembly 2840 and the fluid delivery assembly 2830 in an uncoupled configuration (e.g., prior to use). FIG. 32B is a perspective view of the drive assembly 2840 and the fluid delivery assembly 2830 in a coupled configuration such that the drive assembly 2840 can be operated to initiate and control fluid delivery by the fluid delivery assembly 2130. FIG. 32C is a perspective view of a cross-section of a portion of the system 2800 taken through the gear 2848A and the pinion 2865 and showing the double pinion mechanism formed when the drive transfer mechanism 2848 and the pinion 2865 are coupled together. As shown, in some embodiments, the pinion 2865 can mate non-concentrically with the drive transfer mechanism 2848 on the drive assembly 2840. As shown in FIG. 32A, the gear 2848A can be formed as a spur gear. When the fluid delivery assembly 2830 is coupled to the drive assembly 2840, as shown in FIGS. 32B and 32C, the teeth on the drive transfer mechanism 2848 (e.g., the teeth of the gear 2848A) mesh with the teeth of the pinion 2865. A lead-in on the top of the drive transfer mechanism 2848 (e.g., on the top of the gear 2848A including top portions of the teeth of the gear 2848) can be included to aid in proper mating between the drive transfer mechanism 2848 and the pinion 2865. As shown in FIG. 32C, the teeth on the drive transfer mechanism 2848 engage with the teeth on the pinion 2865 when the fluid delivery assembly 2130 is coupled to the drive assembly 2840 such that rotation of the gear 2848A causes rotation of the pinion 2865 in an opposite direction. As shown, the pinion 2865 is engaged with a first rack gear 2863A and a second rack gear 2863B of the drive mechanism 2860 such that rotation of the gear 2848A causes translation of the first rack gear 2863A and the second rack gear 2863B via rotation of the pinion 2865.

Figure 33A:
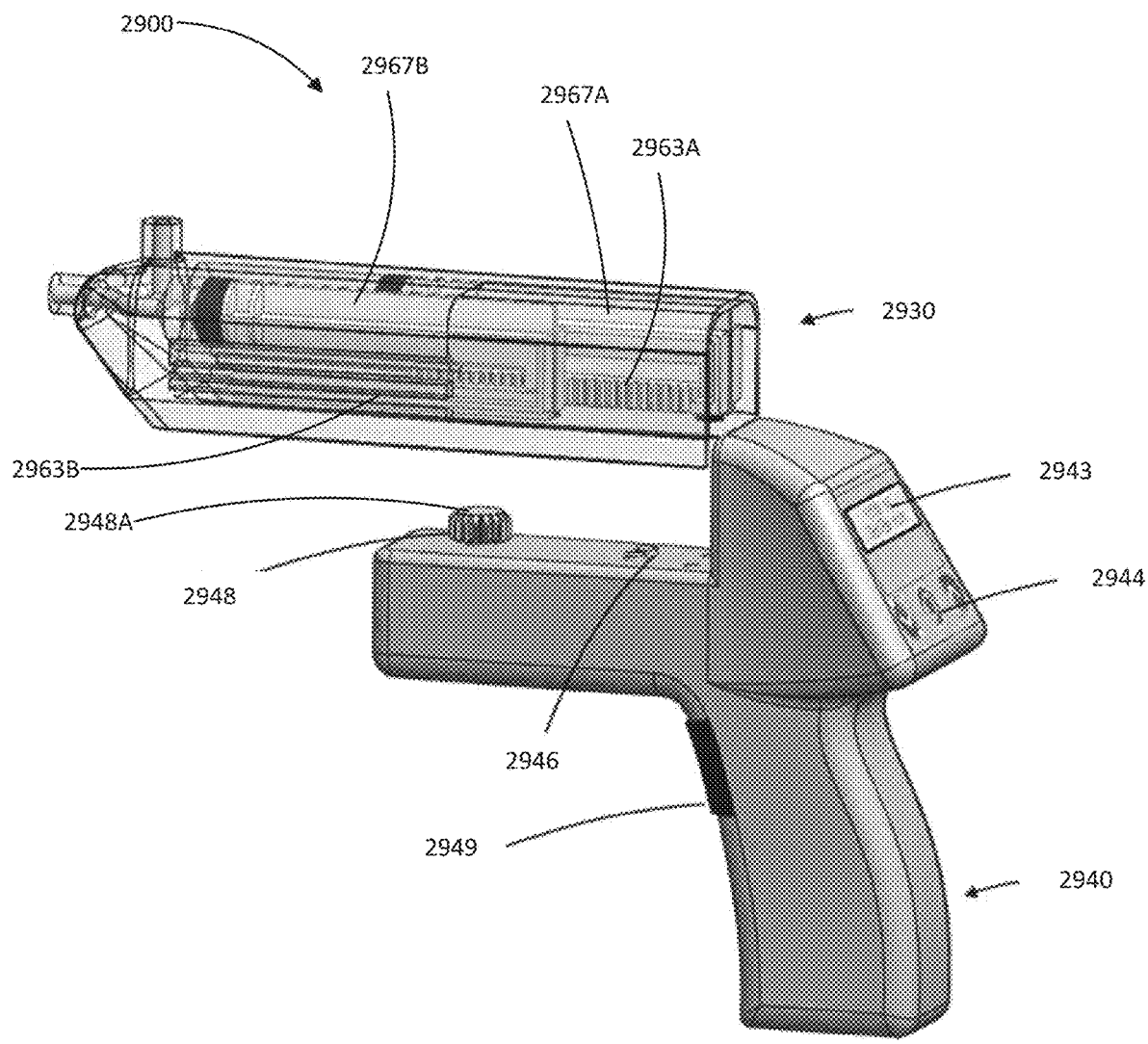
FIGS. 33A-33C are various views of a system, according to an embodiment.

In some embodiments, a drive transfer mechanism of a drive assembly can be formed as a pinion and can be configured to engage directly with rack gears of a drive mechanism of a fluid delivery assembly. For example, FIG. 33A is a perspective view of a system 2900 including a drive assembly 2940 and a fluid delivery assembly 2930 in an uncoupled configuration. The system 2900 can be the same or similar in structure and/or function to any of the systems described herein. For example, the drive assembly 2940 can include a drive transfer mechanism 2948, a display 2943, a control mechanism 2949, user interface buttons 2944, and electrical contacts 2946. The fluid delivery assembly 2930 can include a drive mechanism 2960 including a first rack gear 2963A and a second rack gear 2963B coupled to a fluid pump including a first plunger 2967A and a second plunger 2967B, respectively, via any suitable coupling such that translation of the first rack gear 2963A causes translation of the first plunger 2967A and translation of the second rack gear 2963B causes translation of the second plunger 2967B.

Figure 33B:
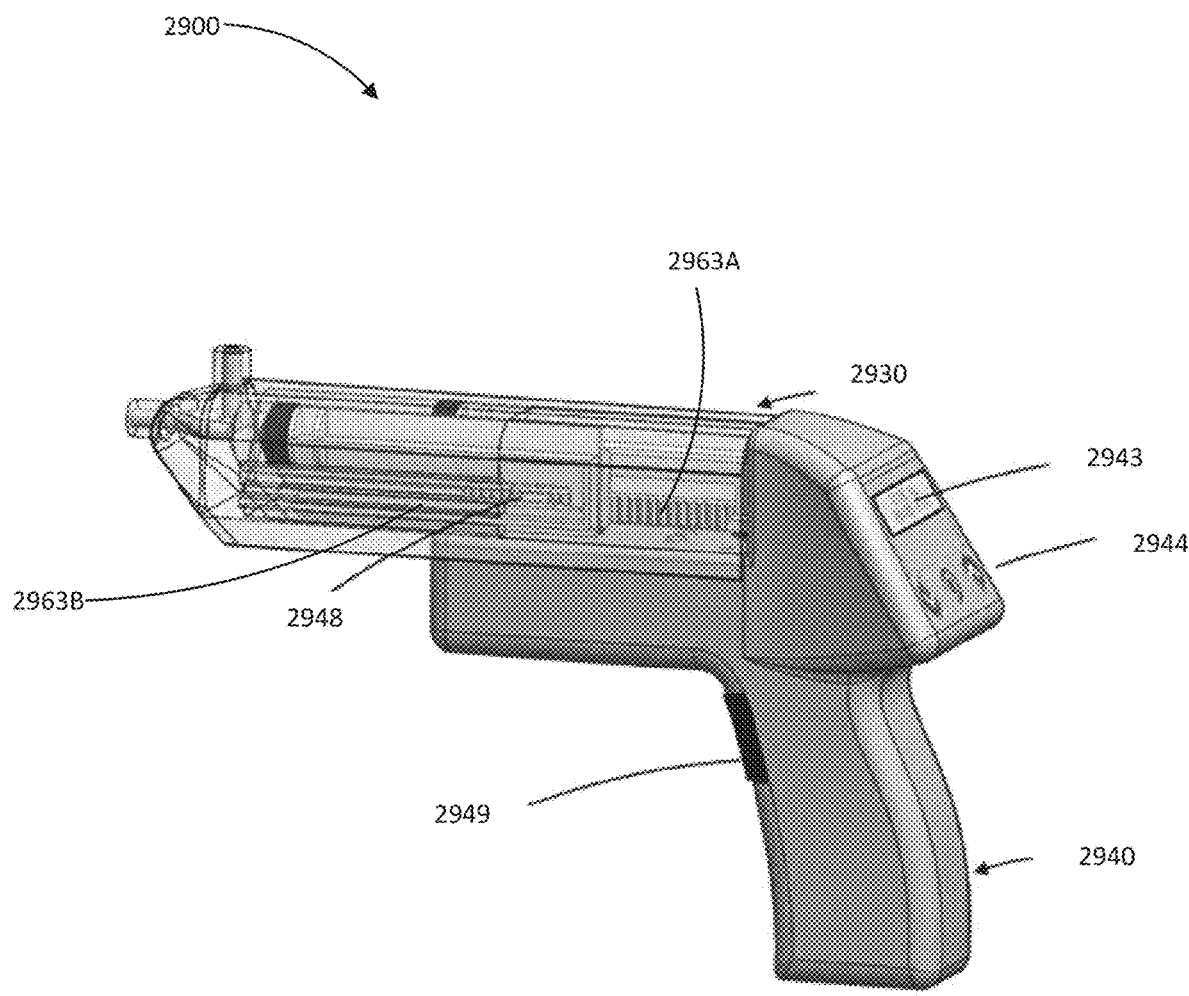
Figure 33C:
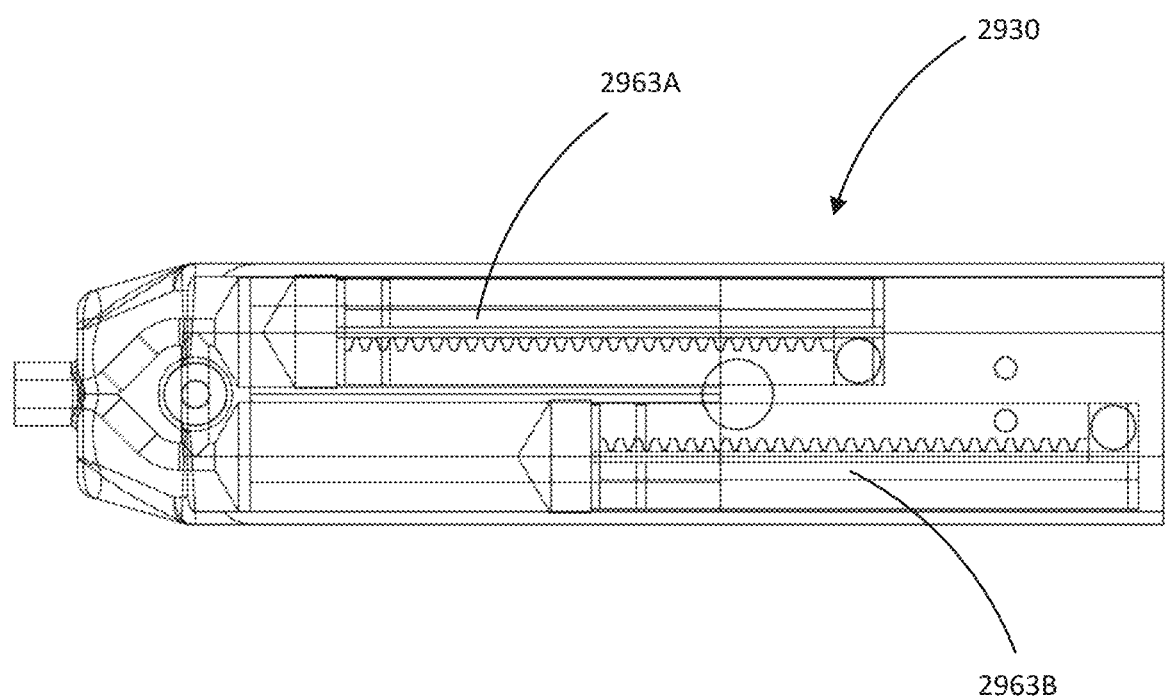

When the fluid delivery assembly 2930 is coupled to the drive assembly 2940 (e.g., via vertical displacement of the fluid delivery assembly 2930 relative to an upper surface of the drive assembly 2940), as shown in FIG. 33B, teeth on a pinion 2948A of the drive transfer mechanism 2948 can mesh with the teeth on the first rack gear 2963A and the second rack gear 2963B. For example, a set of teeth on a first portion a perimeter of the pinion 2948A can engage with teeth on the first rack gear 2963A and teeth on a second portion of the perimeter of the pinion 2948A opposite the first portion can engage with teeth on the second rack gear 2963B. A lead-in on the top of the drive transfer mechanism 2948 (e.g., disposed above and/or including a top portion of the teeth of the drive transfer mechanism 2948) can be included to aid in proper engagement between the drive transfer mechanism 2948 and the rack gears 2963A, 2963B. FIG. 33C shows a bottom view of the rack gears 2963A, 2963B. As shown, the rack gears 2963A, 2963B can also include lead-ins to aid in engagement between the teeth on the drive transfer mechanism 2948 and on the rack gears 2963A, 2963B. The rack gears 2963A, 2963B can be disposed parallel and a distance apart sufficient for the pinion 2948A to be received between the first rack gear 2963A and the second rack gear 2963B such that rotation of the pinion 2948A in a first direction causes the first rack gear 2963A to translate in a first direction and the second rack gear 2963B to translate in a second direction opposite the first direction, and such that rotation of the pinion 2948A in a second direction causes the first rack gear 2963A to translate in the second direction and the second rack gear 2963B to translate in the first direction.

In some embodiments, a drive assembly can include two pinions configured to be engaged with respective rack gears of a fluid delivery assembly. For example, FIGS. 34A-34D are various views of a system 3000 having a drive assembly 3040 and a fluid delivery assembly 3030. The system 3000 can be the same or similar in structure and/or function to any of the systems described herein. For example, the drive assembly 3040 includes a drive transfer mechanism 3048 including a first pinion 3048A and a second pinion 3048B, a display 3043, and a control mechanism 3049. The fluid delivery assembly 3030 can include a fluid pump including a first reservoir 3064, a second reservoir 3066, a first piston 3062A, and a second piston 3062B, and a drive mechanism 3060 including a first rack gear 3063A and a second rack gear 3063B, which can be coupled to or form a first plunger 3067A and a second plunger 3067B, respectively, such that translation of the first rack gear 3063A causes translation of the first piston 3062A relative to the first reservoir 3064 and translation of the second rack gear 3063B causes translation of the second piston 3062B relative to the second reservoir 3066. In some embodiments, the first plunger 3067A and the second plunger 3067B can be included in the fluid pump of the fluid delivery assembly 3030.

The first pinion 3048A and the second pinion 3048B of the drive transfer mechanism 3048 are configured to be engaged with the first rack gear 3063A and the second rack gear 3063B such that the first pinion 3048A and the second pinion 3048B can drive the first piston 3062A and the second piston 3062B, respectively. In some embodiments, the first pinion 3048A and the second pinion 3048B are coaxial. In some embodiments, the first pinion 3048A and the second pinion 3048B can be independently controllable (e.g., by a controller and/or motor of the drive assembly 3040). In some embodiments, the first pinion 3048A and the second pinion 3048B are configured to be rotated in opposite directions and to alternate rotational directions.

Figure 34A:
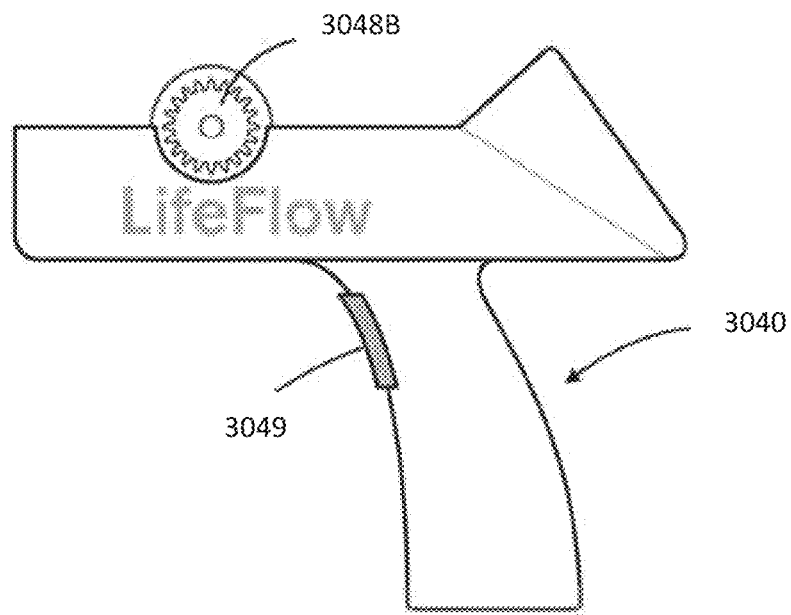
FIGS. 34A-34D are various views of a system, according to an embodiment.
Figure 34B:
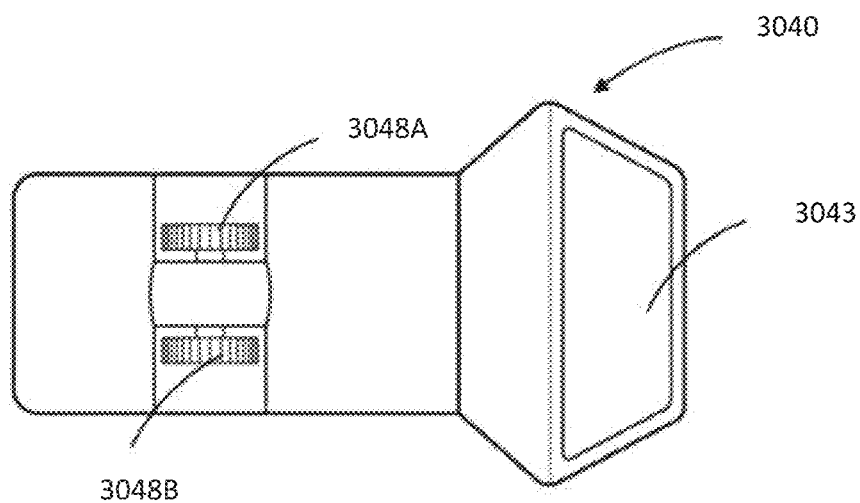
Figure 34C:
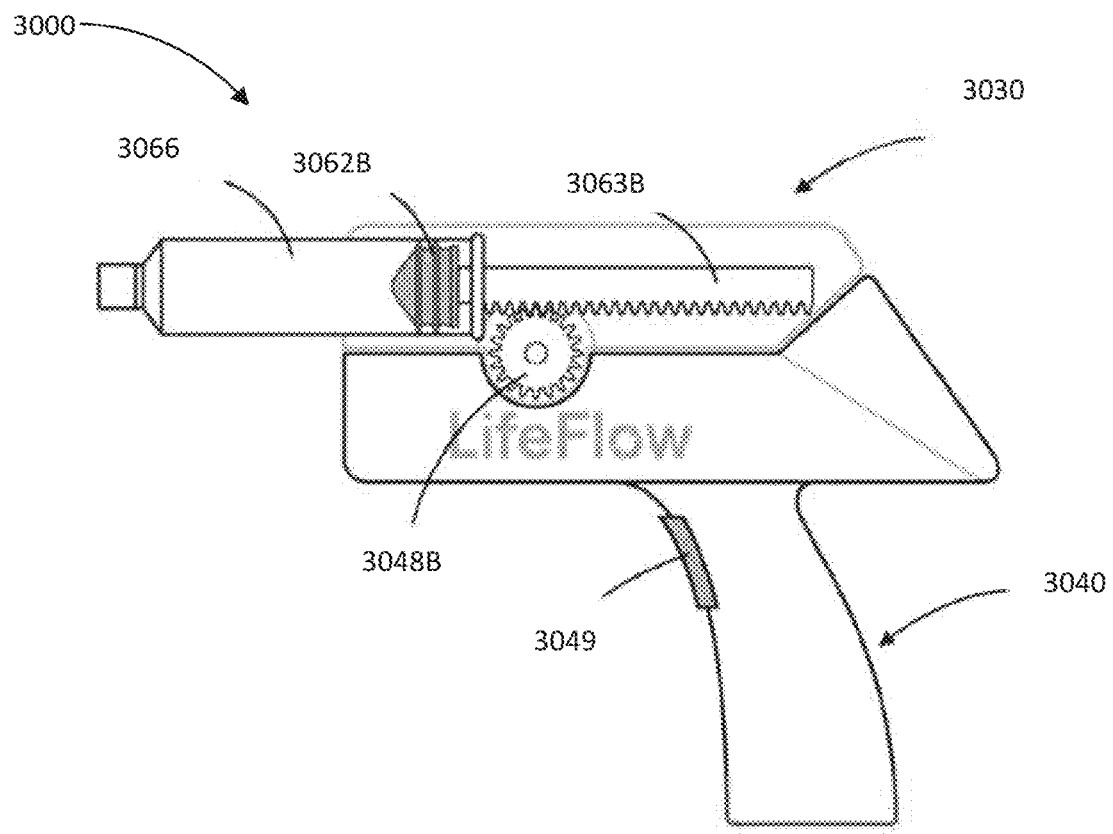
Figure 34D:
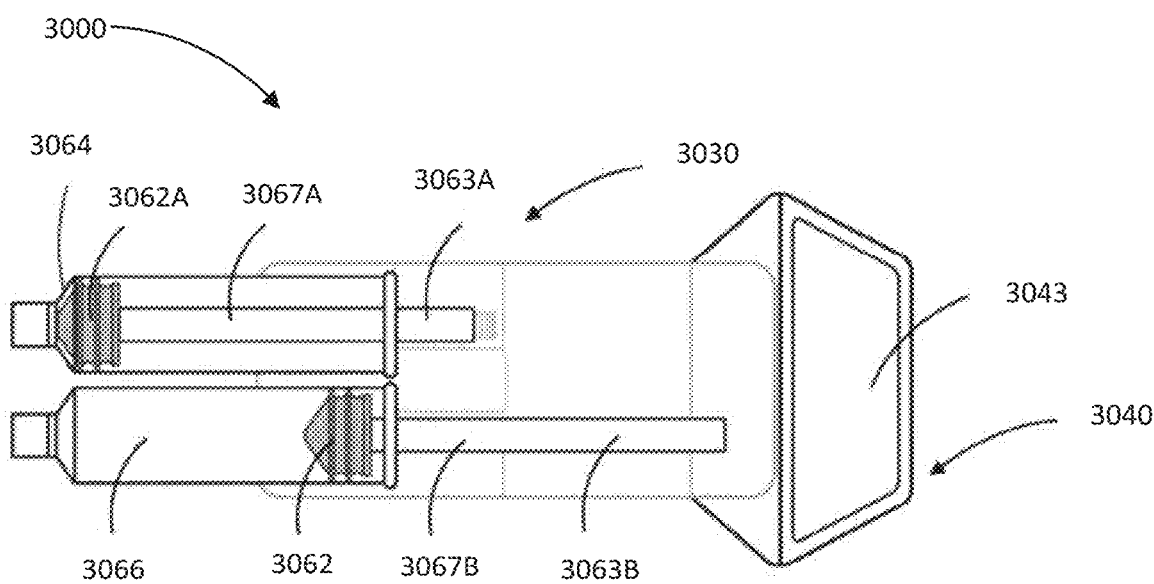

As shown in FIG. 34C, when the fluid delivery assembly 3030 is coupled to the drive assembly 3040, the teeth on the second rack gear 3063B mesh with the teeth on the second pinion 3048B of the drive assembly 3040, and the teeth on the first rack gear 3063A mesh with the teeth on the first pinion 3048A. The first pinion 3048A and the second pinion 3048B can then be rotated in opposite directions, causing the first rack gear 3063A and the second rack gear 3063B, and thus the first piston 3063A and the second piston 3063B, to translate in opposite directions.

The drive transfer mechanism 3048 can include one or more shafts coupled to each of the first pinion 3048A and the second pinion 3048B and configured to drive the first pinion 3048A and the second pinion 3048B. Although not shown in FIGS. 34A-34D, in some embodiments, strain gauges, a torsion load cell, or other force sensing mechanisms may be disposed on the shafts driving the first and second pinions 3048A,B. The force sensing mechanisms can allow a controller of the drive assembly 3040 to identify increases in resistance to rotation of the first or second pinion 3048A,B and to determine if the increased resistance to movement was a result of increased force in outlet tubing coupled to a fluid outlet of the fluid delivery assembly 3030, or the result of increased force or resistance within inlet tubing coupled to a fluid inlet of the fluid delivery assembly 3030. If a force sensing mechanism associated with (e.g., coupled to) the first pinion 3048, for example, registered a high force when the first reservoir 3064 was increasing in size (e.g., when the first pinion 3048A is rotating in a first direction), this would indicate that that there was high resistance in the inlet tubing. This increased force may be, for example, a result of an empty fluid bag (e.g., an empty blood bag), and the first piston 3062A trying to pull a vacuum from the empty fluid bag into the first reservoir 3064, a result of a clamp that is closed on the inlet tubing preventing fluid flow, or other similar conditions. Upon determining high resistance (e.g., resistance over a threshold or a change in resistance over a threshold) associated with the inlet tubing line, the controller can stop the motor driving the pinion 3048A and controlling fluid flow and/or inform the user via a message on the display 3043 that the source fluid bag needs to be checked. If instead the force sensing mechanism connected to the first pinion 3048A detected a high resistance or force when the first reservoir 3064 was decreasing in size (e.g., when the first pinion 3048A is rotating in a second direction opposite the first direction), this would indicate that there was an obstruction or constriction in the outlet tubing. Obstructions or constrictions in the outlet tubing can be caused by a variety of sources including, but not limited to, an infiltrated IV, a clamp inadvertently closed on the outlet tubing, or a patient who has repositioned and partially obstructed an intravenous catheter. Upon determining high resistance (e.g., resistance over a threshold or a change in resistance over a threshold) associated with the outlet tubing line, the controller can stop the motor driving the pinion 3048A and controlling flow and/or can inform the user via a message on the display 3043 to check the outlet tubing and patient access, including the intravenous catheter.

Figure 35A:
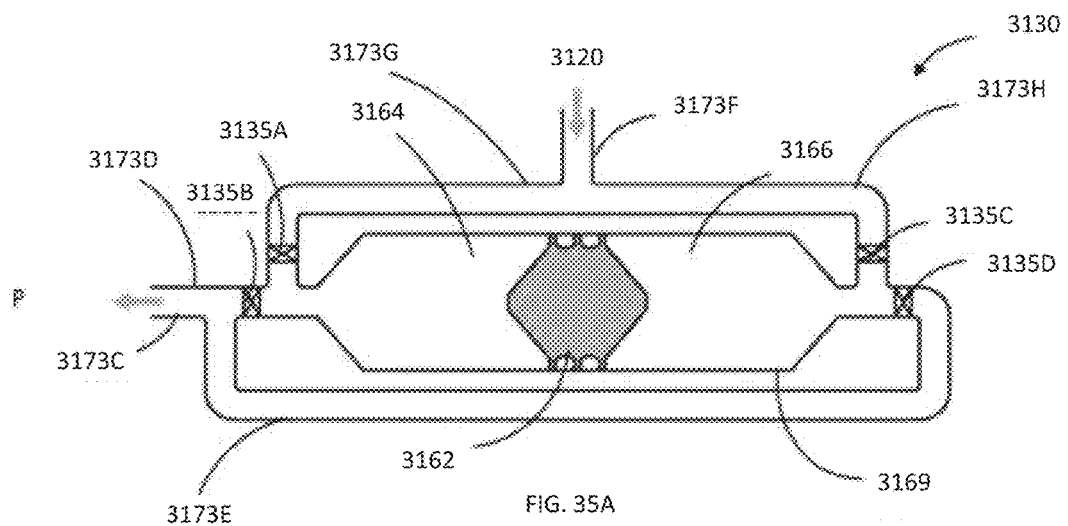
FIGS. 35A-35C are schematic illustrations of a fluid delivery assembly in various stages of operation, according to an embodiment.
Figure 35B:
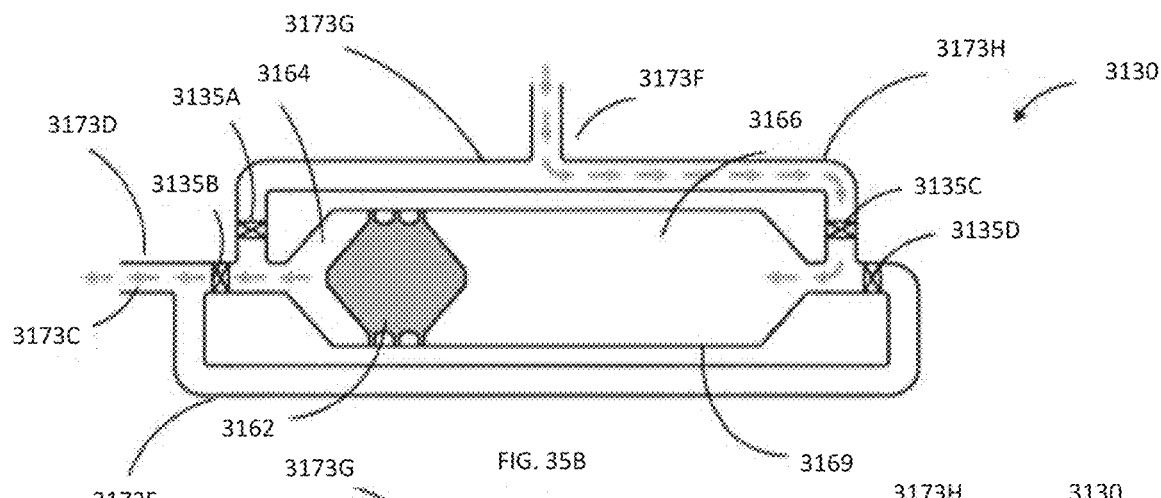
Figure 35C:
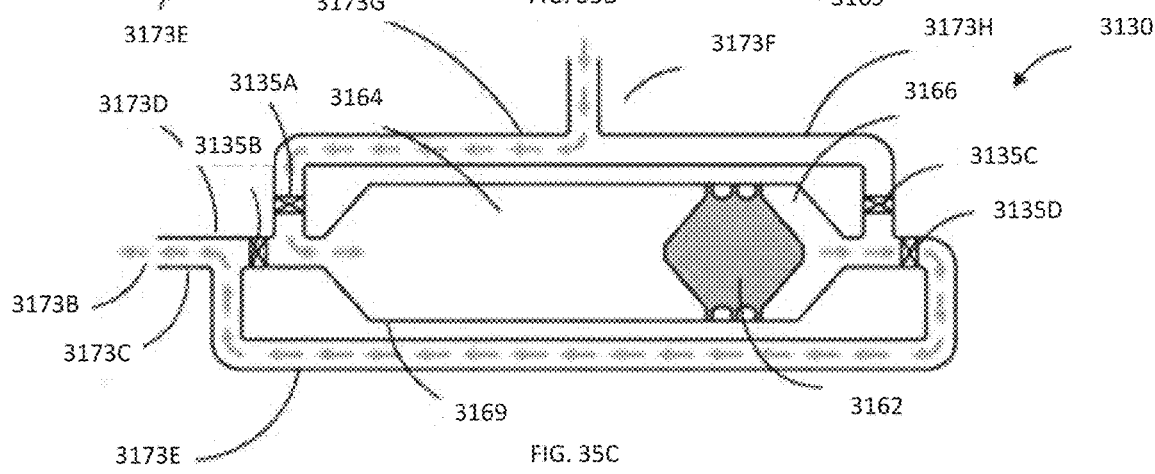

In some embodiments, only one piston may be included in a fluid delivery assembly to control fluid flow into and out of a first reservoir and a second reservoir of the fluid delivery assembly. For example, FIGS. 35A-35C are schematic illustrations of a fluid delivery assembly 3130 in various stages of operation. The fluid delivery assembly 3130 includes a first reservoir 3164 and a second reservoir 3166 defined by the same container 3169 (e.g., tube) and only one piston 3162 defining a boundary of the first reservoir 3164 and the second reservoir 3166. The fluid delivery assembly 3130 can be the same or similar in structure and/or function to any of the fluid delivery assemblies described herein. A drive mechanism (not shown) can be operable to translate the piston 3162 within the container 3169 to simultaneously draw fluid from the fluid source 3120 into the first reservoir 3164 via the fluid line 3173G and to expel fluid from the second reservoir 3166 to the patient P via the fluid line 3173E as shown in FIG. 35C, and to translate the piston 3162 in the opposite direction to simultaneously draw fluid from the fluid source 3120 into the second reservoir 3166 via the fluid line 3173H and to expel fluid from the first reservoir 3164 to the patient via the fluid line 3173D as shown in FIG. 35B. In some embodiments, rather than being only one piston 3162 disposed in the container defining the first reservoir 3164 and the second reservoir 3166, the fluid delivery assembly 3130 can include two pistons within the container coupled together (e.g., via the drive mechanism). In some embodiments, for example, the drive mechanism can include one or more magnets that can be disposed within the piston 3162 or disposed between two pistons 3162 within the container 3169 such that translation of the one or more pistons 3162 can be controlled via magnetic interaction with the one or more magnets of the drive mechanism. Thus, the fluid delivery assembly 3130 can be coupled to a drive assembly, such as any of the drive assemblies described herein, and the drive assembly can include one or more magnets configured to be translated relative to the container 3169 such that the one or more pistons 3162 are translated within the container 3169 due to magnetic interaction between the one or more magnets of the drive assembly and the one or more magnets of the drive mechanism of the fluid delivery assembly 3130 (e.g., within or coupled to the piston(s) 3162).

Figure 36:
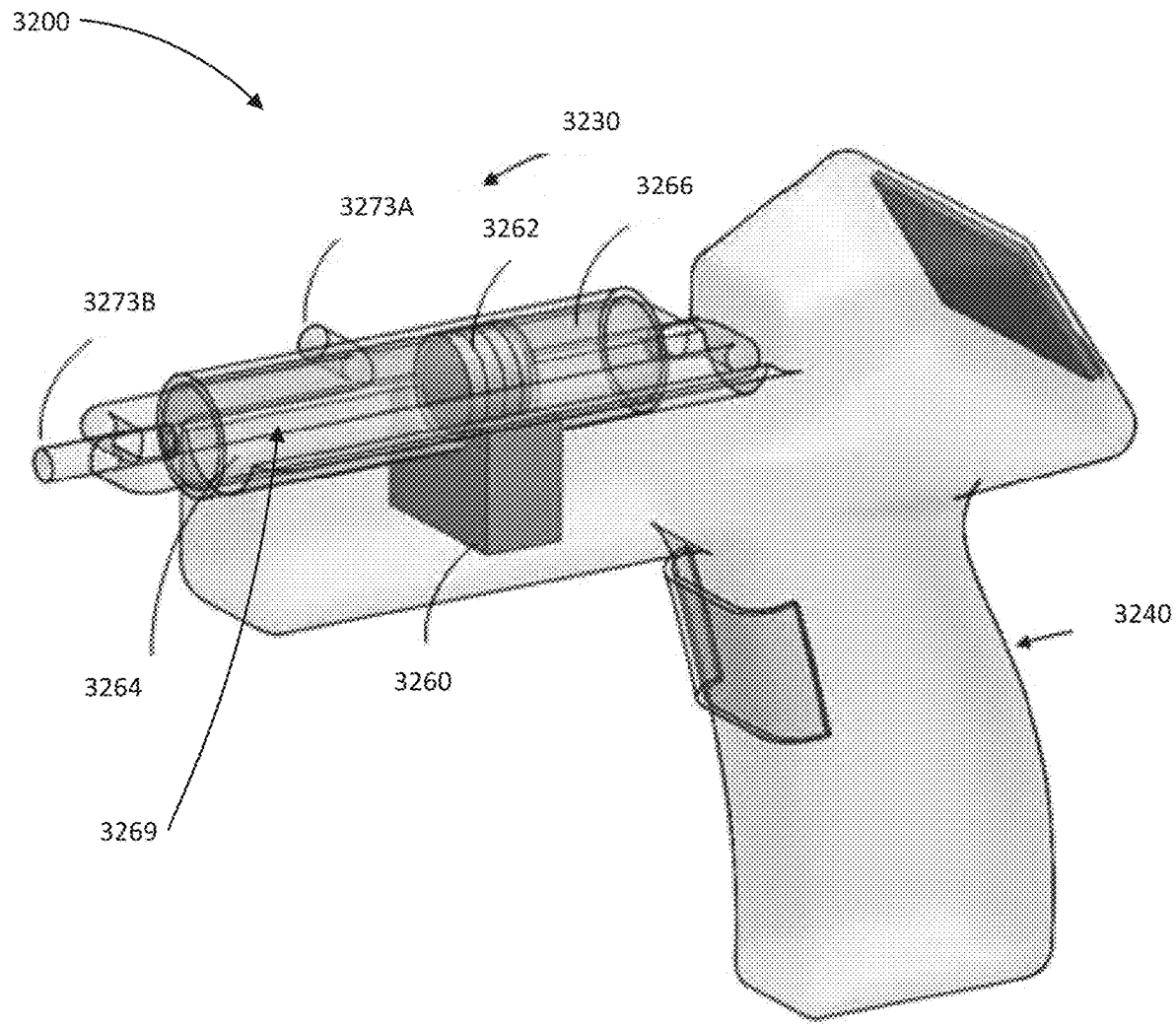
FIG. 36 is a schematic illustration of a system, according to an embodiment.

FIG. 36 is a perspective view of a system 3200. The system 3200 can be the same or similar in structure and/or function to any of the systems described herein. For example, the system 3200 includes a drive assembly 3240 and a fluid delivery assembly 3230. The fluid delivery assembly 3230 can be the same or similar in structure and/or function to the fluid delivery assembly 21230 described above with respect to FIGS. 35A-35C. For example, the fluid delivery assembly includes a fluid inlet 3273A, a fluid outlet 3273, and a fluid pump including a container 3269 defining a first reservoir 3264 and a second reservoir 3266 and a piston 3262. As shown in FIG. 36, the fluid delivery assembly 3230 can be coupled to the drive assembly 3240. The drive assembly 3240 can include a drive transfer mechanism 3260 that is configured to magnetically interact with a magnet coupled to (e.g., disposed within) the piston 3262. For example, the drive transfer mechanism 3260 can include one or more magnets configured to be translated (e.g., along a track or bar) parallel to the central axis of the container 3269 such that the piston 3262 is translated along the central axis of the container 3269 due to magnetic interaction between the drive transfer mechanism 3260 and the magnet(s) associated with the piston 3262, causing fluid to be drawn into and expelled from the container 3269 on alternating sides of the piston 3262.

Figure 37:
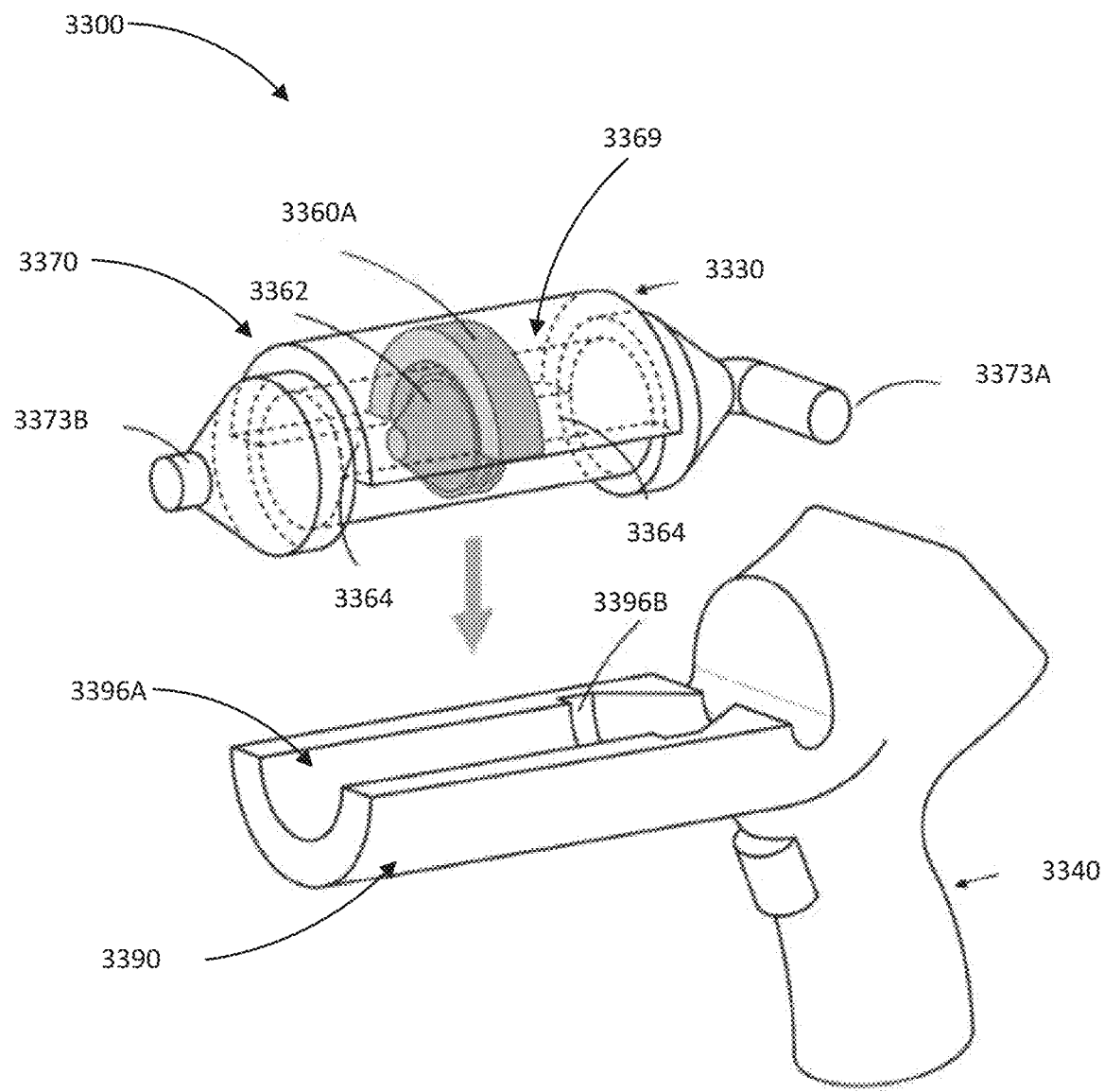
FIG. 37 is a schematic illustration of a system, according to an embodiment.

FIG. 37 is a schematic illustration of a perspective view of a system 3300 prior to a fluid delivery assembly 3330 of the system 3300 being coupled to a drive assembly 3340 of the system 3300. The system 3300 can be the same or similar in structure and/or function to any of the systems described herein. For example, the fluid delivery assembly 3330 includes a housing 3370, a fluid inlet 3373A, and a fluid outlet 3373B, and a fluid pump including a piston 3362 and a container 3369 (e.g., a tubular container) containing the piston 3362 and defining a first reservoir 3364 on a first side of the piston 3362 and a second reservoir 3366 on a second side of the piston 3362. The piston 3362 includes a magnet (not shown) disposed within or coupled to the piston 3362. The fluid delivery assembly 3330 includes a drive mechanism 3360A which includes or is formed as a magnet configured to magnetically interact with the magnet of the piston 3362 to control the translational position of the piston 3362. The drive mechanism 3360A can be disposed in a space defined between a surface of the housing 3370 and an outer surface of the container 3369 such that the drive mechanism 3360A can translate along the outer surface of the container 3369 within the space.

As shown in FIG. 37, the drive assembly 3340 includes a housing 3390 defines a recess configured to receive a portion of the fluid delivery assembly 3330. For example, the housing 3390 can define a first recessed portion 3396A configured to receive an exposed bottom portion of the container 3369. The housing 3390 can also define a second recessed portion 3396B configured (e.g., shaped and sized) to receive a larger diameter portion of the housing 3370 such that the fluid delivery assembly 3330 can be securely retained by the drive assembly 3340. As shown in FIG. 37, the larger diameter distal portion of the housing 3370 can also be configured to seat against a distal surface of the housing 3390, and the housing 3390 can optionally define a space to receive the fluid inlet 3373A. The drive assembly 3340 also includes a magnet configured to interact with at least one of the magnet of the piston 3362 and the magnet(s) of the drive mechanism 3360A such that translation of the magnet of the drive assembly 3340 causes corresponding translation of the piston 3362. For example, the drive assembly 3340 can include a semi-circular magnet similar in shape to the semi-circular magnet of the drive mechanism 3360A such that the piston 3362 (and associated magnet) can be partially received within a recess of the magnet of the drive assembly 3340 and partially received within a recess of the drive mechanism 3360A and is thus surrounded by the magnets. Thus, translation of the magnet of the drive assembly 3340 (e.g., under control of a motor of the drive assembly 3340 along a track or bar) causes translation of the piston 3362, causing fluid to be drawn into and expelled from the container 3369 on alternating sides of the piston 3362.

Figure 38A:
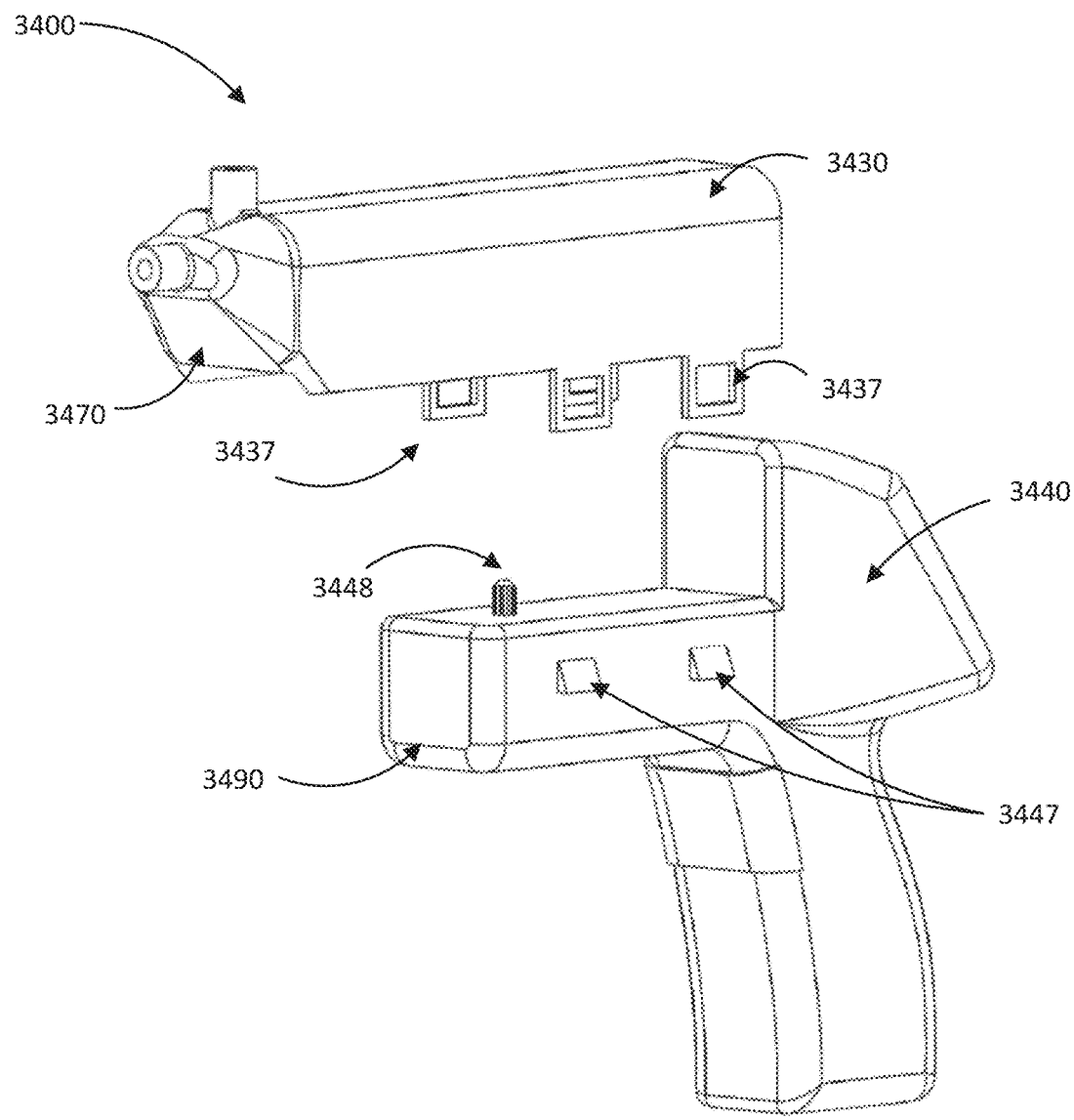
FIGS. 38A and 38B are schematic illustrations of a system in a first configuration and a second configuration, respectively, according to an embodiment.
Figure 38B:
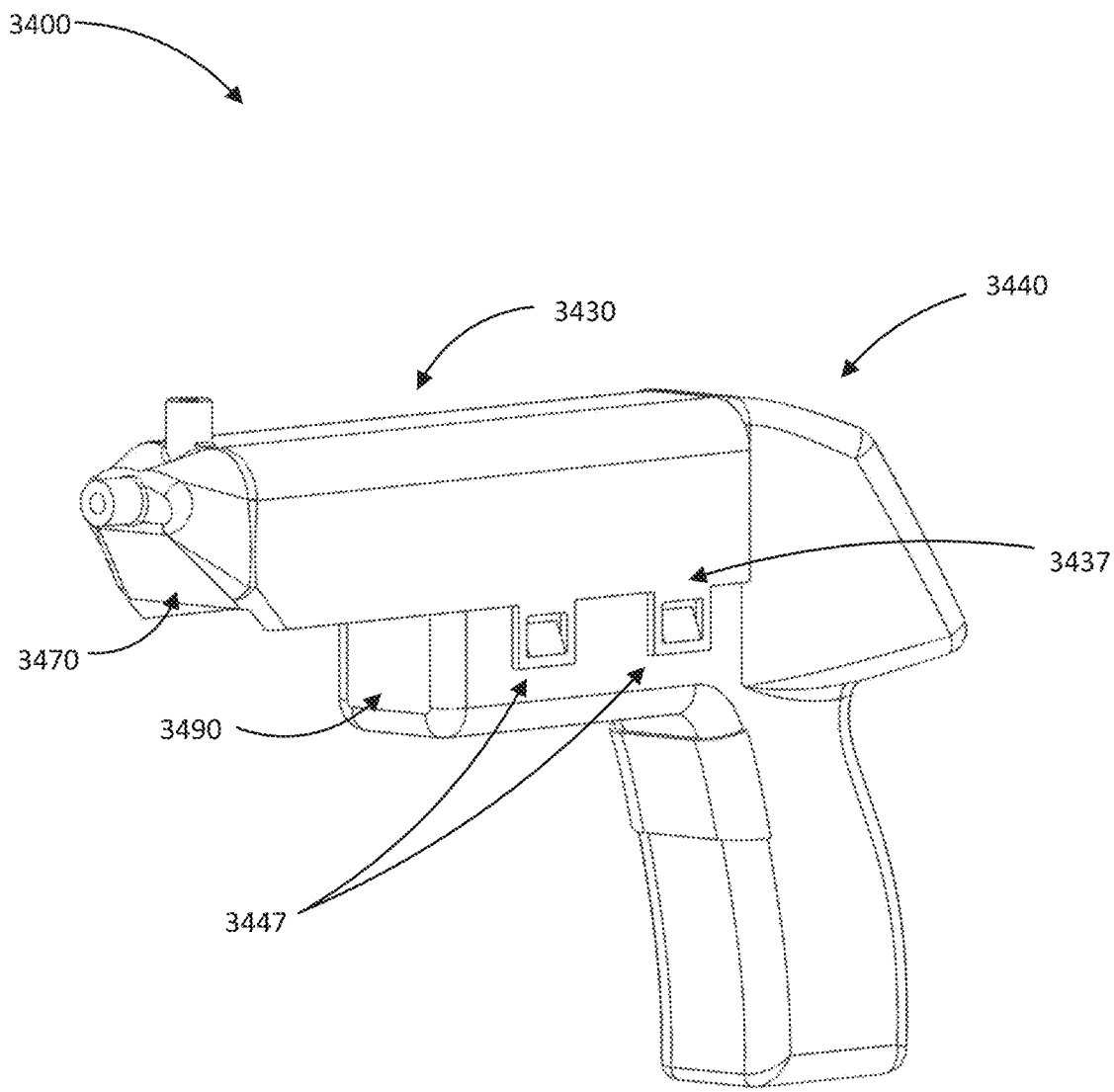

As described above, in some embodiments, a fluid delivery assembly and a drive assembly can include mating retention features such that the fluid delivery assembly can be releasably secured to the drive assembly during use. For example, FIGS. 38A and 38B are perspective views of a system 3400 in an uncoupled and a coupled configuration, respectively. The system 3400 can be the same or similar in structure and/or function to any of the systems described herein. For example, the fluid delivery assembly includes a housing 3470 and the drive assembly 3440 includes a housing 3490 and a drive transfer mechanism 3448. As shown in FIG. 38A, the fluid delivery assembly 3430 includes retention features 3437 projecting from the housing 3470. The drive assembly housing 3490 includes retention features 3447 that are configured (e.g., shaped and sized) to mate with the retention features 3437 on the fluid delivery assembly 3430 and hold the two assemblies together during use. The retention features 3447 can include, for example, projections configured to be received within slots defined by the retention features 3437. The retention features 3447 can, for example, be tapered. FIG. 38B shows the two assemblies coupled together as they would be during use. After use, the fluid delivery assembly 3430 may be separated from the drive assembly 3440 by squeezing the fluid delivery assembly's housing 3470 and/or pulling on the retention features 3437, allowing for the fluid delivery assembly retention features 3437 to be deformed and disengaged from the drive assembly retention features 3440. Proper alignment between the two assemblies (e.g., proper alignment of mechanical drive connections and/or electrical contacts) may be achieved by coupling the retention features 3437 to the retention features 3447. Thus, the fluid delivery assembly 3430 can be clicked into proper alignment relative to the drive assembly 3440 (e.g., one handed).

Figure 39A:
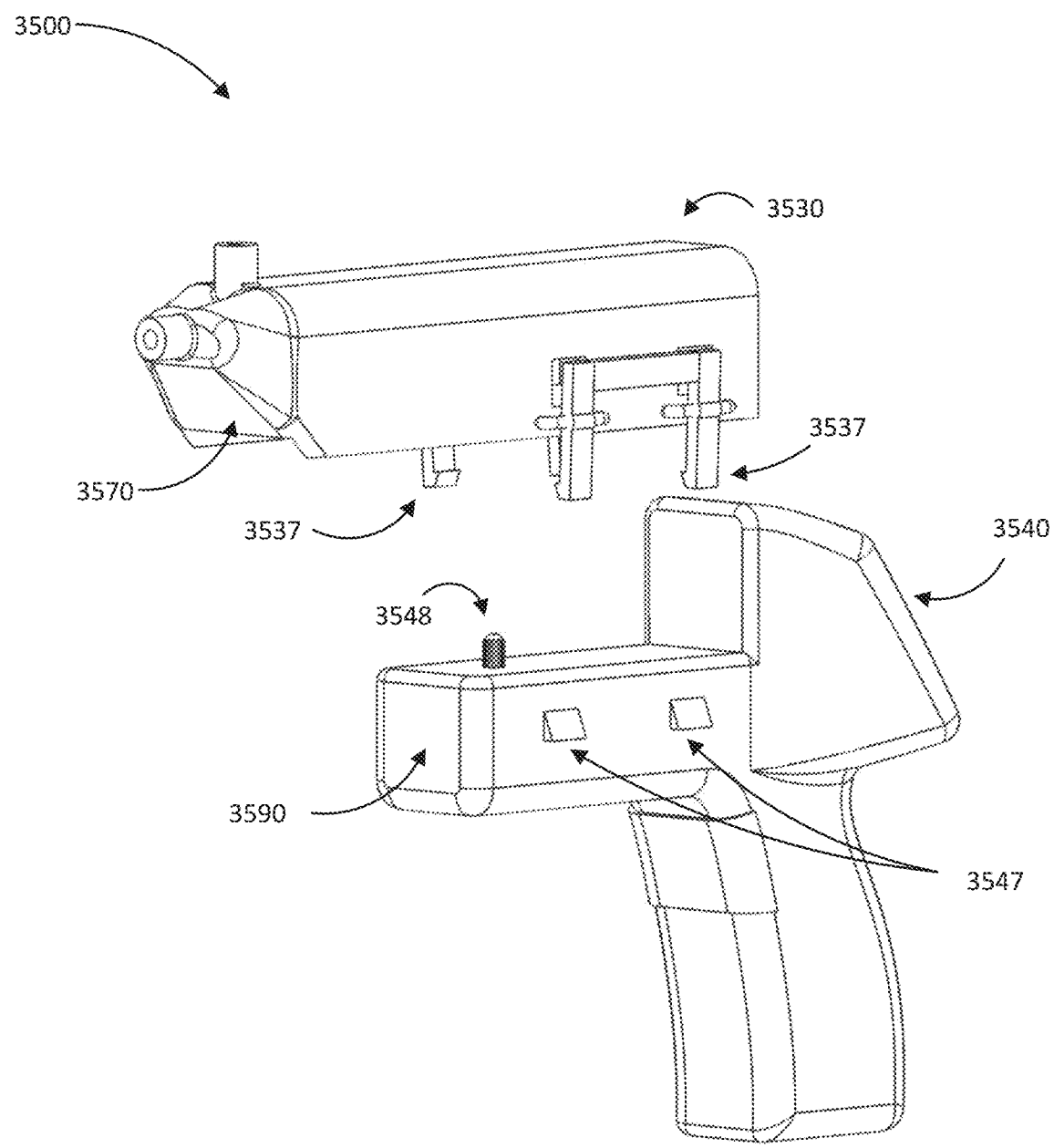
FIGS. 39A and 39B are schematic illustrations of a system in a first configuration and a second configuration, respectively, according to an embodiment.
Figure 39B:
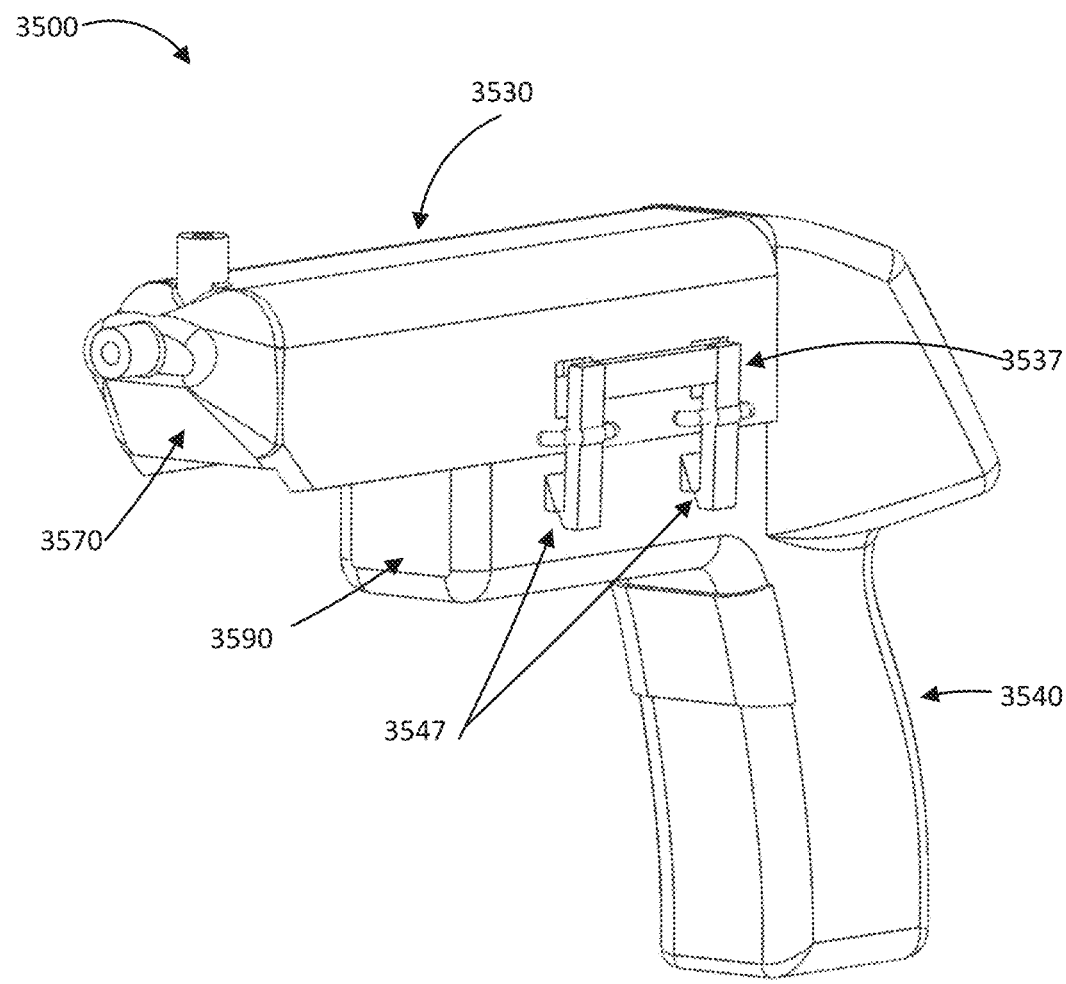

FIGS. 39A and 39B are perspective views of a system 3500 in an uncoupled and a coupled configuration, respectively. The system 3500 can be the same or similar in structure and/or function to any of the systems described herein. For example, the fluid delivery assembly includes a housing 3570 and the drive assembly 3540 includes a housing 3590 and a drive transfer mechanism 3548. As shown in FIG. 39A, the fluid delivery assembly 3530 includes separate retention mechanisms or latches 3537. The drive assembly housing 3590 includes retention features 3547 that are configured (e.g., shaped and sized) to mate with the retention features 3537 on the fluid delivery assembly 3530 and hold the two assemblies together during use. For example, the retention features 3547 can include, for example, projections configured to be engaged with flanges projecting from arms included in the retention features 3537. The retention features 3547 can, for example, be tapered. FIG. 39B shows the two assemblies mated together as they would be during use. After use, the fluid delivery assembly 3530 may be removed from the drive assembly 3540 by squeezing the retention features 3537 above the pivot point of the retention features 3537, allowing for the fluid delivery assembly retention features 3537 to rotate out of engagement from the drive assembly retention features 3540. Proper alignment between the two assemblies (e.g., proper alignment of mechanical drive connections and/or electrical contacts) may be achieved by coupling the retention features 3537 to the retention features 3547. In some embodiments, the fluid delivery assembly 3530 and/or the drive assembly 3540 can include separate or additional alignment features, such as any of the alignment features described herein (e.g., longitudinal flanges extending from a bottom surface of the housing 3570 and configured to engage with opposite sides of the housing 3590). Thus, the fluid delivery assembly 3530 can be clicked into proper alignment relative to the drive assembly 3540 (e.g., one handed). In some embodiments, the latch retention features 3537 can be located on the drive assembly 3540 and engage with retention features 3547 on the fluid delivery assembly housing 3570.

Figure 40A:
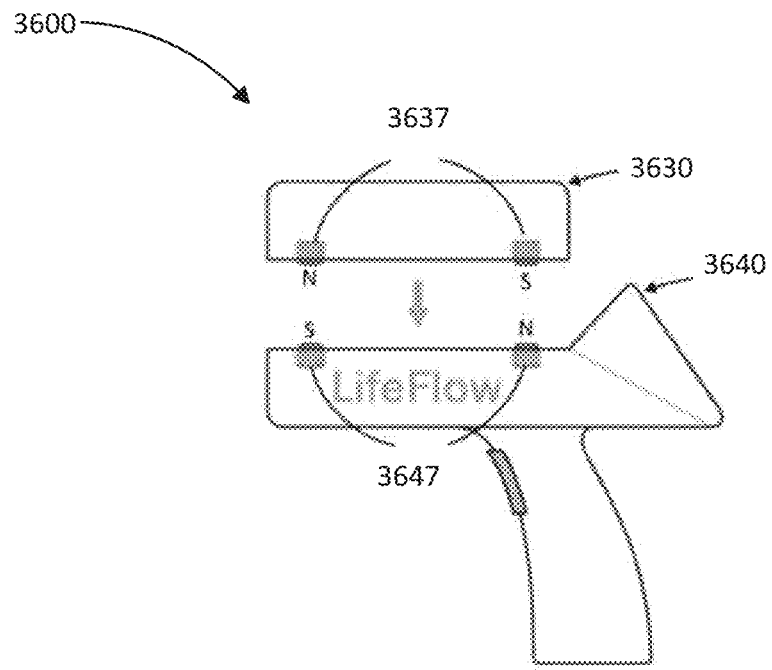
FIGS. 40A and 40B are schematic illustration of a system in a first configuration and a second configuration, respectively, according to an embodiment.
Figure 40B:
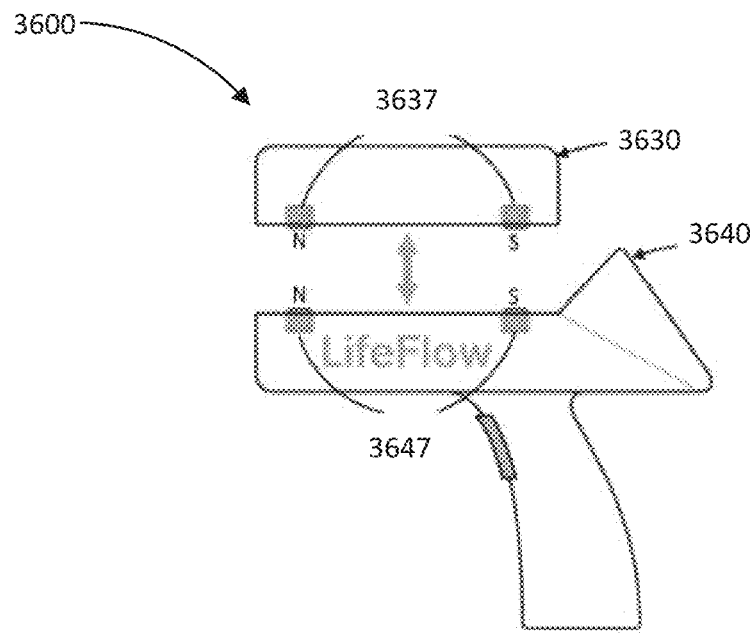

In some embodiments, a fluid delivery assembly and a drive assembly can be coupled using magnetic interaction. For example, FIGS. 40A and 40B are schematic illustrations of a system including a fluid delivery assembly 3630 and a drive assembly 3640. The system 3600 can be the same or similar in structure and/or function to any of the systems described herein. The fluid delivery assembly 3630 and the drive assembly 3640 can be coupled using magnetic interaction between the assemblies. FIG. 40A shows an embodiment in which magnets 3637 are located in the fluid delivery assembly 3630 and magnets 3647 are located in the drive assembly 3640. The polarities of the magnets 3637 in the fluid delivery assembly 3630 are oriented in such a way relative to the polarities of the magnets 3647 in the reusable drive assembly 3640 that the two assemblies are attracted to one another and the attractive magnetic interaction holds the two assemblies together during use (i.e., opposite polarities mating with one another). Additional alignment features, such as any of the alignment features described herein, may be used to ensure proper alignment between the two assemblies and/or to provide resistance to torque generated by a drive transfer mechanism of the drive assembly 3640 such that the fluid delivery assembly 3630 does not rotate relative to the drive assembly 3640. As shown in FIG. 40B, the polarities of the magnets 3637 in the fluid delivery assembly 3630 and the polarities of the magnets 3647 in the drive assembly 3640 may also be oriented such that incorrect (e.g., backwards) orientation of the fluid delivery assembly 3630 relative to the drive assembly 3640 results in a repulsive magnetic interaction between the two assemblies, preventing incorrect assembly. Thus, the fluid delivery assembly 3630 can be clicked into proper alignment relative to the drive assembly 3640 (e.g., one handed).

In some embodiments, magnets can be located in only one of the assemblies and a paramagnetic material (e.g., steel, stainless steel, etc.) can be disposed within or coupled to the other assembly. For example, magnets 3637 can be located in the fluid delivery assembly 3630 and paramagnetic retention features 3647 can be located in the drive assembly 3640. In some embodiments, a motor of the drive assembly 3640 (e.g., a motor such as the motor 2142) can be used as the paramagnetic material 3647 to attract the magnets 3637 in the fluid delivery assembly 3630. Alternatively, magnets 3647 can be located in the drive assembly 3640 and paramagnetic retention features 3637 can be located in the fluid delivery assembly 3630.

Figure 41:
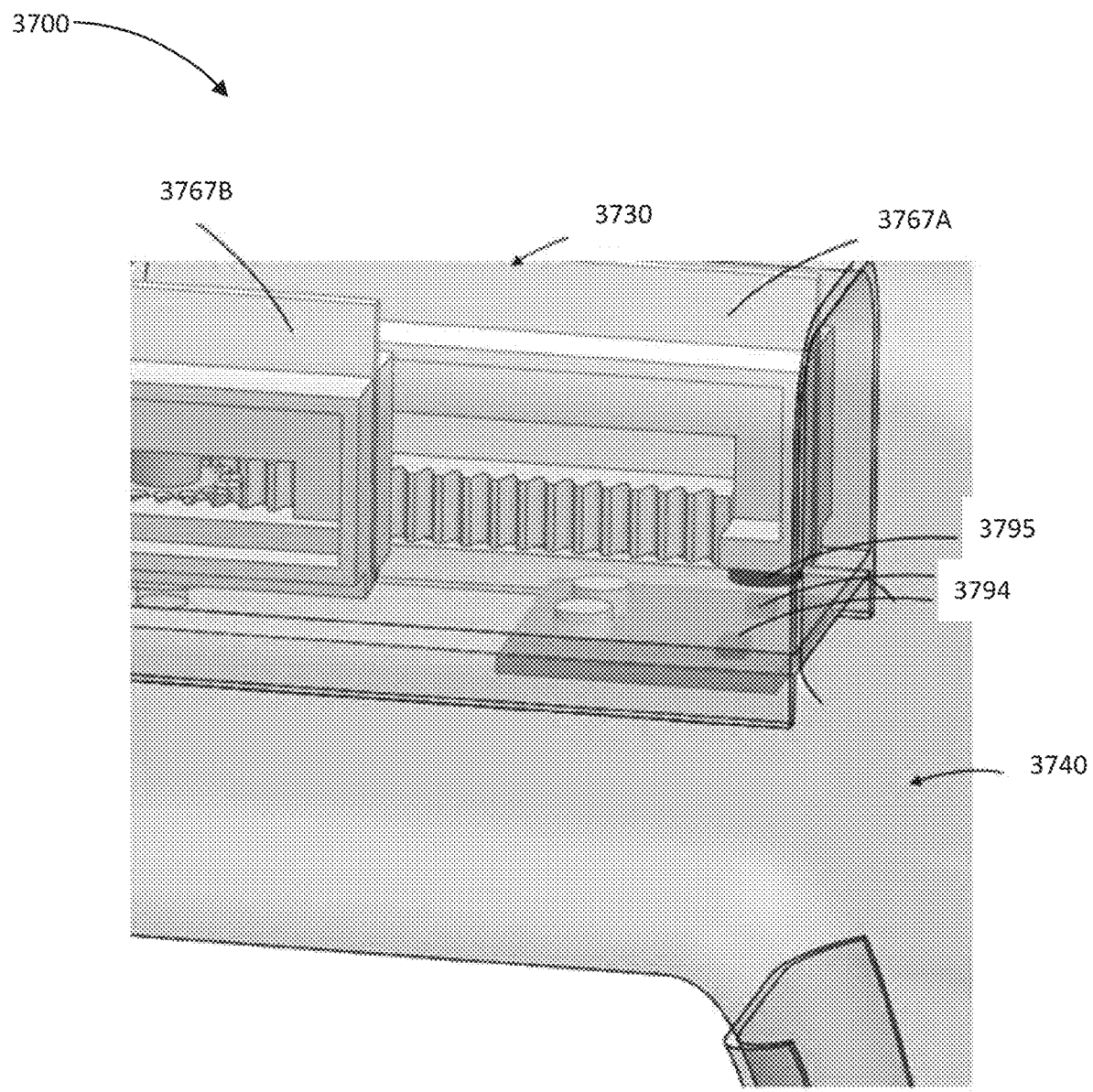
FIG. 41 is a perspective view of a portion of a system, according to an embodiment.

In some embodiments, the direction of translation of plungers, and thus pistons, of a fluid delivery assembly can be controlled based in part on a sensor. For example, FIG. 41 is a perspective view of a portion of a system 3700. The system 3700 can be the same or similar in structure and/or function to any of the systems described herein. For example, the system 3700 includes a fluid delivery assembly 3730 and a drive assembly 3740. The fluid delivery assembly 3730 includes a first plunger 3767A and a second plunger 3767B. A magnet 3795 is coupled to each plunger 3767A, 3767B and the drive assembly 3740 includes a sensor 3794 associated with each plunger 3767A, 3767B. Each sensor 3794 can be activated by the presence of the magnet 3795 (e.g., each sensor 3794 can be a Hall Effect Sensor). The magnets 3795 and sensors 3794 are located such that each sensor 1894 is activated when the respective plunger 3767A, 3767B reaches the end of its travel path (e.g., the end associated with the maximum volume of a reservoir associated with the respective plunger). For example, the plunger 3767A is shown at the end of its travel path with the magnet 3795 of the plunger 3767A aligned with its associated sensor 3794 in FIG. 41. When a sensor 3794 is activated, the drive assembly 3740 (e.g., under control of a controller of the drive assembly 3740) reverses the direction of translation of the plungers 3767A, 3767B (e.g., by reversing direction of a drive transfer mechanism of the drive assembly 3740).

Figure 42A:
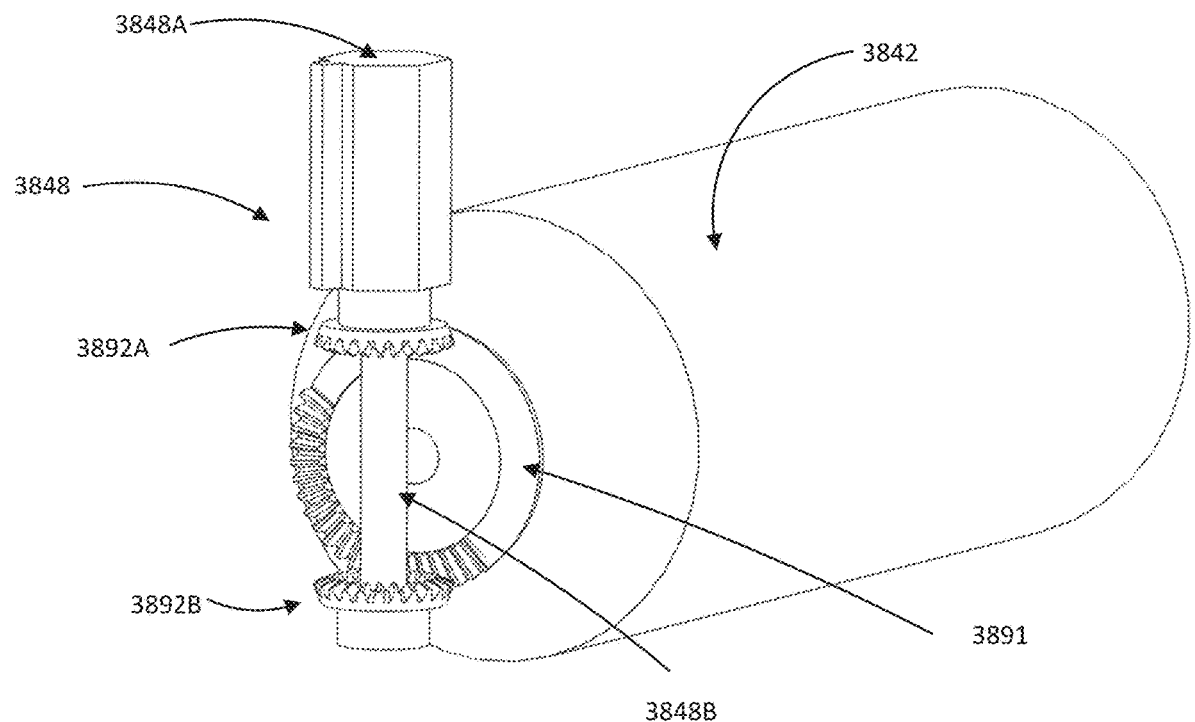
FIG. 42A is a perspective view of a portion of a drive assembly, according to an embodiment.
Figure 42B:
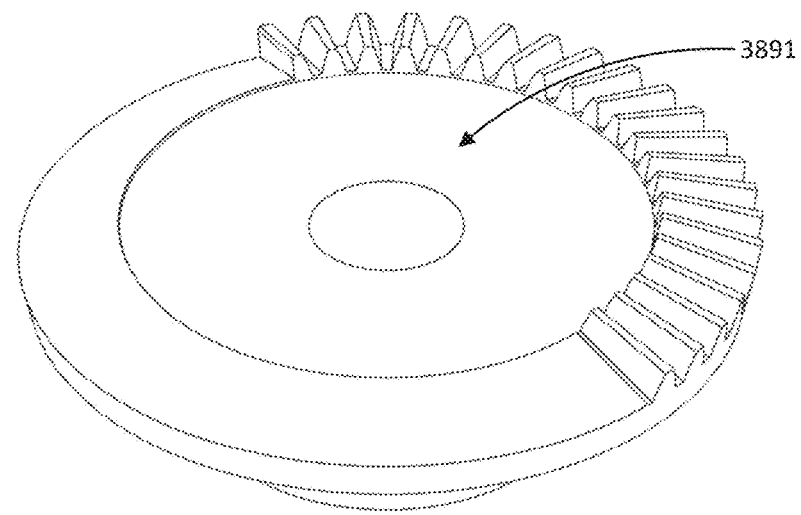
FIG. 42B is a perspective view of an interrupted bevel gear of the drive assembly of FIG. 42A.

FIG. 42A is a perspective view of a portion of a drive assembly including a drive transfer mechanism 3848 having a driveshaft portion 3848A configured to be coupled to a drive mechanism of a fluid delivery assembly, such as any of the fluid delivery assemblies described herein, and to be mechanically controlled by a motor 3842 such that motion of the driveshaft 3848A can drive pistons in the fluid delivery assembly. The drive assembly portions shown in FIGS. 42A and 42B can be included in any of the drive assemblies described herein. The mechanism coupling the motor 3842 to the driveshaft 3848 includes an interrupted bevel drive gear 3891, two driven bevel gears 3892A and 3892B, a section of driveshaft 3848B between the two driven bevel gears 3892A and 3892B and a section of the driveshaft 3848A to engage with a drive mechanism of a fluid delivery assembly. FIG. 42B is a perspective view of the interrupted bevel gear 3819. The interrupted bevel gear 3891 can have teeth disposed on only a portion of its perimeter (e.g., less than half of the perimeter) such that the teeth of the interrupted bevel gear 3891 only engage with one of the two driven gears 3892A and 3892B of the drive mechanism at any time. The motor 3842 can operate to cause rotation of the interrupted bevel gear 3891 in one direction, and the teeth of the interrupted bevel gear 3891 can alternate contact with each of the two driven gears 3892A and 3892B. When the teeth of the interrupted bevel gear 3891 are meshed with the driven gear 3892A, the driveshafts 3848A and 3848B rotate in a first direction. When the teeth of the interrupted bevel gear 3891 are meshed with the driven gear 3892B, the driveshafts 3848A and 3848B rotate in a second direction opposite of the first direction. The driveshaft 3848A can be engaged with a drive mechanism of a fluid delivery assembly (e.g., the pinion 665 or the pinion 865) such that rotation of the driveshaft 3848A in a first direction causes a first piston to translate in a first direction and second piston to translate in a second direction opposite the first direction, and when the driveshaft 3848A is rotated in a second direction, the first piston is translated in the second direction and the second piston is translated in the first direction. Thus, the fluid delivery assembly coupled to the driveshaft 3848A can generate an uninterrupted delivery of fluid under control of the motor 3842 with the motor 3842 rotating the interrupted bevel gear 3891 continuously in one direction. As shown in FIG. 42A, the driveshaft 3848A can include a keyed portion for engagement with a keyway of a pinion, such as the pinion 2765 shown in FIG. 31. In some embodiments, the driveshaft 3848A can be coupled to or include a gear such as the gear 2848A shown in FIG. 32A or the gear 2948A shown in FIG. 33A.

Figure 43A:
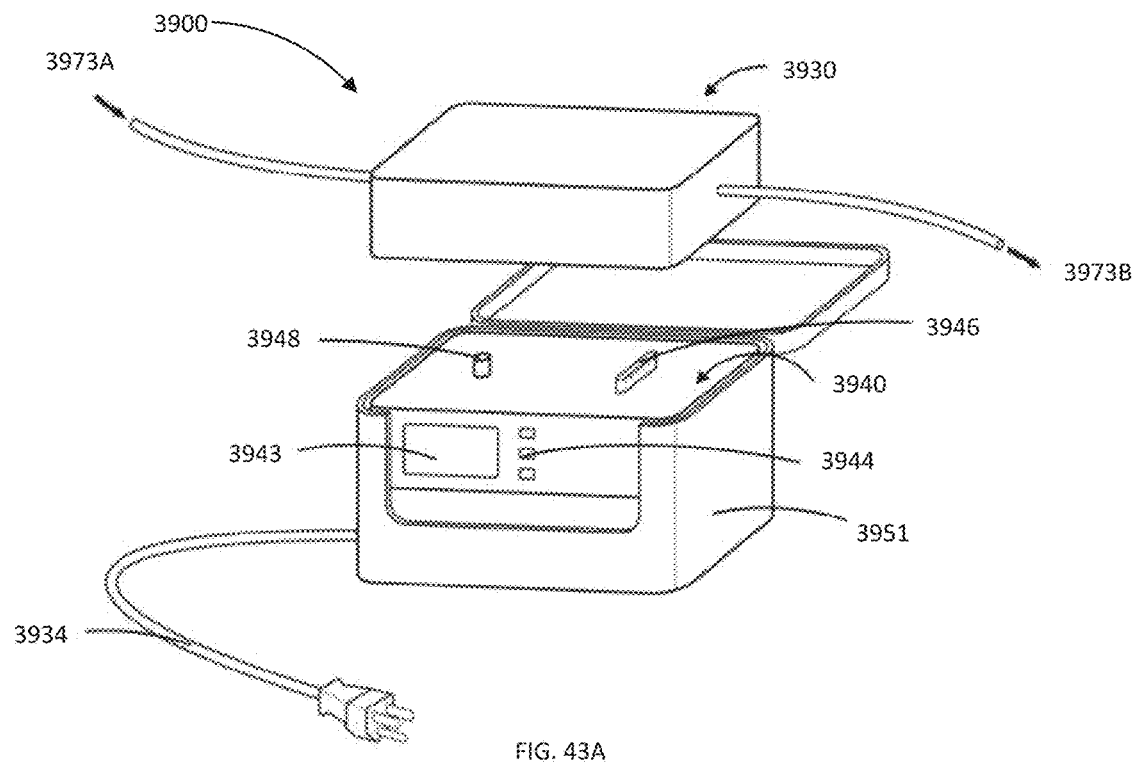
FIGS. 43A-43C are illustrations of perspective views of a system, according to an embodiment.
Figure 43B:
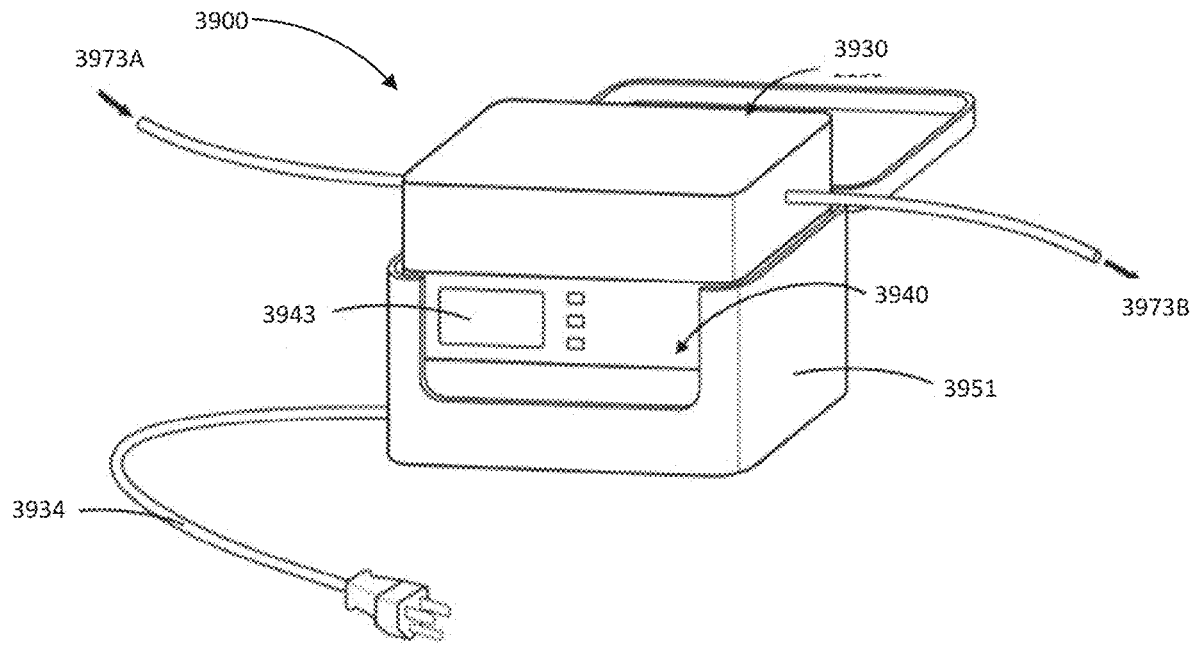
Figure 43C:
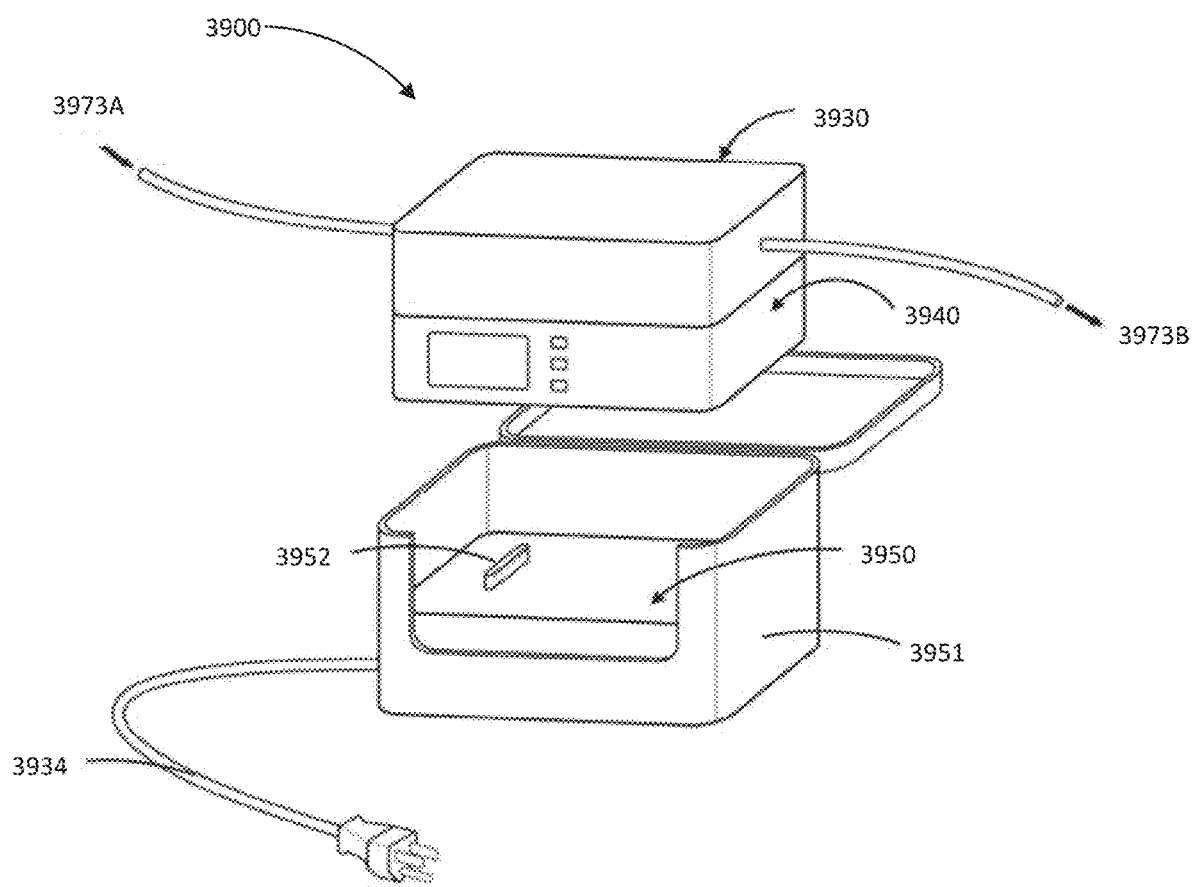

In some embodiments, rather than a system or a drive assembly being handheld, a system can be set on a surface (e.g., a patient bed or the ground) or mounted to an IV pole rather than held in a user's hand during use. FIGS. 43A-43C are perspective views of a non-handheld system 3900 in various stages of operation. The system 3900 can be the same or similar in structure and/or function to any of the systems described herein. For example, the system 3900 includes a fluid delivery assembly 3930 and a drive assembly 3940. The system 3900 also includes an optional housing 3151. The fluid delivery assembly 3930 can include one or more of a fluid pump, mechanical and electrical connections, and/or a fluid warmer (e.g., configured to warm blood and/or saline). The blood and fluid warmer can be configured to convert electrical energy into heat via electrical resistance. The fluid delivery assembly 3930 includes a fluid inlet line 3173A and a fluid outlet line 3973B. The drive assembly 3940 includes a drive transfer mechanism 3948 and an electrical connection 3946 (also referred to as an electrical contact), which are configured to be coupled to the fluid delivery assembly 3930 such that the drive transfer mechanism 3948 controls fluid travel through the fluid delivery assembly 3930 and the electrical connection 3946 is configured to exchange power and/or data the fluid delivery assembly 3930 via an electrical connection of the fluid delivery assembly. The drive assembly 3940 also includes a display 3943 and user interface features 3944. The system 3900 also optionally includes a power source 3950 (e.g., disposed within the housing 3951) including an electrical connection 3952 configured to be coupled to an electrical connection of the drive assembly 3940 to provide power to the drive assembly 3940. The power source 3950 can include, for example, a rechargeable battery, and can be configured to receive power (e.g., operational power and/or charging power) from an AC power source via, for example, an optional AC power cord 3934.

FIG. 43A is a perspective view of the system 3900 with the fluid delivery assembly 3930 uncoupled from the drive assembly 3940, as it would be immediately prior to assembly by the user. FIG. 43B is a perspective view of the system 3900 with the fluid delivery assembly 3930 coupled to the drive assembly 3940, which is coupled to the power supply 3950. When AC power is available, the system can be powered from AC power in the configuration in FIG. 43B. In the configuration of FIG. 43B, the system 3900 can pump fluid (e.g., saline or blood) from a source bag to a patient using either battery power or AC power. FIG. 43C is a perspective view of the system 3900 in a configuration in which the fluid delivery assembly 3930 is coupled to the drive assembly 3940 and both the fluid delivery assembly 3930 and the drive assembly 3940 are uncoupled and separated from the power supply 3950 and removed from the housing 3951. In this configuration, the fluid delivery assembly 3930 can be powered by a power source (e.g., a battery) included in the drive assembly 3940 (e.g., within a housing of the drive assembly 3940). By separating the fluid delivery assembly 3930 and the drive assembly 3940 from the power supply 3950, the user would have a smaller, lighter and more portable system or subsystem, which could continue to pump fluid to a patient via battery power for some time after separation form the power supply 3950. For example, the battery of the drive assembly 3940 can have a stored power capacity sufficient to provide flow and/or fluid warming for between about 0.5 L and about 4 L of fluid (e.g., saline or blood).

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

The invention claimed is:

1. A system, comprising:
a fluid delivery assembly including a fluid delivery assembly housing, a drive mechanism, at least one reservoir, at least one piston, fluid inlet tubing, and fluid outlet tubing, the fluid inlet tubing coupled to the at least one reservoir and configured to be coupled to a source of fluid, the fluid outlet tubing coupled to the at least one reservoir and configured to be coupled to a patient, the drive mechanism configured to control movement of the at least one piston such that fluid is drawn into the at least one reservoir via the fluid inlet tubing and fluid is delivered from the at least one reservoir via the fluid outlet tubing, the at least one reservoir, the piston, and at least a portion of the drive mechanism being disposed within the fluid delivery assembly housing; and
a drive assembly including a drive assembly housing, a power storage component, a motor, and a drive transfer mechanism operatively coupled to the motor, the motor configured to operate based on power provided by the power storage component,
the power storage component, the motor, and at least a portion of the drive transfer mechanism being disposed within the drive assembly housing,
the drive transfer mechanism reversibly couplable to the drive mechanism of the fluid delivery assembly to control movement of the at least one piston of the fluid delivery assembly via the drive mechanism under the control of the motor.

2. The system of claim 1, further comprising an external power source including an electrical connection, the drive assembly including an electrical connection reversibly couplable to the electrical connection of the external power source such that the power storage component of the drive assembly can receive power from the external power source.

3. The system of claim 2, further comprising a system housing defining an interior space, the external power source and the drive assembly configured to be disposed within the interior space in a configuration in which the electrical connection of the drive assembly is coupled to the electrical connection of the external power source, the drive mechanism of the fluid delivery assembly configured to be coupled to the drive transfer mechanism of the drive assembly when the external power source and the drive assembly are disposed within the interior space of the system housing.

4. The system of claim 2, wherein the power storage component of the drive assembly is configured to receive power from the external power source in a first configuration in which the electrical connection of the drive assembly is coupled to the electrical connection of the external power source such that a power storage level of the power storage component increases, and the drive assembly is configured to operate to control the movement of the at least one piston based on power stored in the power storage component in a second configuration in which the drive assembly is decoupled from the external power source and the drive transfer mechanism of the drive assembly is coupled to the drive mechanism of the fluid delivery assembly.

5. The system of claim 4, wherein, in the first configuration, the drive assembly is configured to operate to control the movement of the at least one piston based on power received from the external power source when the drive mechanism of the fluid delivery assembly is coupled to the drive transfer mechanism.

6. The system of claim 1, wherein the drive assembly housing has a side surface, and the fluid delivery assembly housing has a side surface, the side surface of the fluid delivery assembly housing contacting the side surface of the fluid delivery assembly housing when the drive transfer mechanism is coupled to the drive mechanism of the fluid delivery assembly.

7. The system of claim 6, wherein the fluid delivery assembly is configured to magnetically couple to the drive assembly such that the drive transfer mechanism is coupled to the drive mechanism of the fluid delivery assembly.

8. The system of claim 1, wherein the fluid delivery assembly includes a warmer subassembly configured to warm fluid traveling through the fluid delivery assembly, the warmer subassembly disposed within the fluid delivery assembly housing.

9. The system of claim 8, wherein the fluid delivery assembly includes an electrical connection configured to be coupled to an electrical connection of the drive assembly such that the warmer subassembly can operate based on power provided to the warmer subassembly from the power storage component of the drive assembly via the electrical connection of the drive assembly and the electrical connection of the fluid delivery assembly.

10. The system of claim 1, wherein the fluid delivery assembly includes an electrical connection, and the drive assembly includes an electrical connection configured to be coupled to the electrical connection of the fluid delivery assembly such that data can be transferred between the fluid delivery assembly and the drive assembly.

11. The system of claim 1, wherein the fluid delivery assembly includes a first alignment feature and the drive assembly includes a second alignment feature configured to be reversibly engaged with the first alignment feature such that the fluid delivery assembly is prevented from rotating relative to the drive assembly during operation of the motor of the drive assembly.

12. The system of claim 1, wherein the fluid delivery assembly includes a first retention mechanism and the drive assembly includes a second retention mechanism configured to be reversibly engaged with the first retention mechanism such that the fluid delivery assembly is prevented from being separated from the drive assembly during operation of the motor of the drive assembly.

13. The method of claim 1, wherein the at least one reservoir includes a first reservoir and a second reservoir, the fluid delivery assembly configured such that fluid is drawn into the first reservoir while fluid is delivered from the second reservoir and such that fluid is drawn into the second reservoir while fluid is delivered from the first reservoir.

14. The method of claim 1, wherein the at least one reservoir includes a first reservoir and a second reservoir, the at least one piston includes a first piston and a second piston, and the fluid delivery assembly includes a fluid pump including a first syringe defining the first reservoir and including the first piston and a second syringe defining the second reservoir and including the second piston, the fluid pump disposed within the fluid delivery assembly housing, the first syringe configured to draw fluid while the second syringe delivers fluid and the first syringe configured to deliver fluid while the second syringe draws fluid.

15. The system of claim 14, wherein the fluid delivery assembly includes a set of one-way valves configured to prevent fluid from flowing toward the source of fluid from the fluid pump, toward the fluid pump from the patient, and between the first syringe and the second syringe.

16. The system of claim 14, wherein the set of one-way valves includes a first one-way valve disposed between an inlet of the fluid pump and a distal opening of the first syringe, a second one-way valve disposed between the distal opening of the first syringe and an outlet of the fluid pump, a third one-way valve disposed between the inlet of the fluid pump and a distal opening of the second syringe, and a fourth one-way valve disposed between the distal opening of the second syringe and the outlet of the fluid pump.

17. The system of claim 14, wherein the drive transfer mechanism is configured to rotate to control movement of the drive mechanism to cause a plunger of the first syringe to be translated in an opposite direction than a plunger of the second syringe such that fluid is simultaneously drawn into the fluid delivery assembly via the fluid inlet tubing and delivered from the fluid delivery assembly via the fluid outlet tubing.

18. The system of claim 1, wherein the fluid delivery assembly includes a first alignment feature and the drive assembly includes a second alignment feature configured to be reversibly engaged with the first alignment feature such that the fluid delivery assembly is prevented from rotating relative to the drive assembly during operation of the motor of the drive assembly, and
  the fluid delivery assembly includes a first retention mechanism and the drive assembly includes a second retention mechanism configured to be releasably engaged with the first retention mechanism such that the fluid delivery assembly is prevented from being separated from the drive assembly during operation of the motor of the drive assembly.

* * * * *

UNITED STATES PATENT AND TRADEMARK OFFICE
CERTIFICATE OF CORRECTION

PATENT NO. : 11,744,936 B2  
APPLICATION NO. : 17/845560  
DATED : September 5, 2023  
INVENTOR(S) : Andrew W. Lane et al.

Page 1 of 1

It is certified that error appears in the above-identified patent and that said Letters Patent is hereby corrected as shown below:

In the Claims

At Column 54, Line number 1 (Claim number 13, Line number 1): "The method of claim 1, wherein the at least one" should read -- The system of claim 1, wherein the at least one --

At Column 54, Line number 7 (Claim number 14, Line number 1): "The method of claim 1, wherein the at least one" should read -- The system of claim 1, wherein the at least one --

At Column 54, Line number 23 (Claim number 16, Line number 1): "The system of claim 14, wherein the set of one-way" should read -- The system of claim 15, wherein the set of one-way --

Signed and Sealed this  
Fifteenth Day of July, 2025

Coke Morgan Stewart  
*Acting Director of the United States Patent and Trademark Office*